United States Patent
Clader et al.

(10) Patent No.: US 7,452,891 B2
(45) Date of Patent: Nov. 18, 2008

(54) MCH ANTAGONISTS AND THEIR USE IN THE TREATMENT OF OBESITY

(75) Inventors: John W. Clader, Cranford, NJ (US); Hubert B. Josien, Hoboken, NJ (US); Anandan Palani, Bridgewater, NJ (US); Tin Yau Chan, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 194 days.

(21) Appl. No.: 11/045,713

(22) Filed: Jan. 28, 2005

(65) Prior Publication Data

US 2005/0171098 A1 Aug. 4, 2005

Related U.S. Application Data

(62) Division of application No. 10/100,840, filed on Mar. 19, 2002, now Pat. No. 6,900,329.

(60) Provisional application No. 60/277,584, filed on Mar. 21, 2001.

(51) Int. Cl.
| | |
|---|---|
| *A61K 31/495* | (2006.01) |
| *C07D 295/15* | (2006.01) |
| *A61K 31/444* | (2006.01) |
| *A61K 31/451* | (2006.01) |
| *A61K 31/5375* | (2006.01) |
| *C07D 401/06* | (2006.01) |
| *C07D 401/10* | (2006.01) |
| *C07D 405/06* | (2006.01) |

(52) U.S. Cl. ............................... 514/255.03; 514/237.8; 514/238.5; 514/318; 514/331; 544/129; 544/163; 544/165; 544/336; 544/295; 544/357; 544/399; 544/400; 546/197; 546/201; 546/230; 546/231; 546/234

(58) Field of Classification Search ................. 544/400, 544/399

See application file for complete search history.

(56) References Cited

U.S. PATENT DOCUMENTS

2004/0063779 A1* 4/2004 Dollinger et al. ............ 514/464

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Vippagunta et al. Advanced Drug Delivery Reviews, vol. 48, pp. 3-26 (2001).*

* cited by examiner

*Primary Examiner*—Emily Bernhardt
(74) *Attorney, Agent, or Firm*—Palaiyur S. Kalyanaraman; William Y. Lee

(57) ABSTRACT

The present invention discloses compounds which, are novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

20 Claims, No Drawings

MCH ANTAGONISTS AND THEIR USE IN THE TREATMENT OF OBESITY

REFERENCE TO RELATED APPLICATIONS

This application claims priority to U.S. Ser. No. 10/100,840 filed on Mar. 19, 2002, which claims the benefit of U.S. Provisional Application No. 60/277,584, filed Mar. 21, 2001.

BACKGROUND OF THE INVENTION

This invention relates to antagonists for melanin-concentrating hormone (MCH) and their use in the treatment of metabolic and eating disorders.

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (17 Dec. 1998), pp. 670-673, MCH-deficient mice have reduced body weight and leanness due to hypophagia (reduced feeding). In view of their findings, it was suggested that antagonists of MCH action may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist.

SUMMARY OF THE INVENTION

In one embodiment, this invention provides novel compounds having MCH antagonist activity. These compounds are represented by structural formula I:

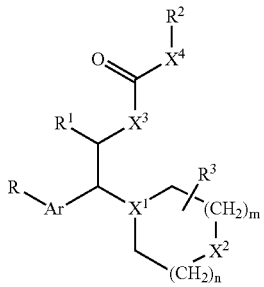

I or a pharmaceutically acceptable salt, solvate or prodrug thereof, wherein m is a number from 0 to 3;

n is a number from 0 to 3;

m and n maybe the same or different;

$X^1$ is CH, N, or C—$(C_1$-$C_3)$alkyl;

$X^2$ is N—$R^5$, $CH_2$, O, S, SO, $SO_2$, CH—$((C_1$-$C_6)$alkyl), or CH—$(CH_2O$—$(C_1$-$C_3)$alkyl);

$X^3$ is O or N—$R^6$;

$X^4$ is a single bond, O, N, NH, N—$R^7$ or when $X^4$ is N, $R^2$ and $X^4$ can join together to form a heterocycloalkyl group such as piperidine, pyrrolidine, morpholine, piperazine, thiomorpholine or

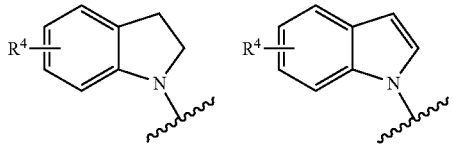

where the N of $X^4$ is the heteroatom of said heterocycloalkyl group, wherein said heterocycloalkyl groups can be optionally substituted with one or more alkyl, aryl, aralkyl, or cycloalkylalkyl;

Ar is an arylene or heteroarylene group;

R is $R^4$-phenyl, $R^4$-pyridyl, $R^4$-pyridyl-N-oxide, $R^4$-pyrazyl or $R^4$-pyrimidyl;

$R^1$ is hydrogen, or $(C_1$-$C_3)$alkyl;

$R^2$ is alkyl, arylalkyl, substituted arylalkyl, cycloalkyl, cycloalkylalkyl (i.e. cyclopropylmethyl), $R^8$-phenyl, $R^8$-pyridyl, $R^8$-pyridyl-N-oxide;

$R^3$ is hydrogen, OH, —$O(C_1$-$C_3)$alkyl, or non-substituted or halosubstituted $(C_1$-$C_3)$alkyl;

$R^4$ and $R^8$ maybe the same or different, may number 0 to 3, each being independently selected from the group consisting of hydrogen, —$(C_1$-$C_6)$alkyl, —$(C_3$-$C_7)$cycloalkyl, halo, —CN, $(C_1$-$C_6)$alkoxy, —$CF_3$, —$OCF_3$, —$CONH_2$, —$CONH(C_1$-$C_6)$alkyl, —$CON(C_1$-$C_6)$alkyl $(C_1$-$C_6)$alkyl, —$NH_2$, —$NHC(O)(C_1$-$C_6)$alkyl, —$NHC(O)NH(C_1$-$C_6)$alkyl, —$NHC(O)N((C_1$-$C_6)$alkyl)$((C_1$-$C_6)$alkyl), —$NHSO_2(C_1$-$C_6)$alkyl, —$S(C_1$-$C_6)$alkyl, —$SO(C_1$-$C_6)$alkyl, —$SO_2(C_1$-$C_6)$alkyl, —$SO_2NH(C_1$-$C_6)$alkyl, —$O(C_1$-$C_3)$alkyleneO—, and $NO_2$ or two adjacent $R^4$ or two adjacent $R^8$ groups together may form a methylenedioxy, propylenedioxy or ethylenedioxy group;

$R^5$ is hydrogen, nonsubstituted or halosubstituted —$(C_1$-$C_6)$alkyl, nonsubstituted or halosubstituted $(C_3$-$C_7)$cycloalkyl, nonsubstituted or halosubstituted $(C_3$-$C_7)$cycloalkyl$(C_1$-$C_6)$alkyl, nonsubstituted or halosubstituted —$(C_1$-$C_6)$alkylene$(C_1$-$C_6)$alkoxy, nonsubstituted or halosubstituted alkoxycarbonyl, nonsubstituted or halosubstituted aryl, nonsubstituted or halosubstituted heterocycloalkyl, nonsubstituted or halosubstituted heteroaryl, nonsubstituted or halosubstituted aralkyl, nonsubstituted or halosubstituted $(C_1$-$C_6)$alkylbenzimidazole, nonsubstituted or halosubstituted heteroaralkyl, nonsubstituted or halosubstituted $C(O)NH(C_1$-$C_3)$alkylene $N(R^9)_2$, —$SO_2(C_1$-$C_6)$alkyl or wherein $R^5$ is independently selected from, —$SO_2NH_2$, —$SO_2NH$alkyl, —$SO_2N$alkyl$_2$,

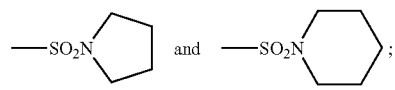

$R^6$ and $R^7$ may be the same or different, each being independently selected from hydrogen, nonsubstituted or halosubstituted $(C_1$-$C_3)$alkyl; or $R^6$ and $R^7$ can be joined together to form a 4 to 7-membered ring; and $R^9$ is hydrogen, $(C_1$-$C_6)$alkyl, $(C_3$-$C_7)$cycloalkyl, $(C_3$-$C_7)$cycloalkylmethyl, aralkyl or heteroaralkyl, or the moiety —$N(R^9)_2$ may represent a pyrrolidine, piperazine or piperidine wherein the N of $N(R^9)_2$ is the N of said pyrrolidine, piperazine or piperidine.

One group of preferred compounds is that of formula I wherein $X^1$ is CH or N;

$X^2$ is N—$R^5$;

$X^3$ is O or N—$R^6$;

$X^4$ is O, or N—$R^7$, preferably N—$R^7$;

Ar is 1,4-phenylene;

R is $R^4$-phenyl, or $R^4$-pyridyl, preferably when $R^4$ numbers 1 and substitutes at the meta position of said phenyl or pyridyl;

$R^1$ is hydrogen;

$R^2$ is $R^8$-phenyl, where $R^8$ is preferably 1-3 substituents which may be the same or different, each being independently selected from halogen, $CF_3$—, or $(C_1$-$C_3)$ alkoxy-;

$R^3$ is hydrogen or methyl;

$R^4$ is 1 to 3 substituents which may be the same or different, each being independently selected from hydrogen, halogen, or CN;

$R^5$ is hydrogen, nonsubstituted or halosubstituted $(C_1$-$C_6)$ alkyl, cyclopropylmethyl, $CH_2$-aryl, $CH_2$-heteroaryl, $CH_2$—$CH_2$—O—$(C_1$-$C_6)$alkyl, or $SO_2$—$(C_1$-$C_6)$alkyl;

$R^6$ and $R^7$ are hydrogen; and m and n are the same or different and are equal to 0 or 1.

Another preferred group of compounds are compounds of formula I wherein $X^2$ and $R^1$ are as defined above, $X^3$ is O or NH; $X^4$ is NH; R is $R^4$-phenyl or $R^4$-pyridyl and $R^4$ is 1 and substitutes at the meta position of said phenyl or pyridyl; $R^2$ is $R^8$-phenyl, where $R^8$ is preferably 1-3 substituents which may be same or different, each being independently selected from halogen, $CF_3$, or $(C_1$-$C_3)$alkyl-O—; $R^3$ is hydrogen or methyl; $R^4$ is 1 to 3 substituents which may be the same or different, each being independently selected from hydrogen, halogen or CN; $R^5$ is hydrogen, nonsubstituted or halosubstituted $(C_1$-$C_6)$alkyl, cyclopropylmethyl, $CH_2$-aryl, $CH_2$-heteroaryl, $CH_2$—$CH_2$—O—$(C_1$-$C_6)$alkyl, or $SO_2$—$(C_1$-$C_6)$alkyl; $R^6$ and $R^7$ are hydrogen; and m and n are the same or different and are equal to 0 or 1.

A further preferred compound is a compound of formula I wherein $X^2$ and $R^1$ are as defined above, Ar is 1,4-arylene, $R^1$ is H, $R^3$ is H, $X^1$ is CH, $X^2$ is N—$R^5$, $X^3$ is O or NH, $X^4$ is NH, n is 1 and m is 1, $R^5$ is $(C_1$-$C_3)$alkyl, $(C_3$-$C_7)$cycloalkyl, cyclopropylmethyl, 4-morpholinyl, or 2-methoxyethyl; R is 3-cyanophenyl or 3-pyridyl and $R^2$ is 3,5-dichlorophenyl, 3-chloro-4-fluorophenyl, 3,4-difluorophenyl, 3,5-difluorophenyl, 3,5-dichloro-4-pyridyl, 3-trifluoromethyl-4-fluorophenyl, or 3-fluoro-4-trifluoromethylphenyl.

A further preferred compound is a compound of formula I wherein $X^2$ and $R^1$ are as defined above Ar is 1,4-arylene, $R^1$ is H, $R^3$ is H, $X^1$ is CH, $X^2$ is N—$R^5$, $X^3$ is O or NH, $X^4$ is NH, n is 1 and m is 1, $R^5$ is selected from the group of $CH_3$, cyclopropylmethyl, cyclopentyl or cyclohexyl; R is 3-cyanophenyl or 3-pyridyl, $R^2$ is 3,5-dichlorophenyl, 3-chloro-4-fluorophenyl,3,4-difluorophenyl, 3,5-difluorophenyl, 3,5-dichloro-4-pyridyl, 3-trifluoromethyl-4-fluorophenyl, or 3-fluoro-4-trifluoromethylphenyl.

An even further preferred group of compounds are those listed below in the Detailed Description in Table 1.

This invention is also directed to pharmaceutical compositions for the treatment of metabolic disorders such as obesity and eating disorders such as hyperphagia. In particular, this invention is also directed to pharmaceutical compositions for the treatment of obesity which comprise an obesity treating amount of a compound of formula, I, a prodrug thereof, or a pharmaceutically acceptable salt of said compound or of said prodrug and a pharmaceutically acceptable carrier therefor.

DETAILED DESCRIPTION

The present invention relates to compounds, that are MCH antagonists, represented by structural formula I, or a pharmaceutically acceptable salt or solvate thereof, wherein the various moieties are as described above.

The present antagonists of formula I can be administered as racemic mixtures or enantiomerically pure compounds.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other mammals.

"Mammal" means humans and other animals.

"Alkyl" means an aliphatic hydrocarbon group, which may be straight or branched and comprising 1 to 20 carbon atoms in the chain. Preferred alkyl groups contain 1 to 12 carbon atoms in the chain. More preferred alkyl groups contain 1 to 6 carbon atoms in the chain. Branched means that one or more lower alkyl groups such as methyl, ethyl or propyl, are attached to a linear alkyl chain. "Lower alkyl" means a group having 1 to 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl, n-butyl, and t-butyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 12 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain, which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group containing at least one carbon-carbon triple bond and which may be straight or branched and comprising 2 to 15 carbon atoms in the chain. Preferred alkynyl groups have 2 to 12 carbon atoms in the chain; and more preferably 2 to 4 carbon atoms in the chain. Branched means that one or more lower alkyl groups such as methyl, ethyl or propyl, are attached to a linear alkynyl chain. "Lower alkynyl" means 2 to 6 carbon atoms in the chain, which may be straight or branched. Non-limiting examples of suitable alkynyl groups include ethynyl, propynyl, and 2-butynyl,. The term "substituted alkynyl" means that the alkynyl group may be substituted by one or more substituents which may be the same or different, each substituent being independently selected from the group consisting of alkyl. aryl and cycloalkyl.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising 6 to 14 carbon atoms, preferably 6 to 10 carbon atoms. The aryl group can be unsubstituted or optionally substituted on the ring with one or more substituents which may be the same or different, each being independently selected from the group consisting of alkyl, aryl, $OCF_3$, OCOalkyl, OCOaryl, $CF_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different, each being independently selected from the group consisting of hydrogen, alkyl, aryl, and aralkyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heteroarylene" means a bivalent group derived from a heterocyclic aromatic compound by removal of a hydrogen atom from two ring carbon atoms such as, for example, the bivalent group derived from pyridine, pyrrole and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthlenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising 3 to 10 carbon atoms, preferably 5 to 10 carbon atoms. Preferred cycloalkyl rings contain 5 to 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising 3 to 10 carbon atoms, preferably 5 to 10 carbon atoms which contains at least one carbon-carbon double bond. Preferred cycloalkenyl rings contain 5 to 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different each being independently selected from the group consisting of hydrogen, alkyl, aryl, and aralkyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising 3 to 10 ring atoms, preferably 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different each being independently selected from the group consisting of hydrogen, alkyl, aryl, and aralkyl. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2-dihydropyridyl, 1,4-dihydropyridyl, 1,2,3,6-tetrahydropyridyl and the like. Non-limiting examples of suitable oxaheterocyclenyl groups include 3,4-dihydro-2H-pyran, dihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different each being independently selected from the group consisting of hydrogen, alkyl, aryl, and aralkyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl and the like.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of 5 to 6 ring atoms. The arylcycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, beteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different each being independently selected from the group consisting of hydrogen, alkyl, aryl, and aralkyl. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of 5 to 6 ring atoms. The arylcycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different each being independently selected from the group consisting of hydrogen, alkyl, aryl, and aralkyl. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of 5 to 6 ring atoms and the cycloalkyl consists of 5 to 6 ring atoms. The prefix aza, oxa or thia before heteroaryl means that at least a nitrogen, oxygen or sulfur atom is present respectively as a ring atom. The heteroarylcycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2$N-alkyl-, $Y_1Y_2$NC(O)— and $Y_1Y_2NSO_2$—, wherein $Y_1$ and $Y_2$ may be the same or different each being independently selected from the group consisting of hydrogen, alkyl, aryl, and aralkyl. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 4,5, 6,7-tetrahydro-1H-benzimidazolyl, and the like. The bond to the parent moiety is through a non-aromatic carbon atom.

"Cycloalkylheteroaryl" means a group derived from a fused heteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen-is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—$CH_3$, —C(O)—$CH_2CH_3$ and the like.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S($O_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design,* (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by MCH, and thus producing the desired therapeutic effect.

Prodrugs and solvates of the compounds of the invention are also contemplated herein. The term "prodrug", as employed herein, denotes a compound that is a drug precursor, which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association, and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention. All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

When any variable (e.g., aryl, heterocycle, $R_1$, etc.) occurs more than one time in any constituent or in Formula I, its definition on each occurrence is independent of its definition at every other occurrence. Also, combinations of substituents and/or variables are permissible only if such combinations result in stable compounds.

N-oxides can form on a tertiary nitrogen present in an $X^1$, R or $R^2$ substituent, or on =N— in a heteroaryl ring substituent and are included in the compounds of formula I.

An preferred group of compounds are those listed below in Table 1.

TABLE 1
| Compound | Structure |
|---|---|
| 26 | 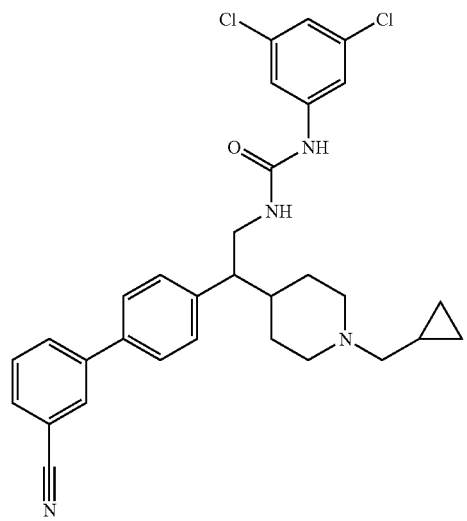 |
| 17 | 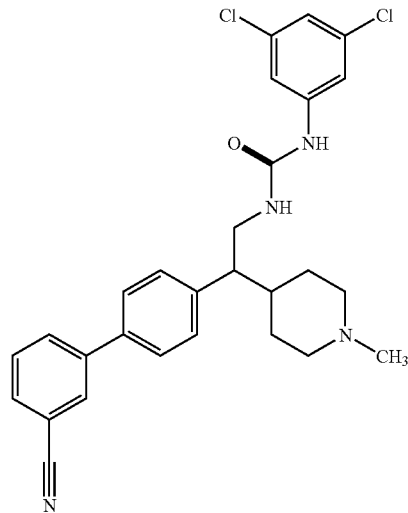 |
| 75 | 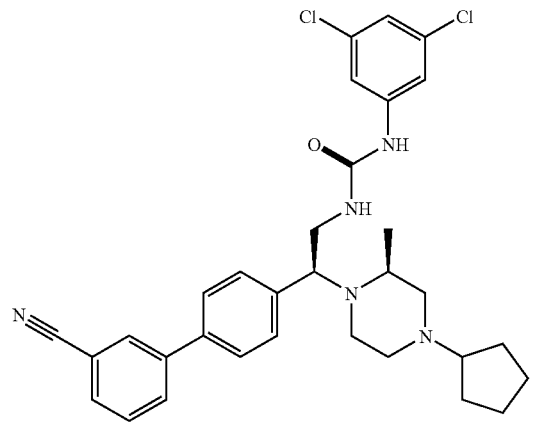 |

TABLE 1-continued
| Compound | Structure |
|---|---|
| 66 | 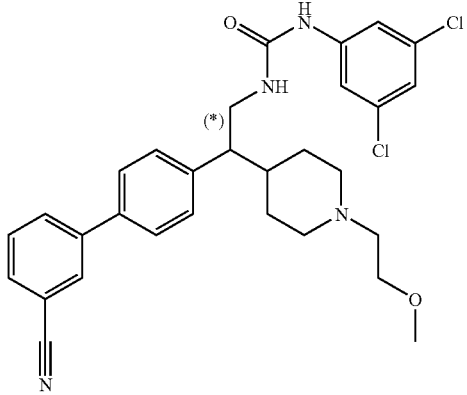 |
| 87 | 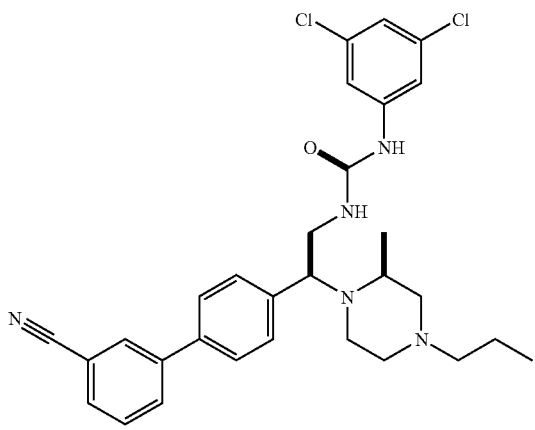 |
| 74 | 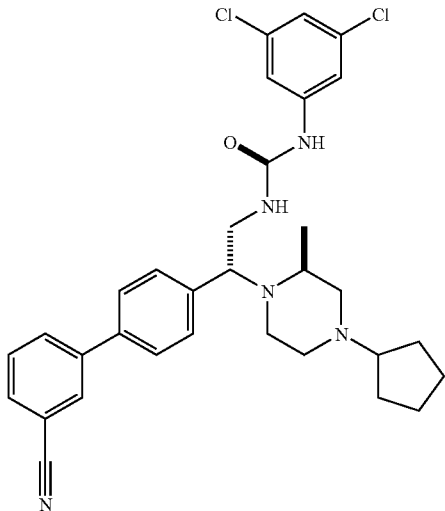 |

TABLE 1-continued
| Compound | Structure |
|---|---|
| 9 | 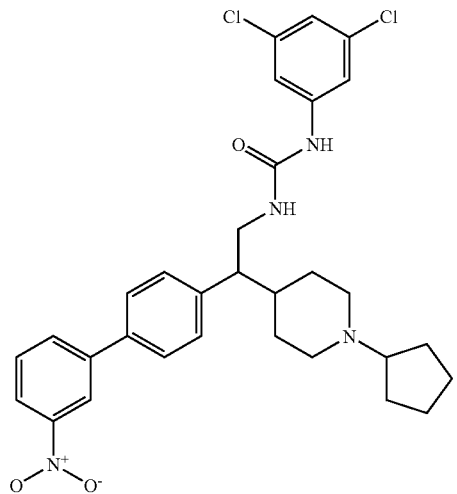 |
| 60 | 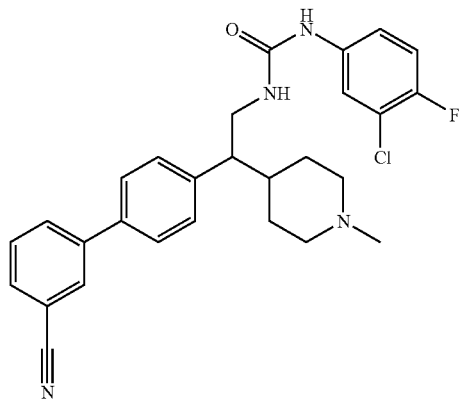 |
| 83 | 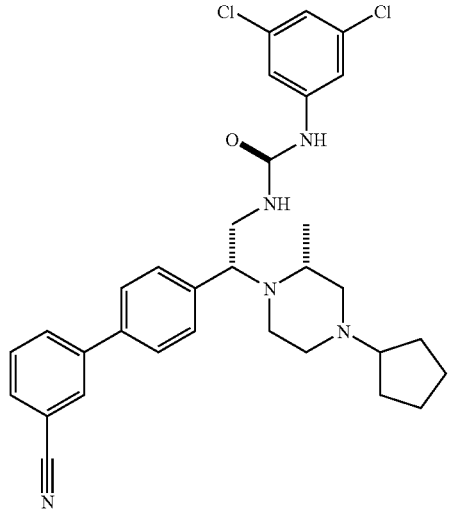 |

TABLE 1-continued
| Compound | Structure |
|---|---|
| 12 | 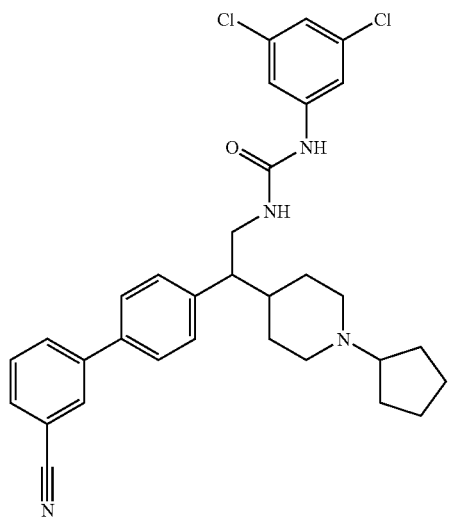 |
| 31 | 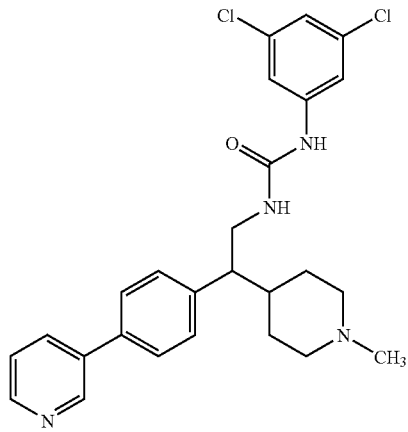 |
| 56 | 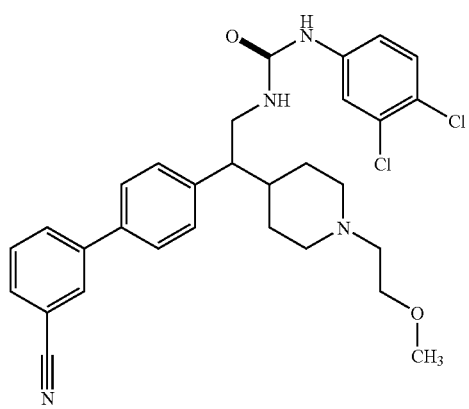 |

TABLE 1-continued
| Compound | Structure |
|---|---|
| 3 | 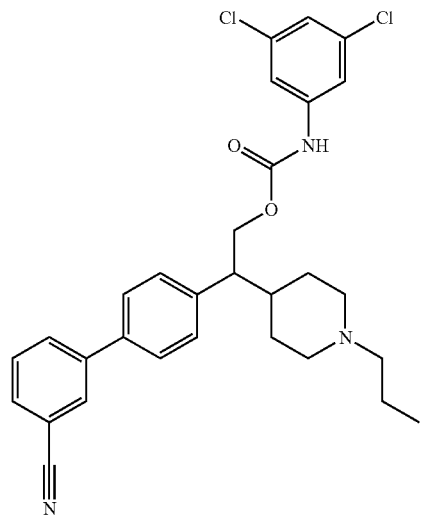 |
| 55 | 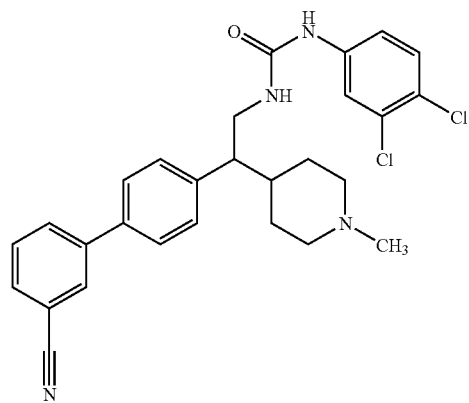 |
| 69 | 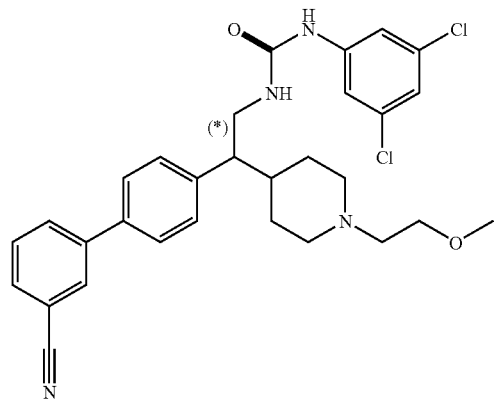 |

TABLE 1-continued
| Compound | Structure |
|---|---|
| 1 | 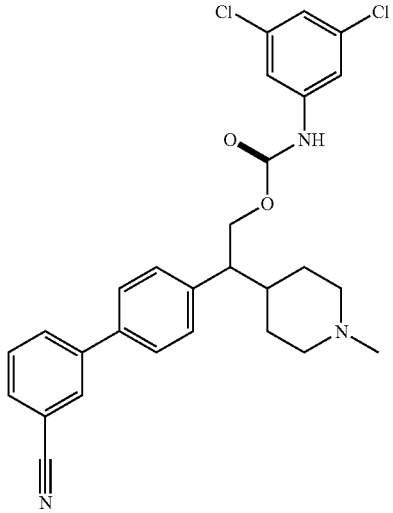 |
| 32 | 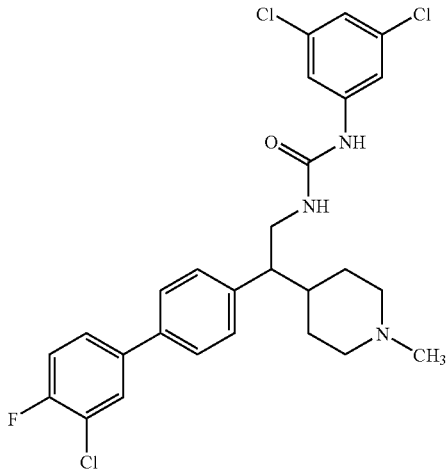 |
| 30 | 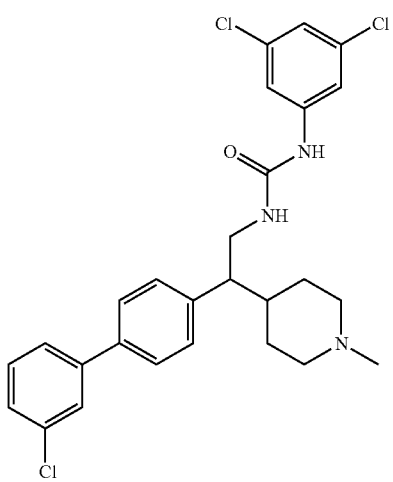 |

TABLE 1-continued
| Compound | Structure |
|---|---|
| 112 | 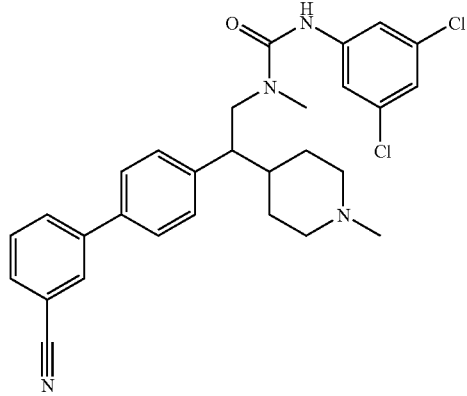 |
| 6 | 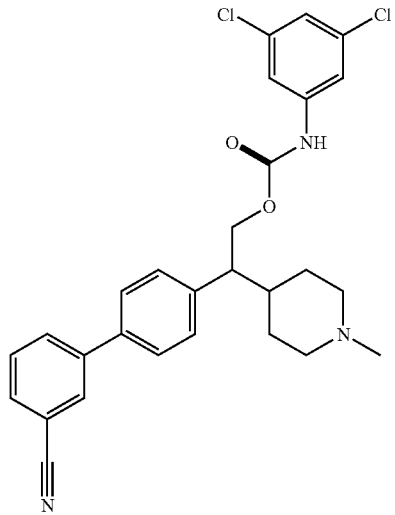 |
| 14 | 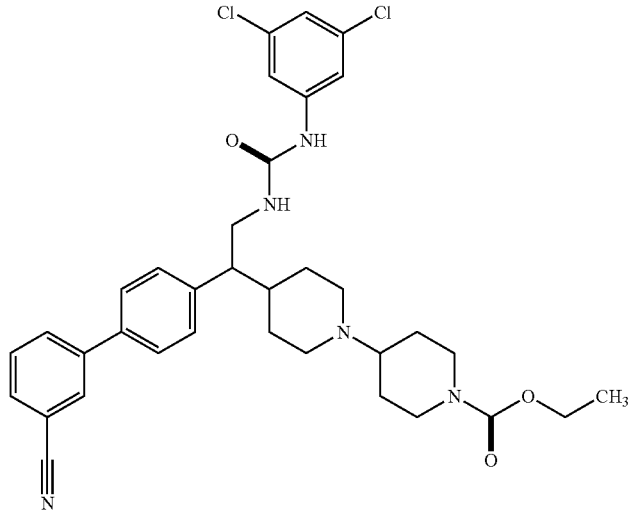 |

TABLE 1-continued

| Compound | Structure |
|---|---|
| 45 | 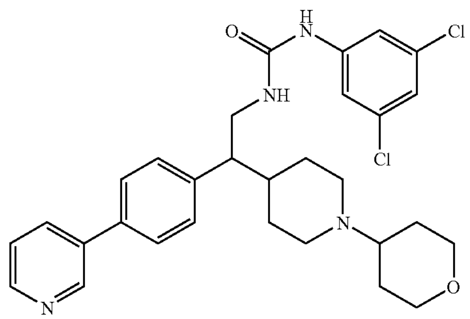 |
| 88 | 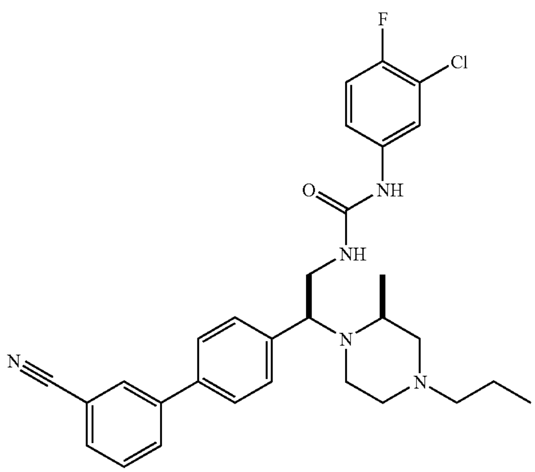 |
| 27 | 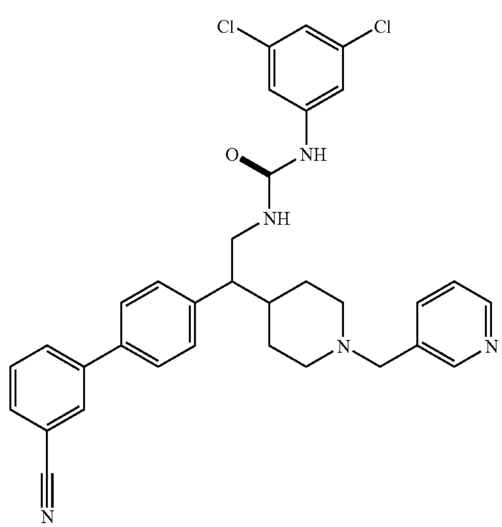 |

TABLE 1-continued

Compound Structure

64 [Chemical structure showing a urea-linked compound with a 3,5-dichlorophenyl group, a biphenyl moiety with NH substituent, and a piperidine ring bearing NH-NH2]

Another aspect of this invention is a method of treating a mammal (e.g., human) having a disease or condition mediated by MCH by administering a therapeutically effective amount of at least one compound of formula I, a prodrug thereof, or a pharmaceutically acceptable salt of said compound or of said prodrug to the mammal.

A preferred dosage is about 0.001 to 100 mg/kg/day of the formula I compound or a prodrug thereof. An especially preferred dosage is about 0.01 to 25 mg/kg/day of a compound of formula I, a prodrug thereof, or a pharmaceutically acceptable salt of said compound or of said prodrug.

Another aspect of this invention is directed to a method of treating obesity comprising administering to a mammal in need of such treatment a therapeutically effective amount of at least one compound of formula I or a prodrug thereof, or a pharmaceutically acceptable salt of said compound or of said prodrug.

Another aspect of this invention is directed to a method for treating eating and metabolic disorders such as bulimia and anorexia comprising administering to a mammal a therapeutically effective amount of at least one compound of formula I, a prodrug thereof, or a pharmaceutically acceptable salt of said compound or of said prodrug.

Another aspect of this invention is directed to a method for treating hyperlipidemia comprising administering to a mammal a therapeutically effective amount of at least one compound of formula I, a prodrug thereof, or a pharmaceutically acceptable salt of said compound or of said prodrug.

Another aspect of this invention is directed to a method for treating cellulite and fat accumulation comprising administering to a mammal a therapeutically effective amount of at least one compound of formula I, a prodrug thereof, or a pharmaceutically acceptable salt of said compound or of said prodrug.

Another aspect of this invention is directed to a method for treating type II diabetes comprising administering to a mammal a therapeutically effective amount of at least one compound of formula I, a prodrug thereof, or a pharmaceutically acceptable salt of said compound or of said prodrug.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions which comprise at least one compound of formula I, a prodrug thereof, or a pharmaceutically acceptable salt of said compound or of said prodrug and at least one pharmaceutically acceptable carrier therefor.

This invention is also directed to pharmaceutical compositions for the treatment of obesity which comprise an obesity treating amount of at least one compound of formula, I, a prodrug thereof, or a pharmaceutically acceptable salt of said compound or of said prodrug and at least one pharmaceutically acceptable carrier therefor.

Compounds of formula I can be produced by processes known to those skilled in the art using either solution phase or solid phase synthesis as shown in the following reaction schemes, in the preparations and examples below, and by using the methods described in WO 98/05292, the disclosing of which is incorporated herein by reference.

The following solvents and reagents may be referred to by their abbreviations in parenthesis:
Thin layer chromatography (TLC);
diethyl ether ($Et_2O$);
dichloromethane ($CH_2Cl_2$);
1,2-dichloroethane (DCE);
ethyl acetate (AcOEt or EtOAc);
tetrahydrofuran (THF);
1,2-dimethoxyethane (DME);
methanol (MeOH);
ethanol (EtOH);
acetonitrile ($CH_3CN$);
N,N-dimethylformamide (DMF);
acetic acid (AcOH);
trifluoroacetic acid (TFA);
trifluoroacetic anhydride (TFAA);
sulfuric acid ($H_2SO_4$);
1-hydroxybenzotriazole (HOBt);
1-(3-dimethylaminopropyl)-3-ethyl carbodiimide hydrochloride (EDCl);
m-chloroperbenzoic acid (MCPBA);
ammonium hydroxide ($NH_4OH$);

triethylamine ($Et_3N$);
4-dimethylaminopyridine (DMAP);
tert-butoxycarbonyl (Boc or t-Boc);
High Performance Liquid Chromatography (HPLC);
melting point (M.pt.);
nuclear magnetic resonance spectroscopy (NMR);
mass spectral analysis (MS);
milliliters (mL);
grams (g);
room temperature (ambient) about 25° C. (rt);
(+)-(1R, 2R)-trans-1,2,3,4-tetrahydro-1-(methylamino) 2-naphthalenol hemitartrate (MAT); and
9-borabicyclo[3.3.1]nonane (9-BBN).

Compounds of formula Ia wherein $X^1$ is CH, $X^3$ is O, and Ar is 1,4-phenylene are prepared according to the method described in scheme 1:

Scheme 1

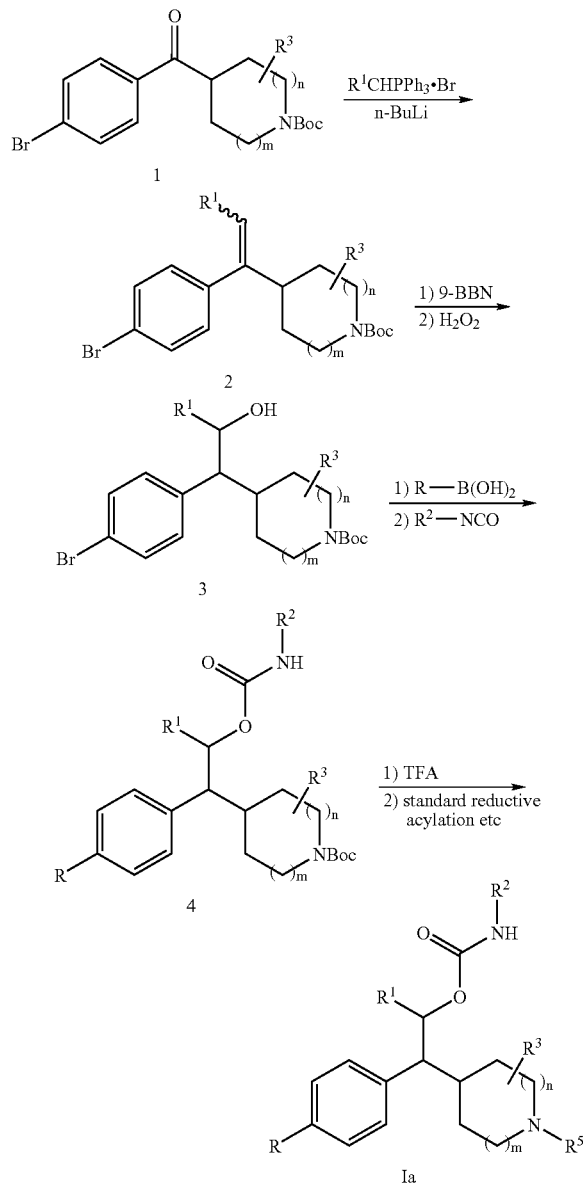

N-Boc ketone 1, easily prepared from the N-TFA precursor (the synthesis of which is described in WO98/05292 for m=n=1) via standard TFA-removal with potassium carbonate in methanol/water followed by N-protection with di-tert-butyldicarbonate, is subjected to Wittig olefination, followed by hydroboration and oxidation to afford alcohol 3. Suzuki coupling on alcohol 3 with arylboronic acid R—$B(OH)_2$ followed by treatment of the biaryl alcohol intermediate with isocyanate $R^2$—NCO give biaryl carbamate 4. This biaryl carbamate 4 is treated with TFA to remove the Boc-protecting group, and the resulting amine is further functionalized via reductive amination with an appropriate aldehyde or ketone, nucleophilic displacement with an alkyl- or aralkyl-halide, acylation with an acyl halide or sulfonation to provide biaryl carbamate Ia. Alternatively, the sequence of steps in Scheme 1 can be modified so that the Suzuki coupling reaction occurs after the condensation with the isocyanate $R^2$—NCO, or so that it is performed at the very end of the sequence, after removal of the Boc-protecting group and functionalization as above-mentioned.

Compounds of formula Ib wherein $X^1$ is CH, $X^3$ is NH, and Ar is 1,4-phenylene are prepared according to the method described in scheme 2:

Scheme 2

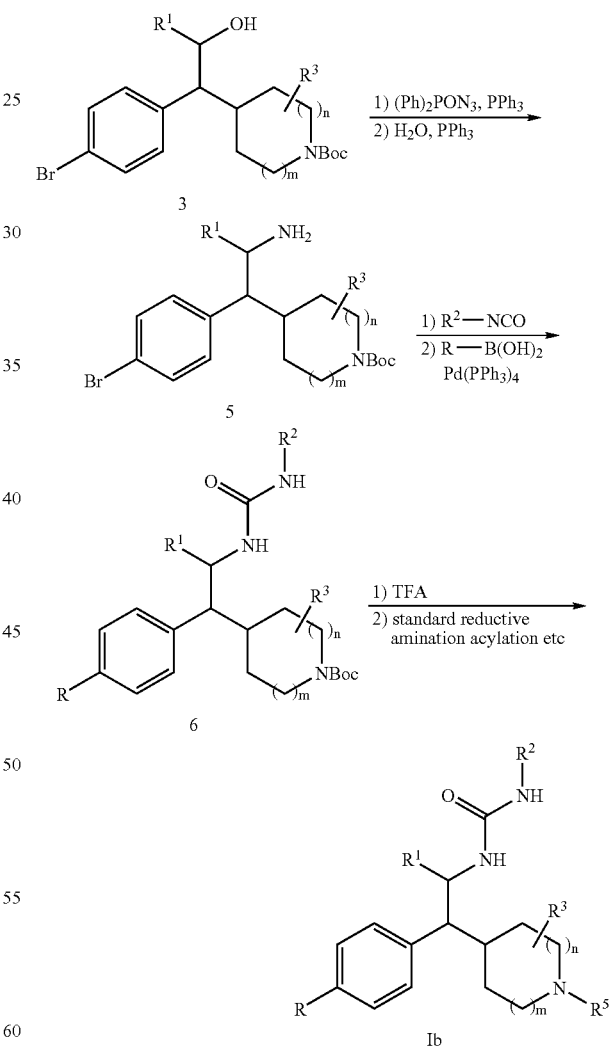

Intermediate 3 is reacted with diphenylphosphoryl azide followed by reduction of the intermediate azide to provide amine 5. Reaction of amine 5 with isocyanate $R^2$—NCO followed by Suzuki coupling with arylboronic acid R—$B(OH)_2$ affords biaryl urea 6. Then, and as for the end-synthesis of Ia, Boc removal with TFA and further functionalization of the resulting amine give biaryl urea Ib.

Compounds of formula Ic wherein $X^1$ is N, $X^3$ is NH, and Ar is 1,4-phenylene are prepared according to the method described in Scheme 3 (m and n=1):

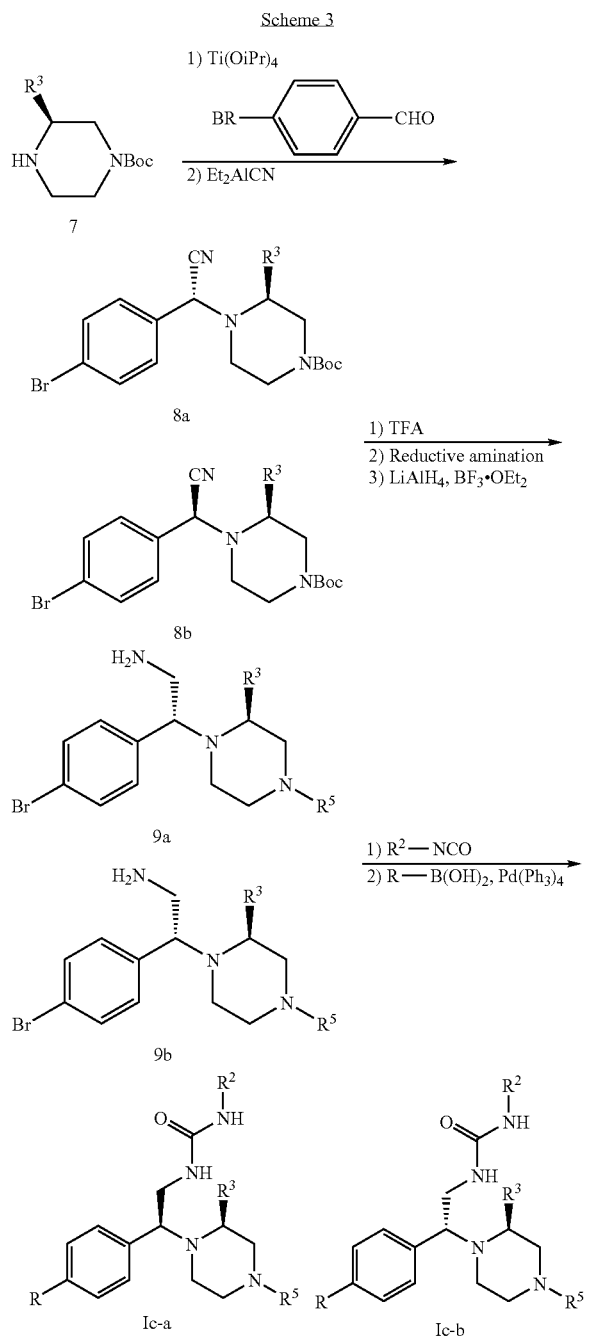

Reductive alkylation of piperazine 7 and 4-bromobenzaldehyde with titanium tetraisopropoxide and diethylaluminum cyanide affords Strecker amines 8a-b as a mixture of diastereoisomers. The Boc protective group in 8a-b is removed with TFA then the liberated free amine is functionalized via reductive amination with an appropriate aldehyde or ketone, or alkylation with an alkyl- or aralkyl-halide. The cyano group is then reduced with lithium aluminum hydride to give amines 9a and 9b that can be separated at that stage. Reaction of amine 9a and/or 9b with isocyanate $R^2$—NCO followed by Suzuki coupling with arylboronic acid R—B(OH)$_2$, affords piperazine biaryl urea Ic-a and/or Ic-b that can also be separated at that stage. Separation of the diastereoisomers can be performed at any stage of the synthesis following and including intermediates 9a-b. Any modification of the sequence in the scheme including the use of other protective groups or simplification when starting from a non-protected amine 7 would be apparent to those skilled in the art.

Combinatorial libraries of compounds of formula Ib can also be prepared using solid phase chemistry as shown in Scheme 4.

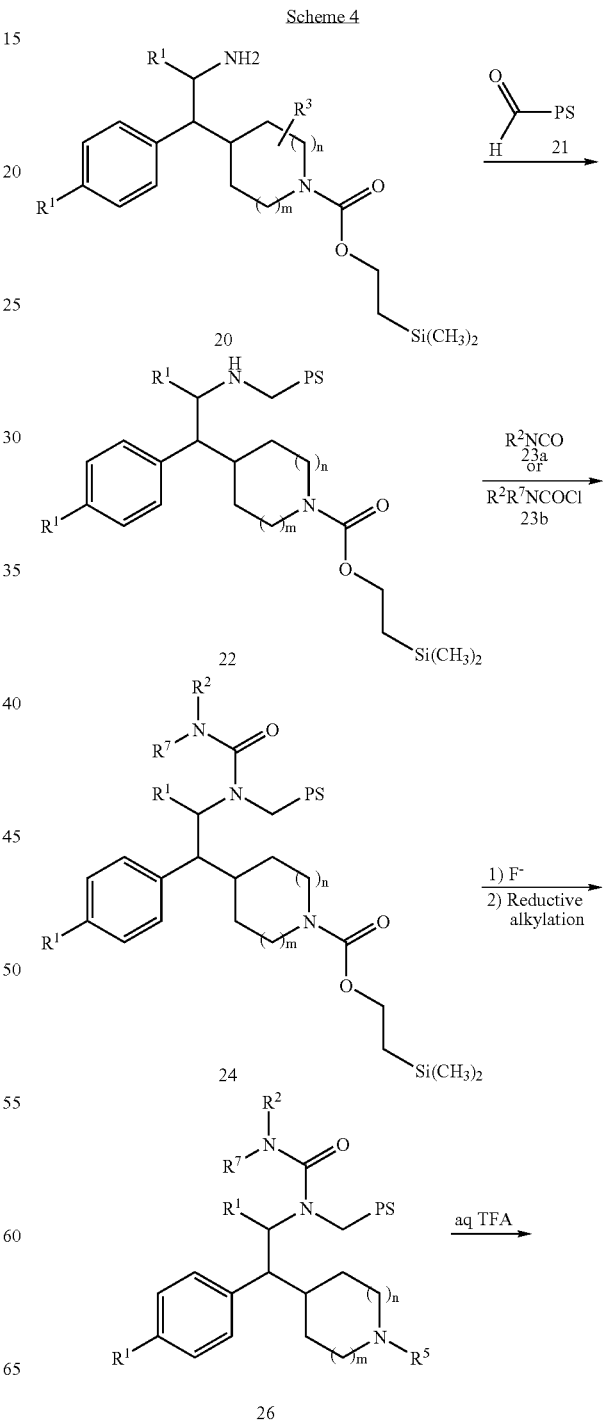

-continued

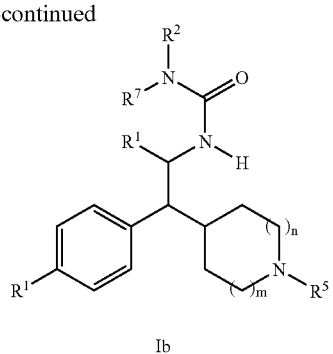

Ib

A library of intermediates 20, prepared in a manner similar to intermediate 5 of Scheme 2, is treated with a suitable solid-phase aldehyde reagent 21 such as Novabiochem 2-(4-formyl-3-methoxyphenoxy)ethyl polystyrene in the presence of a reducing agent such as sodium triacetoxyborohydride to give resin-bound amine 22. This is treated either with an isocyanate 23a or with a carbamoyl chloride 23b optionally in the presence of a base such as diisopropylethylamine to give urea 24. The protecting group is removed by treatment with fluoride, and the resulting free amine 25 is derivatized as described in Scheme 1 and Scheme 2 to give 26. The product is removed from the solid support by treatment with strong acid such as trifluoroacetic acid. Modifications to the sequence, including the use of alternative protecting groups, will be apparent to those skilled in the art.

Alternative mechanistic pathways and analogous structures within the scope of the invention would be apparent to those skilled in the art.

Starting materials are prepared by known methods and/or methods described in the Preparations.

The compounds of formula I exhibit MCH receptor antagonizing activity, which has been correlated with pharmaceutical activity for treating eating disorders, such as obesity and hyperphagia, and diabetes.

The compounds of formula I display pharmacological activity in a test procedure designed to demonstrate MCH receptor antagonist activity. The compounds are non-toxic at pharmaceutically therapeutic doses.

MCH Receptor Binding Assay:

Membranes from CHO cells expressing the MCH receptor were prepared by lysing cells with 5 mM HEPES for 15 min at 4 C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM MGCl$_2$, 10 mM NaCl, 5 mM MnCl$_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 µl) was then added to 96-well plates containing 50 µl of 500 pM [$^{125}$I]-MCH (NEN) and 50 ml of the appropriate concentration of compound (4× the desired final concentration). Nonspecific binding was determined by including 1 µM MCH in the binding reaction. The binding reaction was incubated at room temperature for 2 h. Plates were then analyzed in a TOP-COUNT microplate scintillation counter (Packard). Data was analyzed and Ki values were determined using GraphPad Prim.

For the compounds of this invention, a range of MCH receptor binding activity (Ki values) of from about 0.0 nM to about 1500 nM was observed. Compounds of this invention preferably have a binding activity in the range of from about 0.1 nM to about 250 nM, more preferably from about 0.6 to about 30 nM, and most preferably from about 0.6 to about 2 nM.

Yet another aspect of this invention are combinations of a compound of formula I, a prodrug thereof, or a pharmaceutically acceptable salt of said compound or of said prodrug and other compounds as described below.

Accordingly, another aspect of this invention is a method for treating obesity comprising administering to a mammal (e.g., a female or male human)

a. an amount of a first compound, said first compound being a formula I compound, a prodrug thereof, or a pharmaceutically acceptable salt of said compound or of said prodrug; and b. an amount of a second compound, said second compound being an antiobesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a formula I compound, a prodrug thereof, or a pharmaceutically acceptable salt of said compound or of said prodrug a second compound, said second compound being an antiobesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a formula I compound, a prodrug thereof, or a pharmaceutically acceptable salt of said compound or of said prodrug and a pharmaceutically acceptable carrier, vehicle or diluent in a first unit dosage form;

b. an amount of an antiobesity and/or anorectic agent such as a $\beta_3$ agonist, a thyromimetic agent, an anorectic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes comprising administering to a mammal (e.g., a female or male human)

a. an amount of a first compound, said first compound being a formula I compound, a prodrug thereof, or a pharmaceutically acceptable salt of said compound or of said prodrug; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a formula I compound, a prodrug thereof, or a pharmaceutically acceptable salt of said compound or of said prodrug; a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a formula I compound, a prodrug thereof, or a pharmaceutically acceptable salt of said compound or of said prodrug and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

EXAMPLES

Example 1

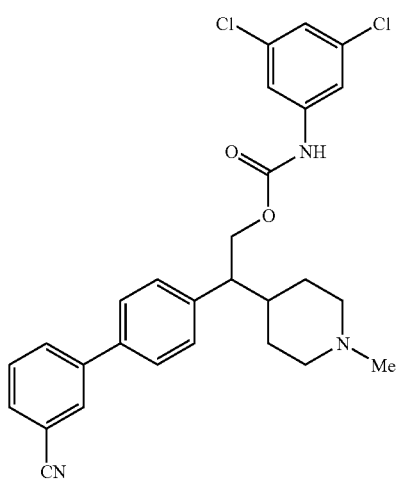

This compound (compound 1) was prepared according to Scheme 1.

Example 1-A

To a suspension of methyltriphenylphosphonium bromide (43.2 g; 121 mmol) in THF (350 ml) at −78 °C. was added n-butyl lithium 1.6 N solution in hexanes (75.6 ml; 121 mmol), and the solution was warmed to 0° C., stirred 5 minutes, then cooled to −78° C. A solution of bromoketone 1 (m and n=1; 40.0 g; 110 mmol) in THF (150 ml) was added and the mixture was allowed to warm to room temperature. After 30 minutes the crude was poured into $Et_2O$ and water, washed with half-saturated brine, brine, dried over $Na_2SO_4$ and concentrated to an oil. Purification by flash-chromatography over silica gel (eluting Hexanes/AcOEt 85:15) afforded 31.4 g (79%) of colorless olefin 2.

Example 1-B

To a solution of olefin 2 (21.0 g; 57 mmol) in THF (40 ml) at 0° C. was added 9-BBN 0.5 N solution in THF (198 ml) and the reaction was refluxed under nitrogen for 2 h. The cooled mixture was concentrated, slowly treated with a 1:1 mixture of THF/EtOH (140 ml) at 0° C. followed, 30 min later, by 30% $H_2O_2$ aqueous solution (140 ml). After stirring overnight at room temperature, the final solution was concentrated of EtOH, diluted with $CH_2Cl_2$, filtered over Celite, and extracted with $CH_2Cl_2$. Combined organic layers were dried over $Na_2SO_4$, concentrated and the crude was subjected to flash-chromatography over silica gel (eluting Hexanes/AcOEt 7:3 to 1:1) to give 17.6 g (84%) of colorless bromo alcohol 3.

Example 1-C

A mixture of bromo alcohol 3 (600 mg; 1.62 mmol), 3-cyanophenylboronic acid (310 mg; 2.10 mmol), $PdCl_2(PPh_3)_2$ (75 mg) and $Na_2CO_3$ (600 mg) in DME (2.5 ml) and water (2.5 ml) was heated at 72° C. for 5 h. The cooled solution was diluted with 0.1 N NaOH and extracted with $CH_2Cl_2$. Combined organic layers were dried over $Na_2SO_4$, concentrated and the crude was subjected to flash-chromatography over silica gel (eluting Hexanes/AcOEt 8:2 to 1:1) to provide 440 mg (67%) of biaryl alcohol.

Example 1-D

A mixture of biaryl alcohol (560 mg; 1.38 mmol), 3,5-dichlorophenyl isocyanate (320 mg; 1.7 mmol) and triethylamine (0.2 mL; 1.38 mmol) in THF (5 ml) was stirred overnight at room temperature. Concentration of the solvent followed by purification flash-chromatography over silica gel (eluting Hexanes/AcOEt 8:2 to 6:4) provided 600 mg (73%) of biaryl carbamate 4.

Example 1-E

A solution of biaryl carbamate 4 (350 mg) in $CH_2Cl_2$ (3 ml) and TFA (1 ml) was stirred 2 h at room temperature then concentrated. The crude was diluted with 1 N NaOH, extracted with $CH_2Cl_2$, and combined organic layers were dried over $Na_2SO_4$ and concentrated to provide 280 mg (96%) of biaryl carbamate amine.

Example 1-F

A solution of biaryl carbamate amine (30 mg; 0.06 mmol), 37% aqueous formaldehyde (50 μl), $Na_2SO_4$ (400 mg) and sodium triacetoxyborohydride (40 mg; 0.19 mmol) in DCE (0.5 ml) was stirred overnight at room temperature. The mixture was quenched with MeOH (0.2 ml), diluted 15 min later with 0.1 N NaOH and extracted with $CH_2Cl_2$. Combined organic layers were dried over $Na_2SO_4$, concentrated and the crude was purified by preparative chromatography over silica gel (eluting Hexanes/AcOEt 1:1) to give 8.5 mg of product 1a as free base. Trituration in $Et_2O$ provided 8.8 mg of hydrochloride salt as a foam: $^1$H-NMR (free base, 300 MHz, $CDCl_3$) δ 7.85 (s, 1H), 7.81 (br d, 1H), 7.62 (m, 1H), 7.50-7.60 (m, 3H), 7.25-7.35 (m, 4H), 7.03 (s, 1H), 6.84 (br s, 1H), 4.57 (dd, J=11 Hz and 5.6 Hz, 1H), 4.45 (dd, J=11 Hz and 9 Hz, 1H), 2.99 (br d, 1H), 2.80-2.95 (m, 2H), 2.30 (s, 3H), 1.85-2.10 (m, 3H), 1.30-1.75 (m, 4H); HRMS (M+H$^+$) 508.1564.

Using similar procedures, compounds of the following structures were prepared

TABLE 2

| Compound | Structure | HRMS (M + H+) | LCMS (retention time; MS | NMR |
|---|---|---|---|---|
| 2 | 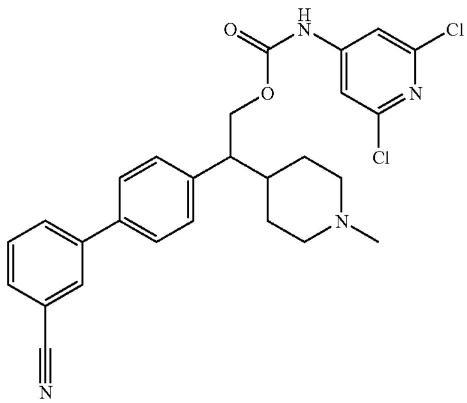 | 509.1514 | | |
| 3 | 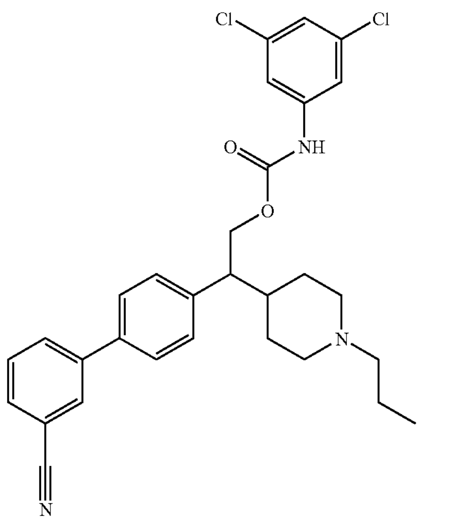 | 536.1881 | | |
| 4 | 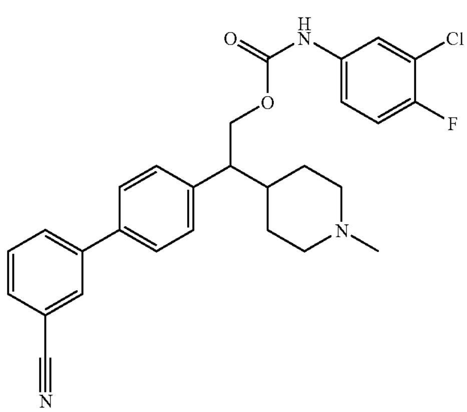 | 492.1845 | | |

TABLE 2-continued

| Compound | Structure | HRMS (M + H+) | LCMS (retention time; MS | NMR |
|---|---|---|---|---|
| 5 | 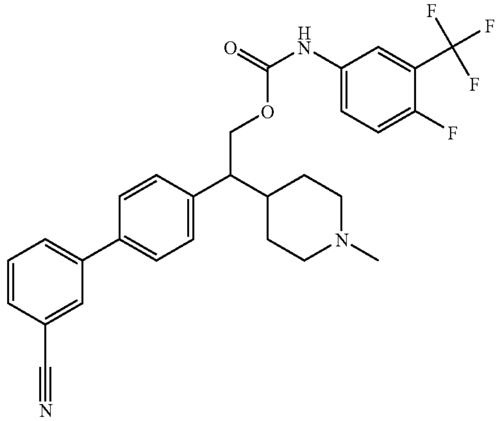 | 526.2106 | | |
| 5a | 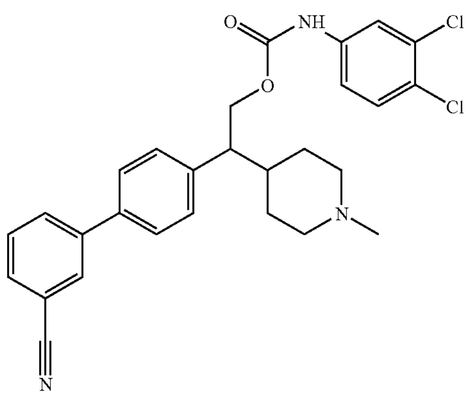 | 508.1554 | 5.66; 508.1 | |
| 5b | 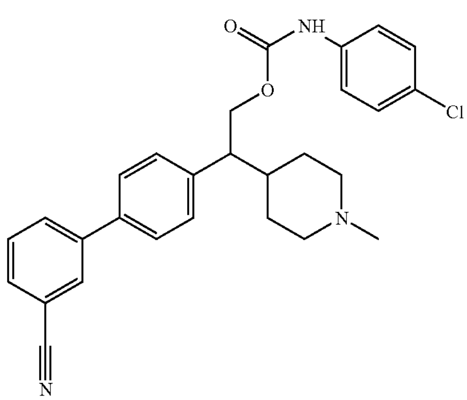 | 474.1941 | 5.51; 474.1 | |

TABLE 2-continued

| Compound | Structure | HRMS (M + H⁺) | LCMS (retention time; MS | NMR |
|---|---|---|---|---|
| 5c | 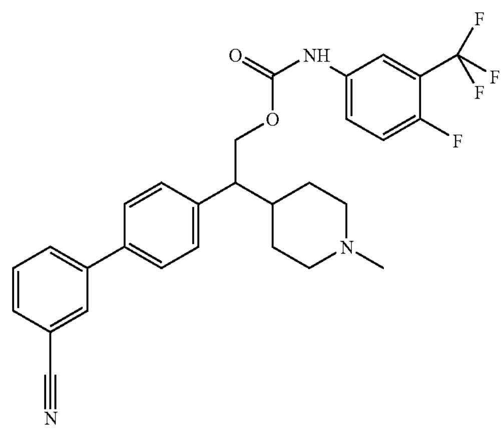 | 526.2106 | 5.56; 526.1 | |
| 5d | 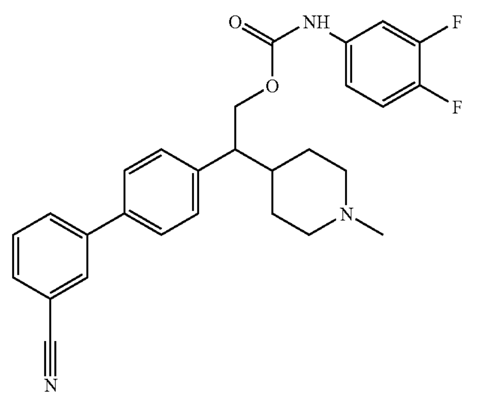 | 476.2154 | 5.31; 476.1 | |
| 5e | 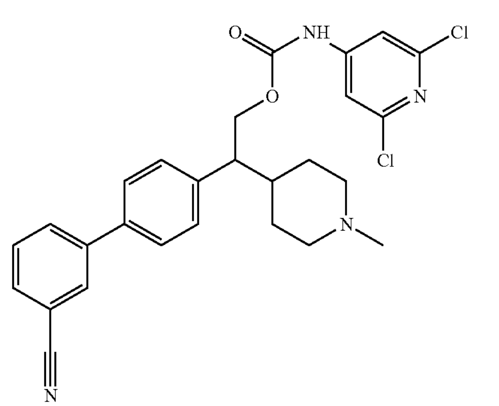 | 509.1514 | 5.36; 506.1 | 7.75–7.85 (m, 2H), 7.45–7.65 (m, 4H), 7.32 (s, 2H), 7.24 (d, J=8.1 Hz, 2H), 4.50–4.60 (m, 1H), 4.35–4.45 (m, 1H), 2.70–2.95 (m, 3H), 2.22 (s, 3H), 1.75–2.00 (m, 3H), 1.20–1.70 (m, 4H) |

TABLE 2-continued

| Compound | Structure | HRMS (M + H+) | LCMS (retention time; MS | NMR |
|---|---|---|---|---|
| 5f | 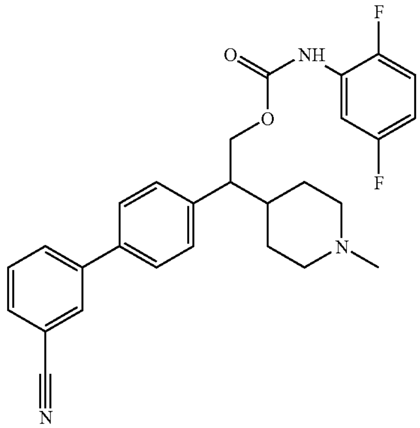 | 476.2146 | 5.31; 476.1 | |
| 5g | 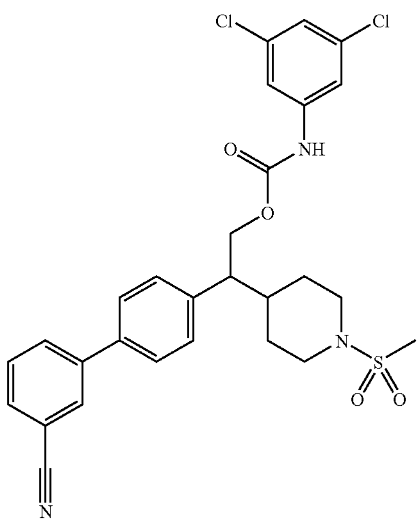 | non-ionizable | non-ionizable | 7.85 (s, 1H), 7.80 (d, J=7.8 Hz, 1H), 7.62 (d, J=7.8 Hz, 1H), 7.50–7.60 (m, 3H), 7.20–7.35 (m, 3H), 7.03 (s, 1H), 6.59 (br s, 1H), 4.55–4.65 (m, 1H), 4.40–4.50 (m, 1H), 3.89 (br d, 1H), 3.74 (br d, 1H), 3.14 (s, 2H), 2.85–2.95 (m, 1H), 2.75 (s, 3H), 2.50–2.70 (m, 1H), 2.00–2.10 (m, 1H), 1.70–1.90 (m, 1H), 1.45–1.65 (m, 1H), 1.45–1.65 (m, 1H), 1.20-1.40 |
| 5h | 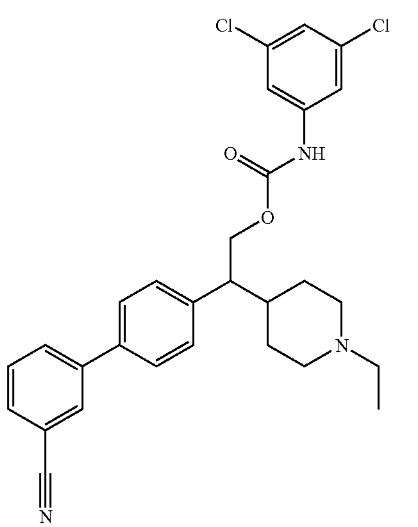 | 522.1709 | 6.36; 522.1 | |

TABLE 2-continued
| Compound | Structure | HRMS (M + H+) | LCMS (retention time; MS | NMR |
|---|---|---|---|---|
| 5i | 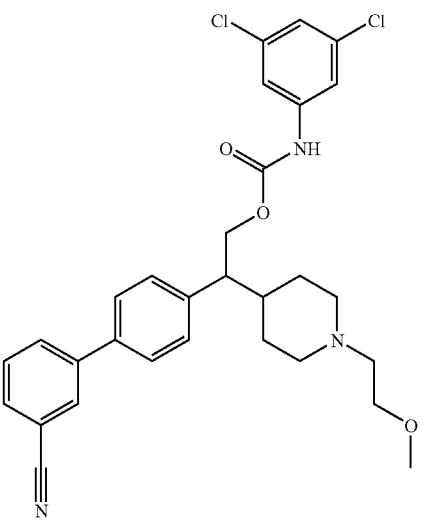 | 552.1829 | 6.26; 552.1 | |
| 5j | 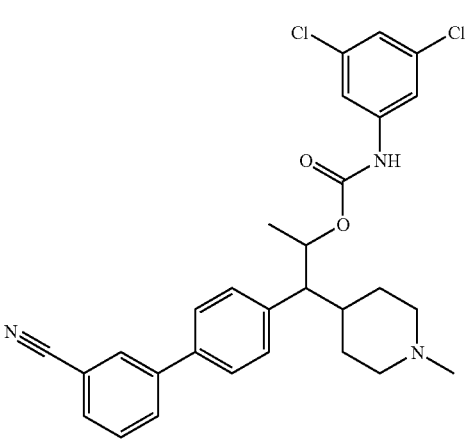 | 522.1715 | 5.91; 522.1 | 7.84 (s, 1H), 7.79 (d, J=8.4 Hz, 1H), 7.45–7.65 (m, 4H), 7.25–7.40 (m, 3H), 7.05 (s, 1H), 6.76 (s, 1H), 5.40–5.50 (m, 1H), 2.95 (br d, 1H), 2.79 (br d, 1H), 2.45–2.55 (m, 1H), 2.25 (s, 3H), 1.70–2.10 (m, 4H), 1.10–1.50 (m, 4H), 1.14 (d, J=6.6 Hz, 3H) |
| 5k | 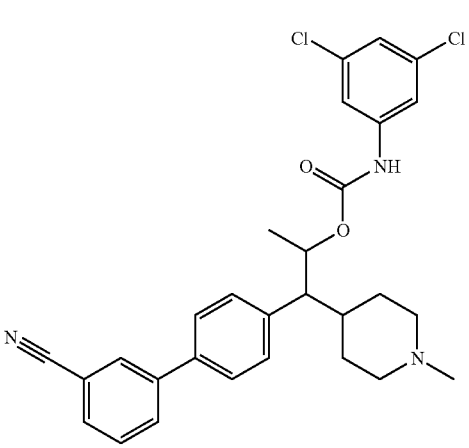 | 522.1715 | 5.71; 522.1 | 7.84 (s, 1H), 7.79 (d, J=7.8 Hz, 1H), 7.45–7.65 (m, 4H), 7.36 (s, 1H), 7.21 (d, J=8.1 Hz, 2H), 7.04 (s, 1H), 6.88 (s, 1H), 5.35–5.50 (m, 1H), 2.75–2.95 (m, 2H), 2.22 (s, 3H), 1.55–2.05 (m, 6H), 1.20–1.45 (m, 2H), 1.17 (d, J=6.6 Hz, 3H) |

TABLE 2-continued
| Compound | Structure | HRMS (M + H⁺) | LCMS (retention time; MS | NMR |
|---|---|---|---|---|
| 5l | 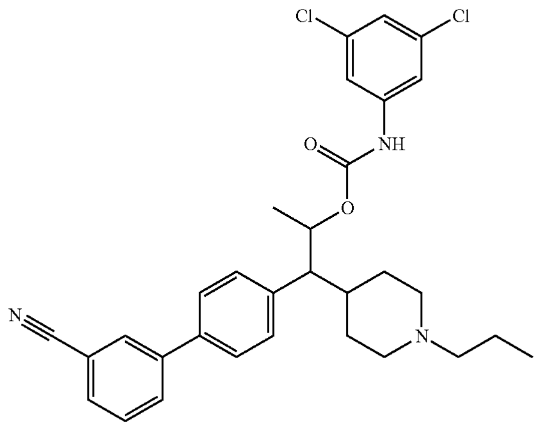 | 520.2026 | 5.81; 550.1 | |
| 5m | 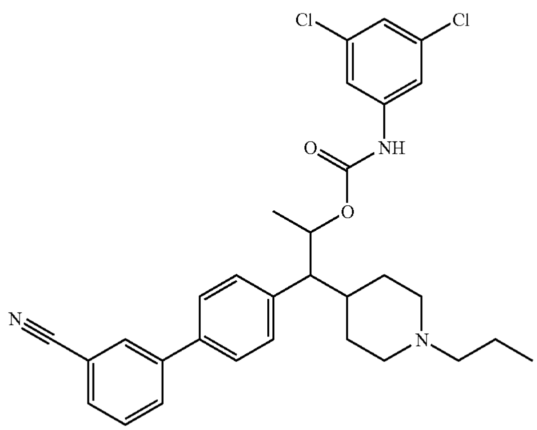 | 550.2026 | 5.86; 550.1 | |
Example 2
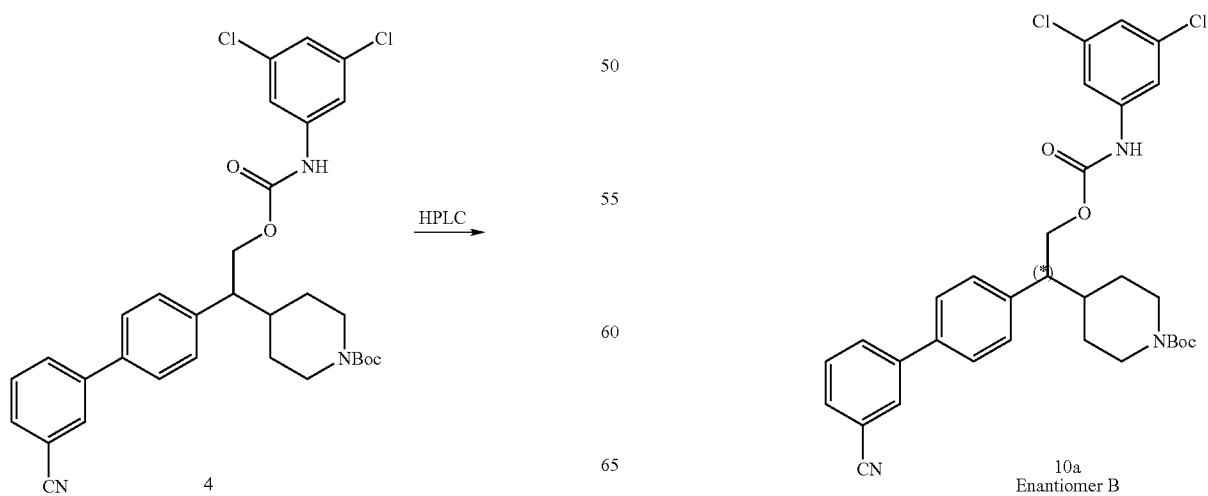

Compound 6

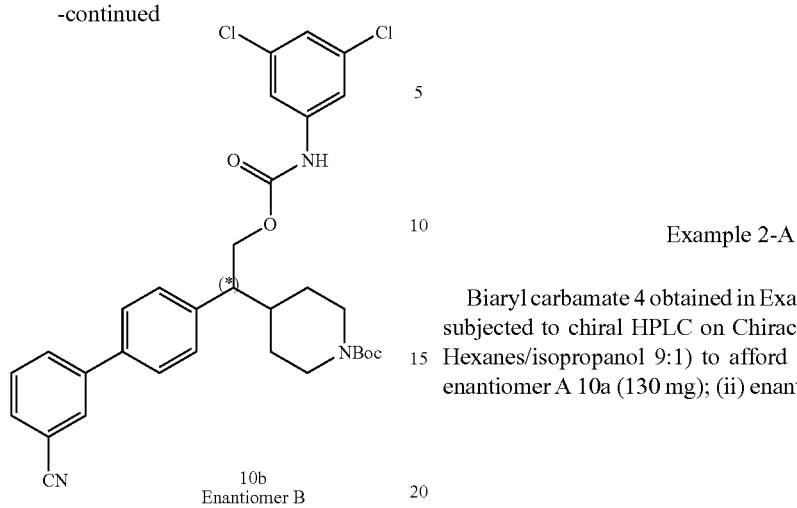

Example 2-A

Biaryl carbamate 4 obtained in Example 1-D (260 mg) was subjected to chiral HPLC on Chiracel AD column (eluting Hexanes/isopropanol 9:1) to afford in order of elution: (i) enantiomer A 10a (130 mg); (ii) enantiomer B 10b (130 mg).

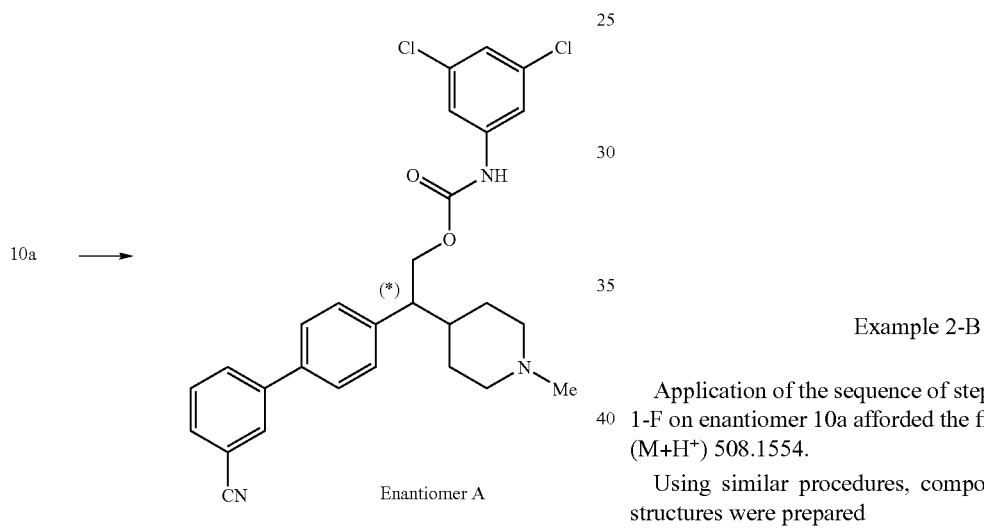

Example 2-B

Application of the sequence of steps from example 1-E to 1-F on enantiomer 10a afforded the final compound: HRMS (M+H$^+$) 508.1554.

Using similar procedures, compounds of the following structures were prepared

TABLE 3

| Compound | Structure | HRMS(M + H$^+$) |
|---|---|---|
| 7 | Enantiomer B | 508.1554 |

Example 3

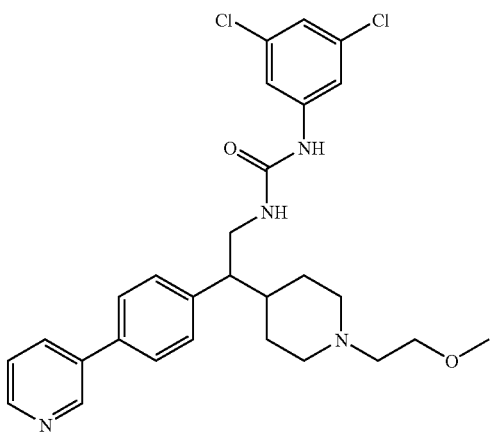

This compound (compound 8) was prepared according to Scheme 2.

Example 3-A

To a solution of bromo alcohol 3 (15.4 g; 41.5 mmol) and triphenylphosphine (11.0 g; 42 mmol) in THF (120 ml) in a water bath was added diethylazodicarboxylate (6.61 ml; 42 mmol) followed slowly by diphenylphosphoryl azide (9.03 ml; 42 mmol) and the mixture was stirred overnight at room temperature. Water (30 ml) followed by triphenylphosphine (22 g; 84 mmol) were then added and the reaction was refluxed under nitrogen overnight. THF solvent was evaporated, the resulting mixture was diluted with 1N NaOH and extracted with $CH_2Cl_2$. Combined organic layers were dried over $Na_2SO_4$, concentrated, and the residue was subjected to flash-chromatography over silica gel (eluting $CH_2Cl_2$/ MeOH/$NH_4OH$ 95:5:0 to 90:10:1) to give 8.1 g (51%) of bromo amine 5.

Example 3-B

A solution of bromo amine 5 (4.6 g; 10.4 mmol), 3,5-dichlorophenyl isocyanate (2.35 g; 12.5 mmol) and triethylamine (0.7 mL; 5.2 mmol) in THF (25 ml) was stirred overnight at room temperature. The mixture was diluted with 0.1 N NaOH, extracted with $CH_2Cl_2$ and dried over $Na_2SO_4$. Concentration of the solvents followed by purification flash-chromatography over silica gel (eluting Hexanes/AcOEt 8:2 to 1:1) provided 3.2 g (54%) of bromo urea.

Example 3-C

A mixture of bromo urea (1.4 g; 2.40 mmol), 3-pyridylboronic acid (0.45 g; 3.6 mmol), $Pd(PPh_3)_4$ (0.56 g) and $Na_2CO_3$ (1.0 g) in DME (5 ml) and water (5 ml) was heated at 75° C. overnight. The cooled solution was diluted with 0.1 N NaOH and extracted with $CH_2Cl_2$. Combined organic layers were dried over $Na_2SO_4$, concentrated and the crude was subjected to flash-chromatography over silica gel (eluting Hexanes/AcOEt 1:1 to AcOEt) to provide 1.10 (85%) of biaryl urea 6.

Example 3-D

Removal of the Boc-protecting group in biaryl urea 6 (1.10 g) proceeded as in Example 1-E to afford 0.95 g of biaryl urea amine.

Example 3-E

A solution of biaryl urea amine (100 mg; 0.21 mmol), 2-bromoethyl methyl ether (32 mg; 0.23 mmol) and potassium carbonate (60 mg; 0.42 mmol) was heated in $CH_3CN$ at 40° C. overnight. The cooled solution was diluted with 0.1 N NaOH and extracted with $CH_2Cl_2$, then AcOEt. Combined organic layers were dried over $Na_2SO_4$, concentrated and the crude was purified by preparative chromatography over silica gel (eluting $CH_2Cl_2$/MeOH/$NH_4OH$ 9:1:0.2) to give 39.2 mg of hydrochloride salt Ib, after trituration in $Et_2O$: $^1$H-NMR (free base, 300 MHz, $CDCl_3$) δ 8.54 (s, 1H), 8.46 (s, 1H), 8.43 (d, J=4.2 Hz, 1H), 7.75 (br d, 1H), 7.25-7.40 (m, 3H), 7.21 (s, 1 H), 7.10 (d, J=8.1 Hz, 2H), 6.87 (s, 1H), 5.43 (m, 1H), 3.91 (m, 1H), 3.46 (t, J=5.4 Hz, 2H), 3.25-3.40 (m, 1H), 3.29 (s, 3H), 3.00 (br d, 1H), 2.82 (br d, 1H), 2.46-2.65 (m, 1H), 2.51 (t, J=5.4 Hz, 2H), 1.80-2.10 (m, 3H), 1.10-1.60 (m, 4H); HRMS (M+H$^+$) 527.1979.

Using similar procedures, compounds of the following structures were prepared:

TABLE 4

| Compound | Structure | HRMS (M + H$^+$) | $^1$H-NMR (free base, 300 MHz, $CDCl_3$) | LCMS (retention time; MS) |
|---|---|---|---|---|
| 9 | 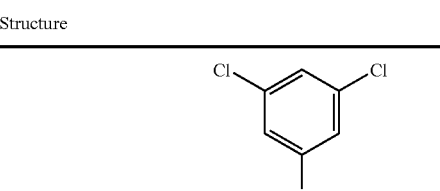 | 581.2084 | 8.40 (s, 1H), 8.19 (d, J= 5.8 Hz, 1H), 7.87 (d, J= 5.8 Hz, 1H), 7.80 (d, J= 6.4 Hz, 1H), 7.55– 7.65 (m, 4H), 7.22 (d, J= 8.0 Hz, 2H), 6.95 (s, 1H), 3.84 (m, 1H), 3.43 (m, 1H), 3.18 (br d, 1H), 3.06 (br d, 1 H), 2.71 (m, 1H), 2.56 (br s, 1H), 1.40–2.10 (m, 15H) | |

TABLE 4-continued

| Compound | Structure | HRMS (M + H+) | 1H-NMR (free base, 300 MHz, CDCl3) | LCMS (retention time; MS) |
|---|---|---|---|---|
| 10 | 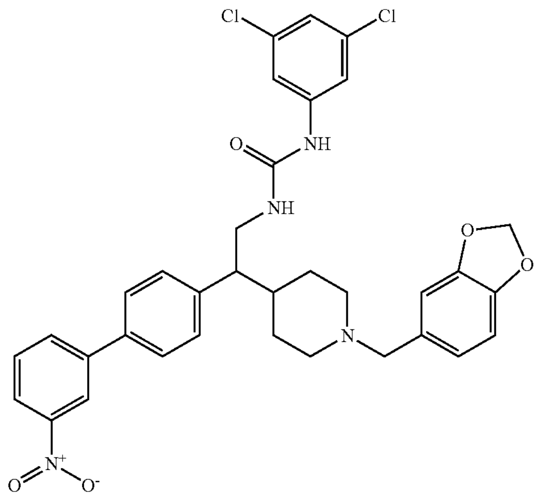 | 647.1820 | | |
| 11 | 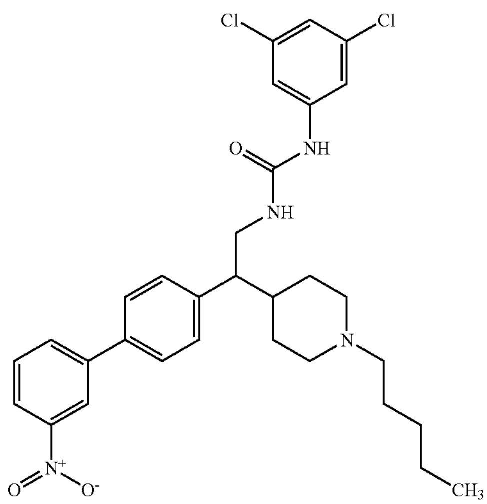 | 583.2236 | | |
| 12 | 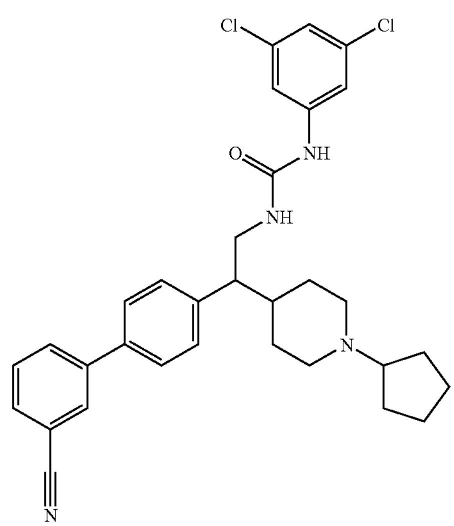 | 561.2188 | | |

TABLE 4-continued

| Compound | Structure | HRMS (M + H+) | ¹H-NMR (free base, 300 MHz, CDCl₃) | LCMS (retention time; MS) |
|---|---|---|---|---|
| 13 | 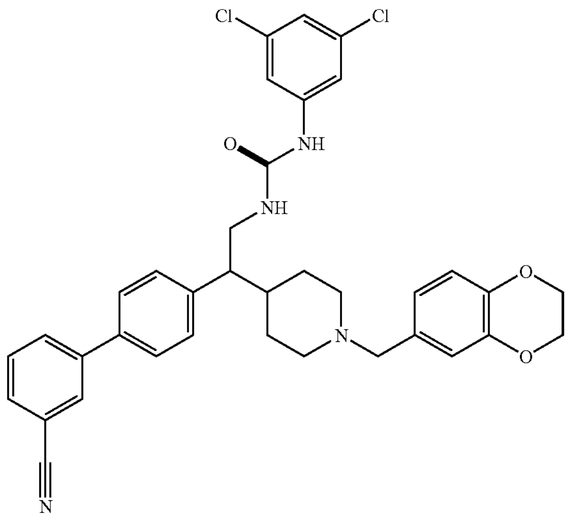 | 641.2083 | | |
| 14 | 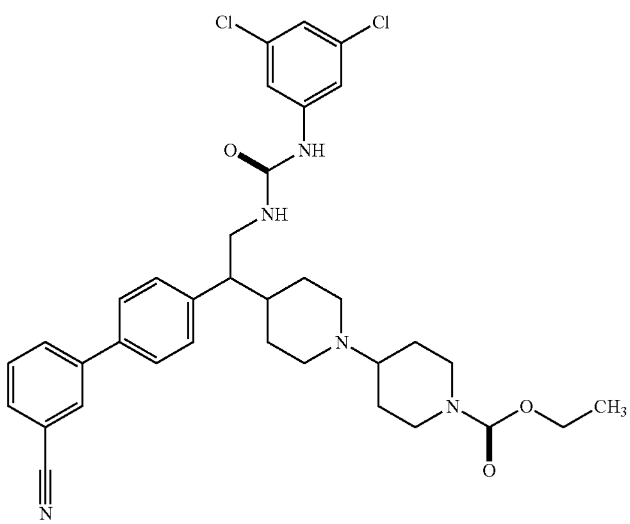 | 648.2503 | 7.78 (s, 1 H), 7.77 (d, J=7.5 Hz, 1H), 7.45–7.65 (m, 4H), 7.21 (d, J=7.8 Hz, 2H), 6.93 (s, 1H), 5.18 (br s, 1H), 4.20 (br d, 2H), 4.08 (q, J=7.2 Hz, 2H), 3.82 (m, 1H), 3.40 (m, 1H), 3.03 (br d, 1H), 2.92 (br d, 1H), 2.45–2.80 (m, 4H), 2.10–2.30 (m, 2H), 1.98 (br s, 1H), 1.83 (br d, 2H), 1.30–1.65 (m, 6H), 2.24 (t, J=7.2 Hz, 3H) | |
| 15 | 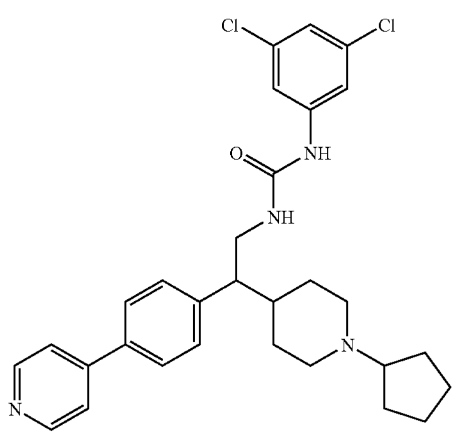 | 537.2186 | | |

TABLE 4-continued

| Compound | Structure | HRMS (M + H+) | ¹H-NMR (free base, 300 MHz, CDCl₃) | LCMS (retention time; MS) |
| --- | --- | --- | --- | --- |
| 16 | 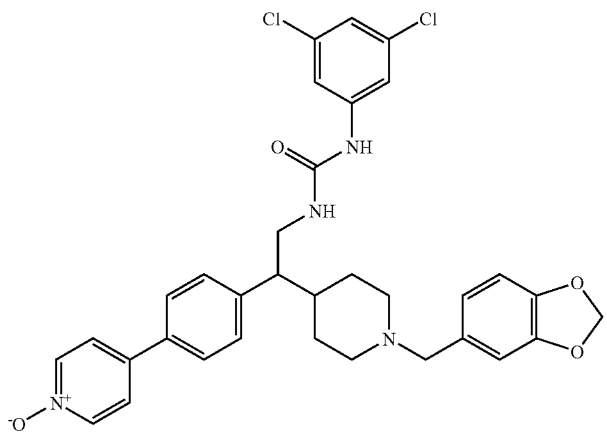 | 619.1879 | | |
| 17 | 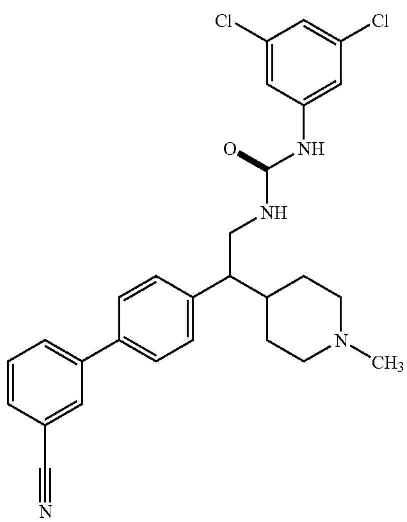 | 507.1719 | | |
| 18 | 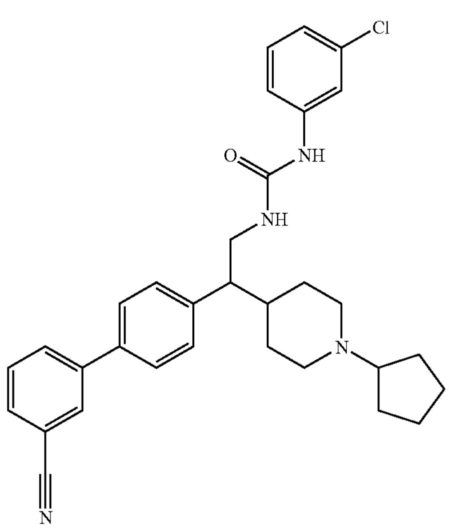 | 527.2576 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 19 | 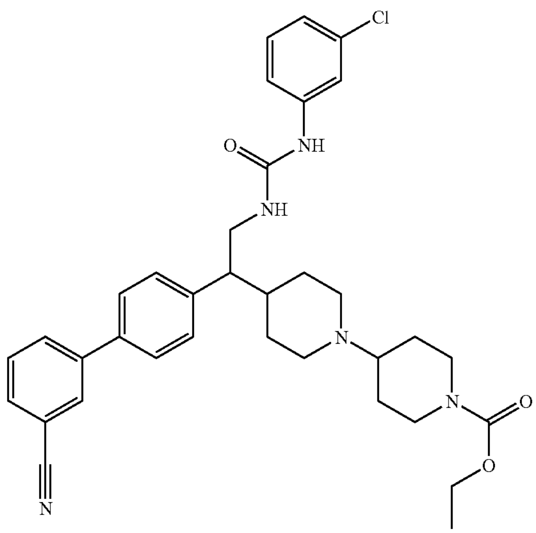 | 614.2887 | | |
| 20 | 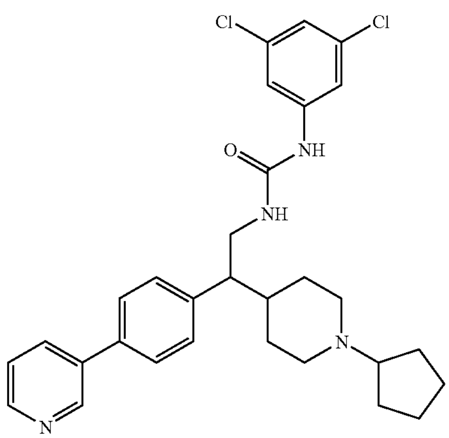 | 537.2181 | | |
| 21 | 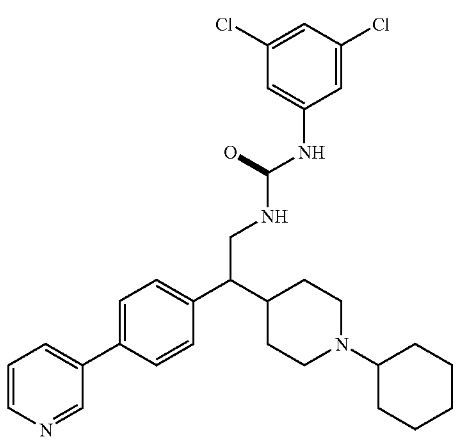 | 551.2347 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 22 | 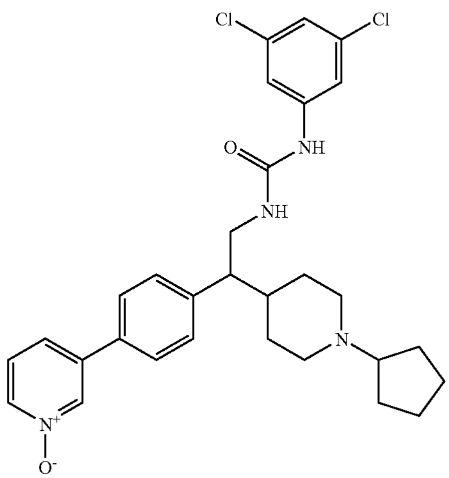 | 553.2145 | | |
| 23 | 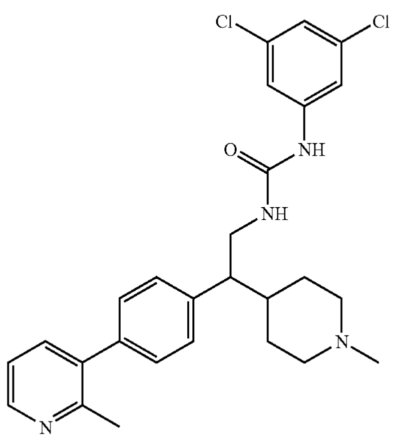 | 497.1875 | 8.49 (s, 1H), 8.44 (br s, 1H), 7.49 (d, J= 5.7 Hz, 1H), 7.20–7.35 (m, 2H), 7.13 (d, J=6 Hz, 2H), 7.07 (d, J=6.0 Hz, 2H), 6.91 (s, 1H), 5.47 (br s, 1H), 3.81 (m, 1H), 3.39 (m, 1H), 2.98 (br d, 1H), 2.88 (br d, 1H), 2.60 (m, 1H), 2.32 (s, 3H), 2.29 (s, 3H), 1.90–2.15 (m, 3H), 1.30–1.65 (m, 4H) | |
| 24 | 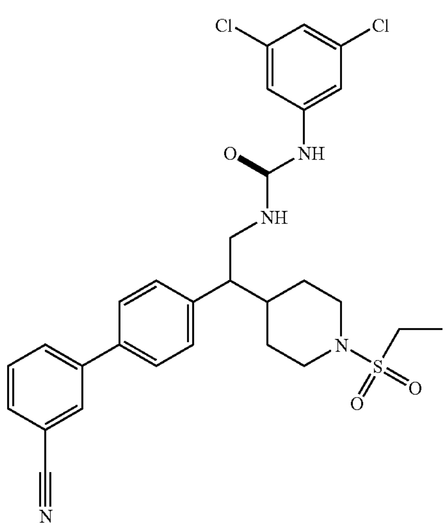 | 585.1498 | | |

TABLE 4-continued
| Compound | Structure | HRMS (M + H+) | 1H-NMR (free base, 300 MHz, CDCl3) | LCMS (retention time; MS) |
|---|---|---|---|---|
| 25 | 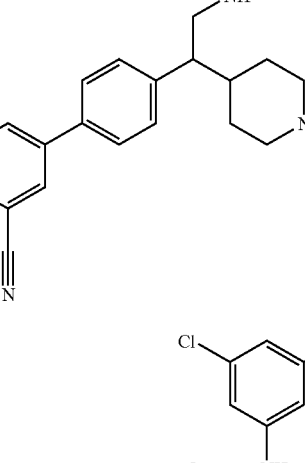 | 493.1564 | | |
| 26 | 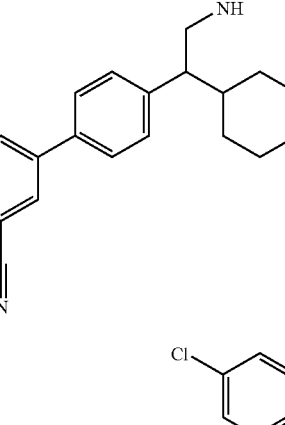 | 547.2030 | 7.73 (s, 1H), 7.70 (d, J=7.8 Hz, 1H), 7.58 (m, 1H), 7.40–7.55 (m, 3H), 7.15–7.30 (m, 4H), 6.92 (s, 1H), 5.01 (br s, 1H), 3.89 (m, 1H), 3.34 (m, 1H), 3.12 (br d, 1H), 3.00 (br d, 1H), 2.63 (m, 1H), 2.22 (d, J= 6.3 Hz, 2H), 1.80–2.05 (m, 3H), 1.15–1.65 (m, 4H), 0.83 (m, 1H), 0.49 (d, J=8.1 Hz, 2H), 0.08 (d, J=4.8 Hz, 2H) | |
| 27 | 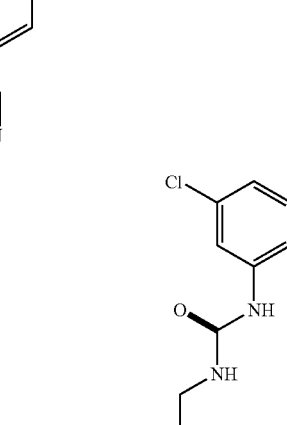 | 584.1982 | | |

TABLE 4-continued
| Compound | Structure | HRMS (M + H+) | 1H-NMR (free base, 300 MHz, CDCl3) | LCMS (retention time; MS) |
|---|---|---|---|---|
| 28 | 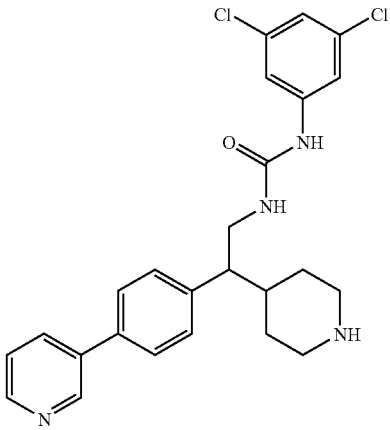 | 469.1554 | | |
| 29 | 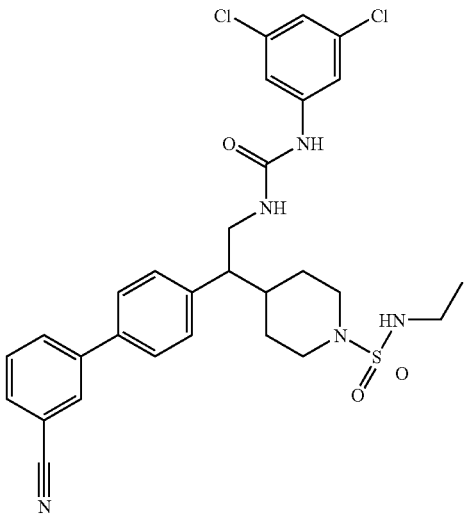 | 600.1601 | 7.65–7.75 (m, 2H), 7.57 (m, 1H), 7.40–7.50 (m, 3H), 7.10–7.25 (m, 4H), 6.92 (s, 1H), 5.05 (br s, 1H), 4.30 (br s, 1H), 3.92 (m, 1H), 3.72 (br d, 1H), 3.58 (br d, 1H), 3.30 (m, 1H), 3.04 (q, J=5.4 Hz, 2H), 2.50–2.75 (m, 3H), 1.96 (br d, 1H), 1.15–1.70 (m, 4H), 1.14 (t, J=5.4 Hz, 3H) | |
| 30 | 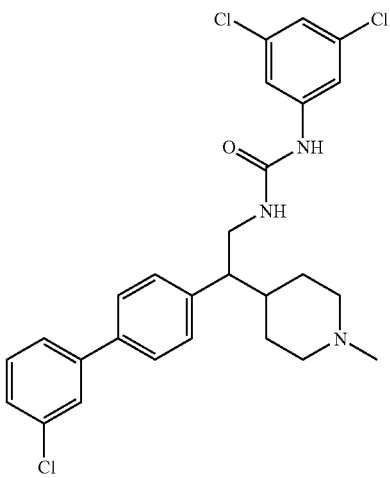 | 518.1345 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 31 | 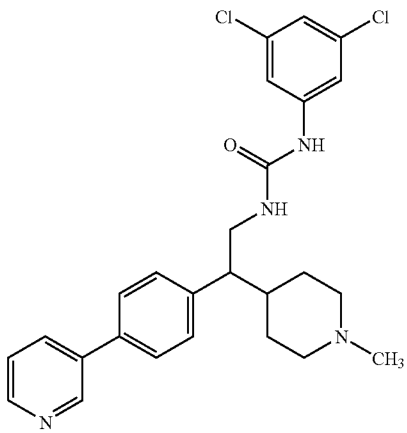 | 483.1719 | | |
| 32 | 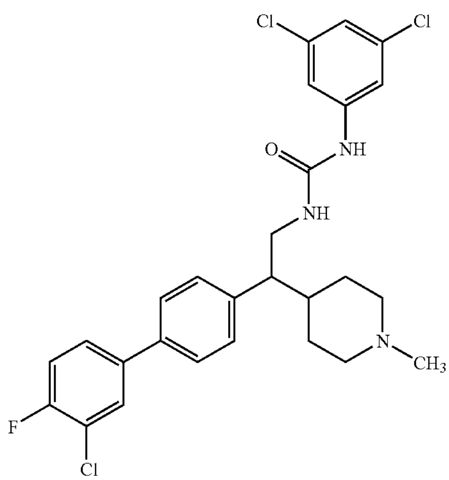 | 534.1287 | | |
| 33 | 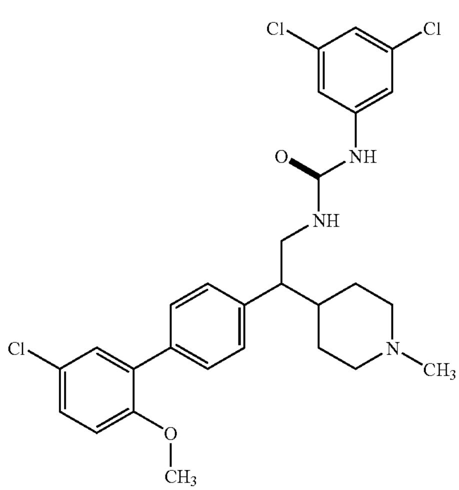 | 546.1482 | | |

TABLE 4-continued

| Compound | Structure | HRMS (M + H+) | 1H-NMR (free base, 300 MHz, CDCl3) | LCMS (retention time; MS) |
|---|---|---|---|---|
| 34 | 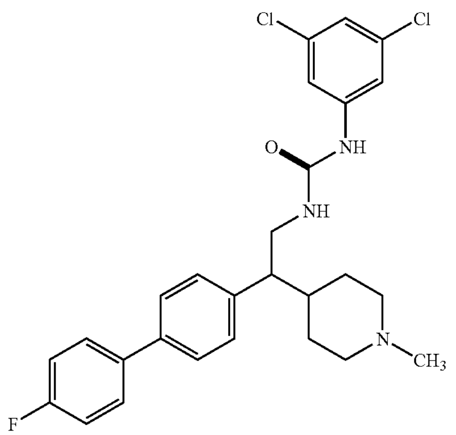 | 500.1659 | | |
| 35 | 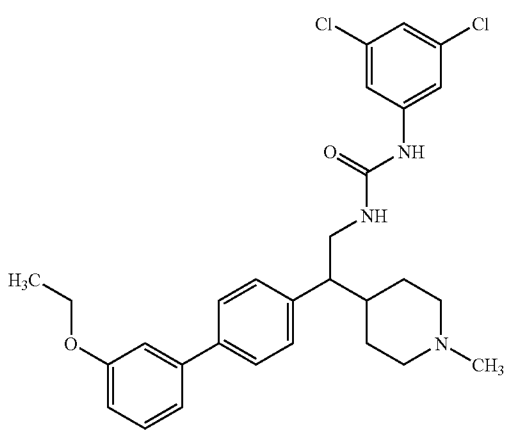 | 526.2022 | | |
| 36 | 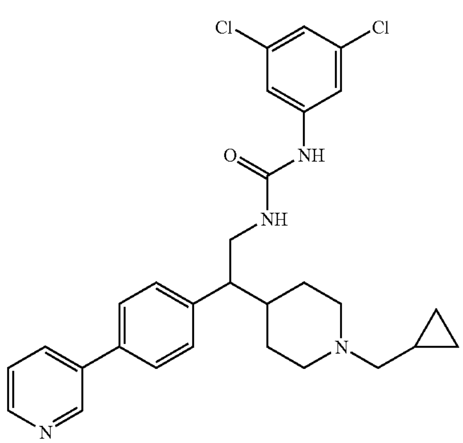 | 523.2029 | | |

TABLE 4-continued
| Compound | Structure | HRMS (M + H+) | 1H-NMR (free base, 300 MHz, CDCl3) | LCMS (retention time; MS) |
|---|---|---|---|---|
| 37 | 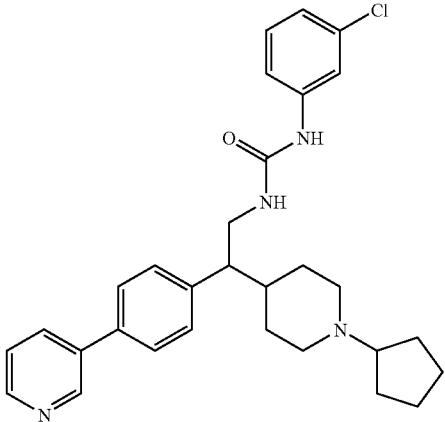 | 503.2583 | | |
| 38 | 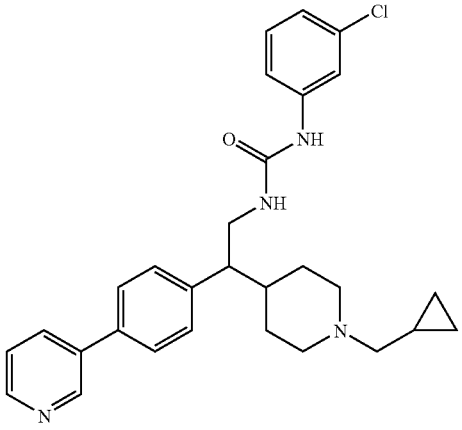 | 489.2428 | | |
| 39 | 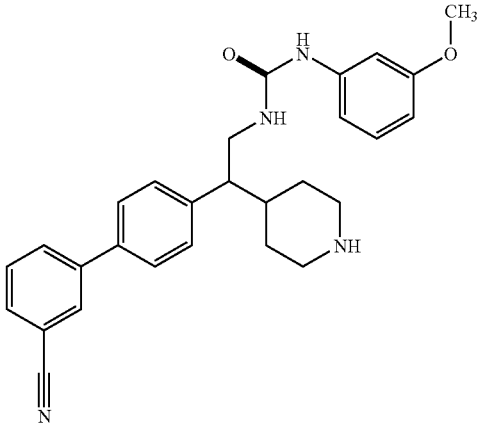 | 455.2430 | | |

TABLE 4-continued
| Compound | Structure | HRMS (M + H+) | 1H-NMR (free base, 300 MHz, CDCl3) | LCMS (retention time; MS) |
|---|---|---|---|---|
| 40 | 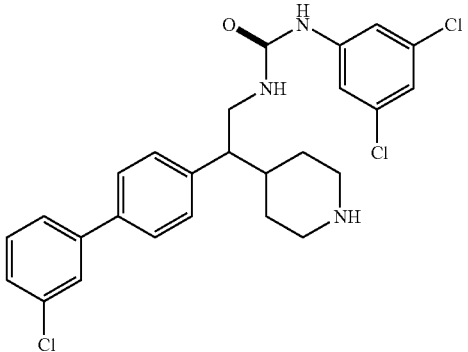 | 502.1231 | | |
| 41 | 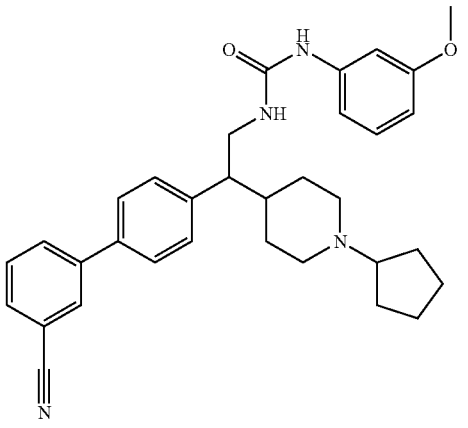 | 523.3075 | | |
| 42 | 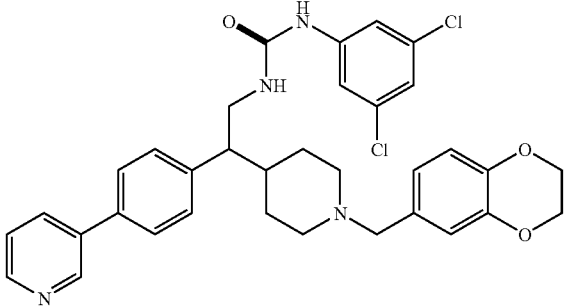 | 617.2084 | | |
| 43 | 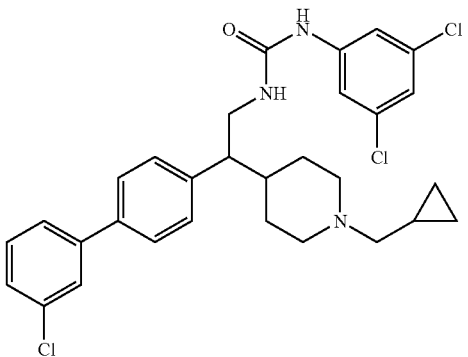 | 556.1683 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 44 | 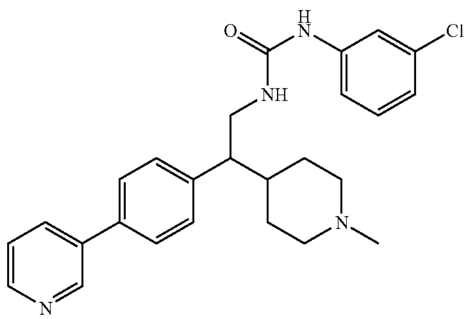 | 449.2106 | | |
| 45 | 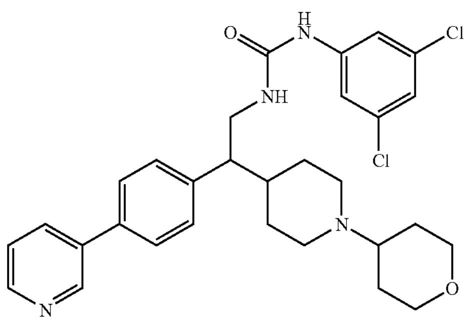 | 553.2145 | | |
| 46 | 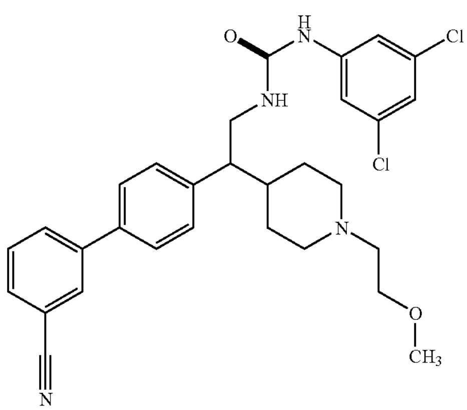 | 551.1987 | | |
| 47 | 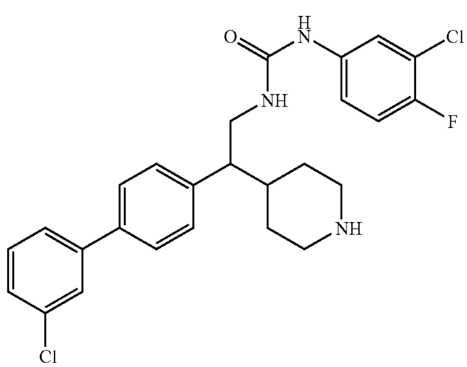 | 486.1509 | | |

TABLE 4-continued

| Compound | Structure | HRMS (M + H+) | 1H-NMR (free base, 300 MHz, CDCl3) | LCMS (retention time; MS) |
|---|---|---|---|---|
| 48 | 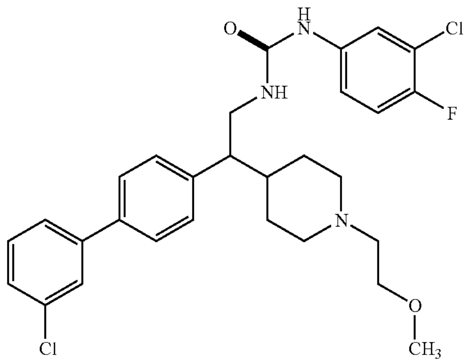 | 544.1939 | | |
| 49 | 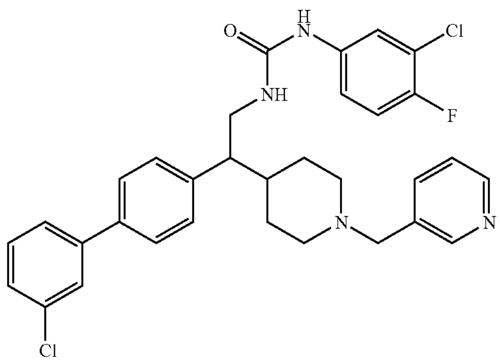 | 577.1927 | | |
| 50 | 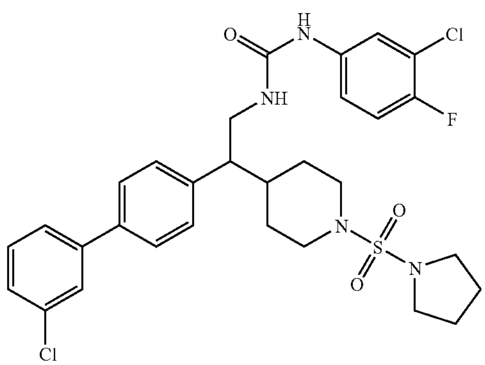 | 619.1704 | | |
| 51 | 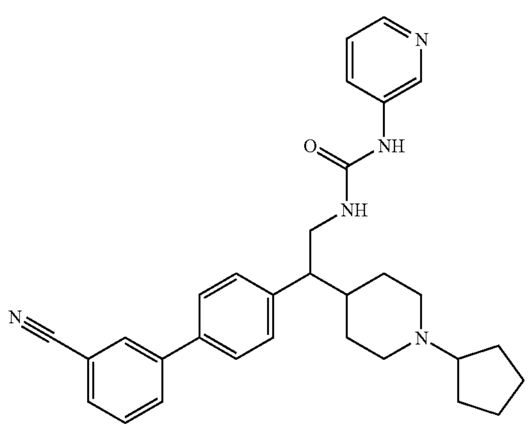 | 494.2916 | 8.43 (s, 1H), 8.15 (d, J=4.8 Hz, 1H), 8.06 (br s, 1H), 7.98 (d, J= 8.5 Hz, 1H), 7.70–7.80 (m, 2H), 7.50–7.65 (m, 2H), 7.46 (d, J=8.0 Hz, 2H), 7.23 (d, J=8.0 Hz, 2H), 7.17 (m, 1H), 5.90 (br s, 1H), 3.87 (m, 1H), 3.53 (m, 1H), 3.36 (br d, 1H), 3.22 (br d, 1H), 2.70–2.85 (m, 2H), 1.25–2.15 (m, 15H) | |

TABLE 4-continued
| Compound | Structure | HRMS (M + H+) | 1H-NMR (free base, 300 MHz, CDCl3) | LCMS (retention time; MS) |
|---|---|---|---|---|
| 52 | 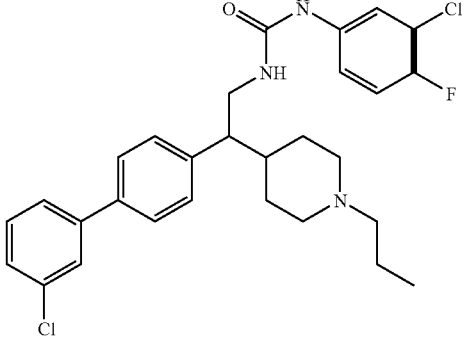 | 528.1979 | | |
| 53 | 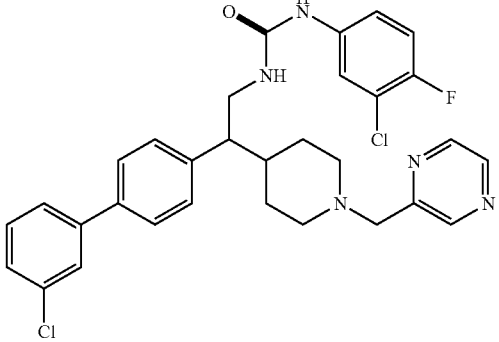 | 578.1899 | 8.60 (s, 1H), 8.46 (s, 1H), 8.41 (s, 1H), 7.47 (s, 1H), 7.25–7.45 (m, 6H), 7.11 (d, J=6.3 Hz, 2H), 7.03 (br s, 1H), 6.85–7.00 (m, 2H), 4.83 (br s, 1H), 3.82 (m, 1H), 3.62 (s, 2H), 3.24 (m, 1H), 2.90 (br d, 1H), 2.78 (br d, 1H), 2.57 (m, 1H), 2.10 (br t, 1H), 1.98 (br t, 1H), 1.86 (m, 1H), 1.15–1.60 (m, 4H) | |
| 54 | 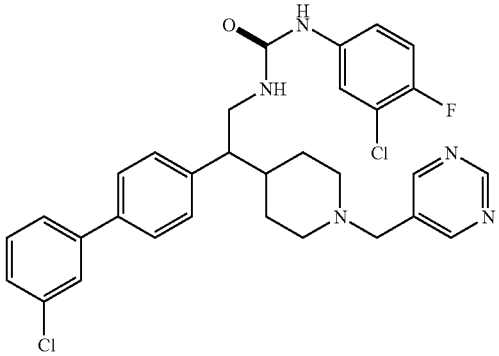 | 578.1893 | | |
| 55 | 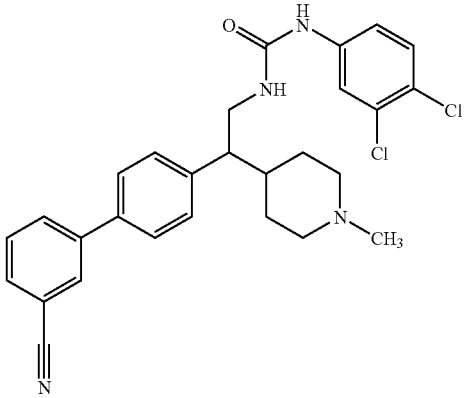 | 507.1724 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 56 | 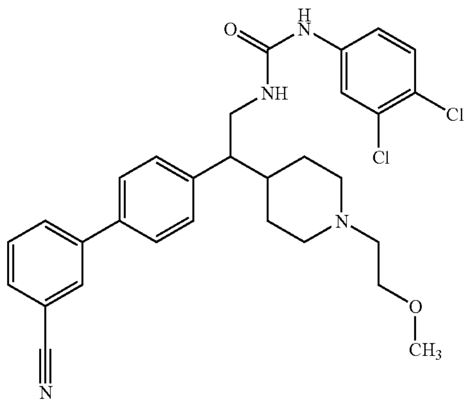 | 551.1987 | | |
| 57 | 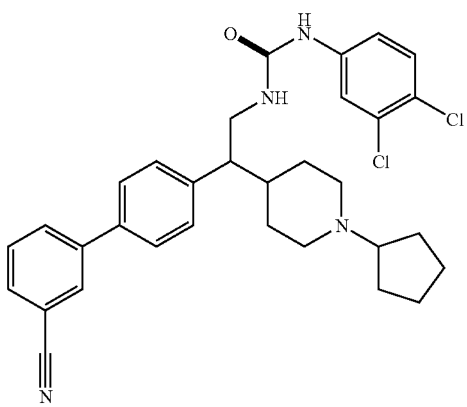 | 561.2183 | | |
| 58 | 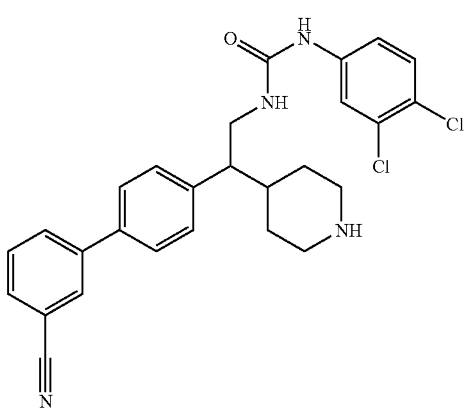 | 493.1554 | | |

TABLE 4-continued

| Compound | Structure | HRMS (M + H+) | 1H-NMR (free base, 300 MHz, CDCl3) | LCMS (retention time; MS) |
|---|---|---|---|---|
| 59 | 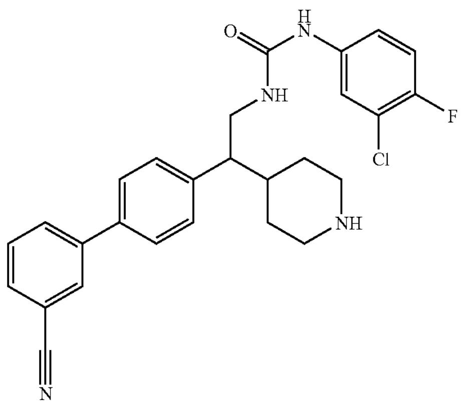 | 477.1849 | | |
| 60 | 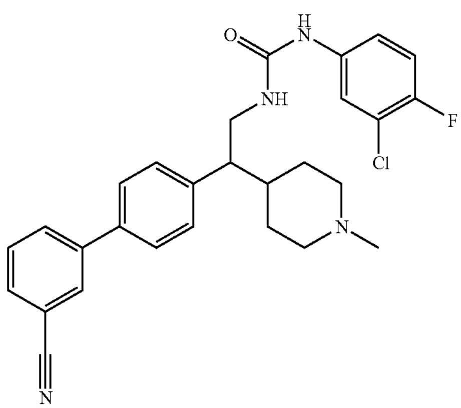 | 491.2020 | | |
| 61 | 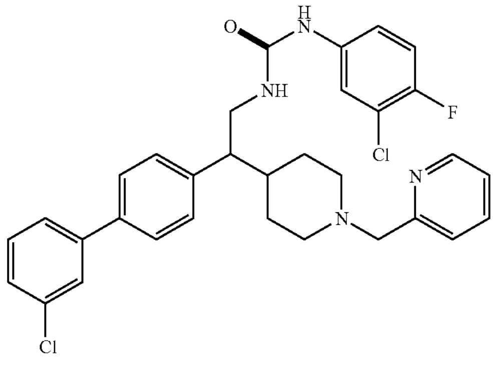 | 577.1944 | | |

TABLE 4-continued

| Compound | Structure | HRMS (M + H⁺) | ¹H-NMR (free base, 300 MHz, CDCl₃) | LCMS (retention time; MS) |
|---|---|---|---|---|
| 62 | 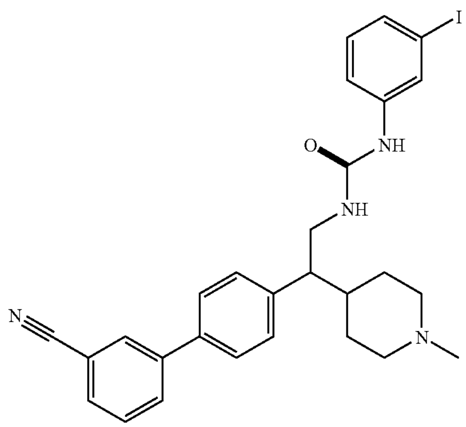 | 565.1466 | | |
| 63 | 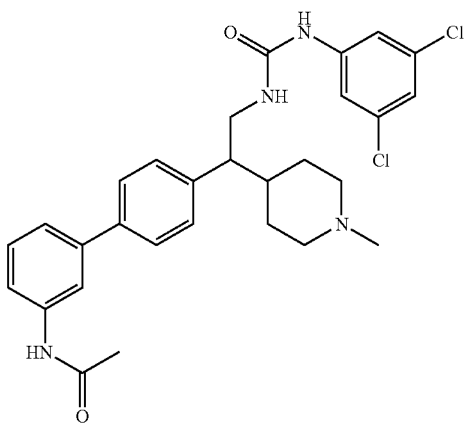 | 539.1985 | 8.83 (br s, 1H), 8.50 (s, 1H), 7.80 (s, 1H), 7.25–7.40 (m, 4H), 7.00–7.15 (m, 4H), 6.86 (s, 1H), 5.59 (d, 1H), 3.90 (m, 1H), 3.08 (br t, 1H), 2.96 (br d, 1H), 2.74 (br d, 1H), 2.48 (m, 1H), 2.17 (br s, 1H), 2.24 (s, 3H), 2.10 (s, 3H), 1.75–2.00 (m, 2H), 1.15–1.55 (m, 4H) | |
| 63a | 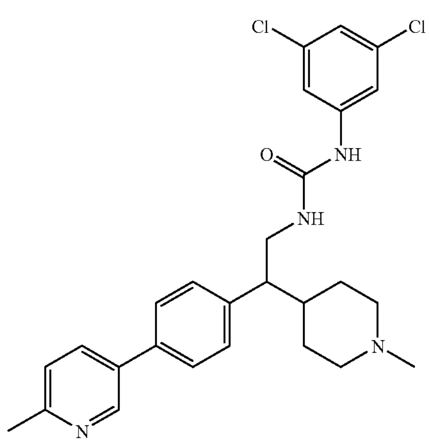 | | | 4.16; 497.1 |

TABLE 4-continued
| Compound | Structure | HRMS (M + H⁺) | ¹H-NMR (free base, 300 MHz, CDCl₃) | LCMS (retention time; MS) |
|---|---|---|---|---|
| 63b | 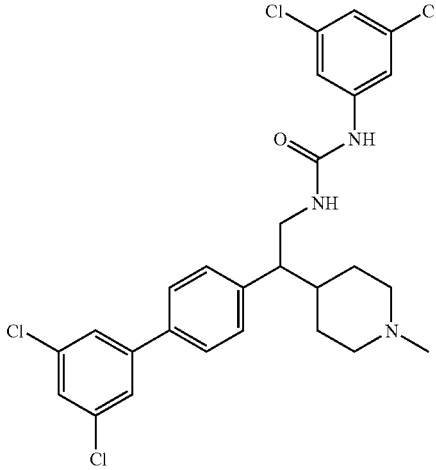 | | 7.44 (d, J=6.3 Hz, 2H), 7.38 (s, 2H), 7.32 (s, 1H), 7.15–7.25 (m, 4H), 6.94 (s, 1H), 5.05 (br s, 1H), 3.80–3.90 (m, 1H), 3.25–3.40 (m, 1H), 2.97 (br d, 1H), 2.87 (br d, 1H), 2.55–2.65 (m, 1H), 2.31 (s, 3H), 1.85–2.10 (m, 3H), 1.50–1.60 (m, 2H), 1.25–1.45 (m, 2H) | 5.86; 552.1 |
| 63c | 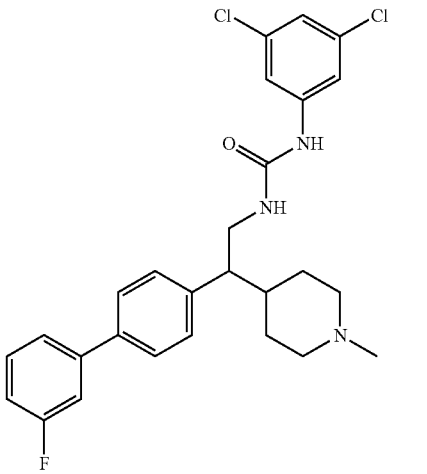 | | | 5.21; 500.1 |
| 63d | 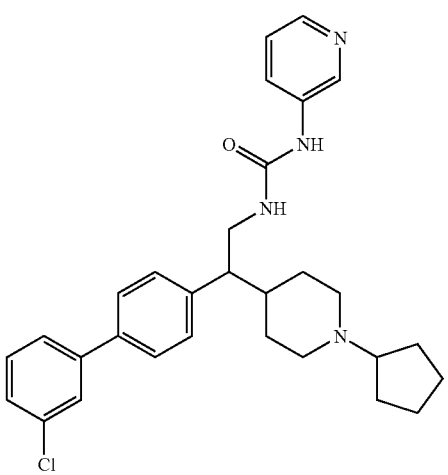 | 503.2583 | | 4.51; 503.1 |

TABLE 4-continued
| Compound | Structure | HRMS (M + H+) | 1H-NMR (free base, 300 MHz, CDCl3) | LCMS (retention time; MS) |
|---|---|---|---|---|
| 63e | 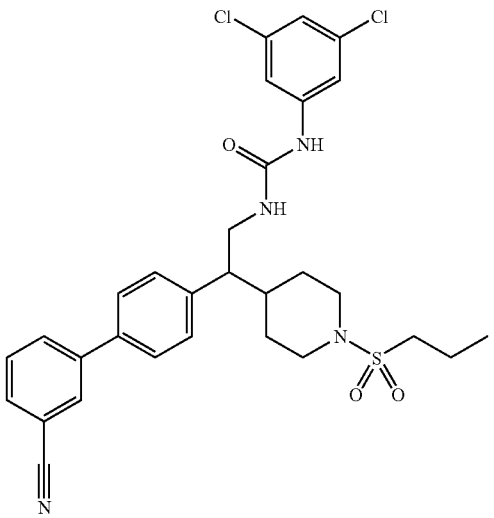 | 599.1642 | | 5.26; 599.1 |
| 63f | 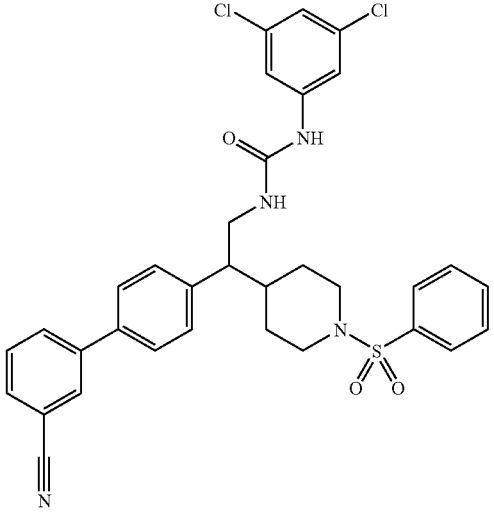 | 633.1500 | | 5.46; 633.1 |
| 63g | 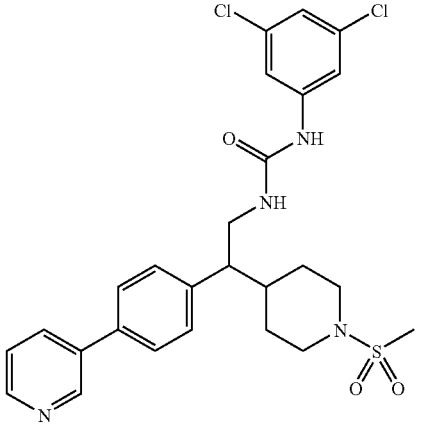 | 547.1343 | | 4.76; 547.1 |

TABLE 4-continued

| Compound | Structure | HRMS (M + H+) | ¹H-NMR (free base, 300 MHz, CDCl₃) | LCMS (retention time; MS) |
|---|---|---|---|---|
| 63h | 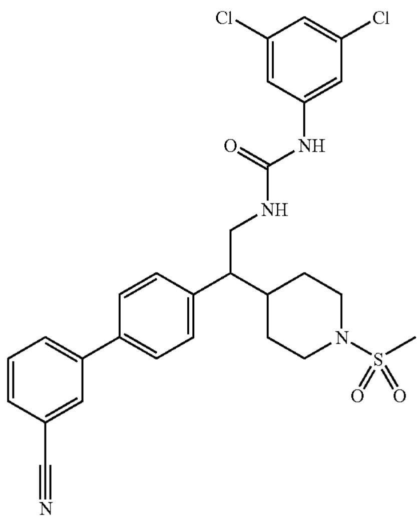 | non-ionizable | 7.76 (s, 1H), 7.73 (d, J=5.1 Hz, 1H), 7.45–7.60 (m, 4H), 7.23 (d, J=6.6 Hz, 2H), 7.17 (s, 2H), 6.94 (s, 1H), 6.84 (s, 1H), 4.84 (br s, 1H), 3.75–3.95 (m, 2H), 3.69 (br d, 1H), 3.30–3.40 (m, 1H), 2.73 (s, 3H), 2.45–2.75 (m, 3H), 1.95–2.05 (m, 1H), 1.55–1.75 (m, 1H), 1.15–1.55 (m, 3H) | non-ionizable |
| 63i | 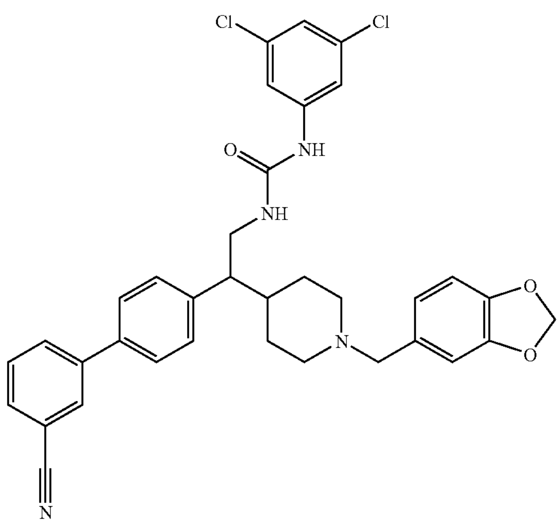 | | | 5.46; 627.1 |
| 63j | 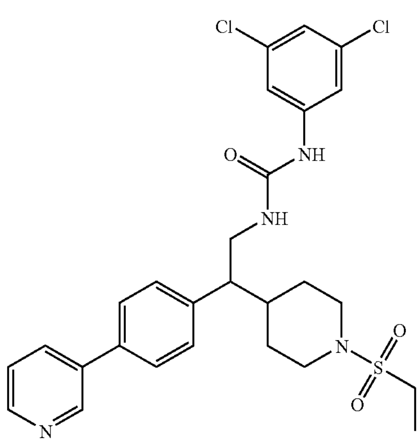 | 561.1499 | | 4.66; 561.1 |

TABLE 4-continued

| Compound | Structure | HRMS (M + H⁺) | ¹H-NMR (free base, 300 MHz, CDCl₃) | LCMS (retention time; MS) |
|---|---|---|---|---|
| 63k | 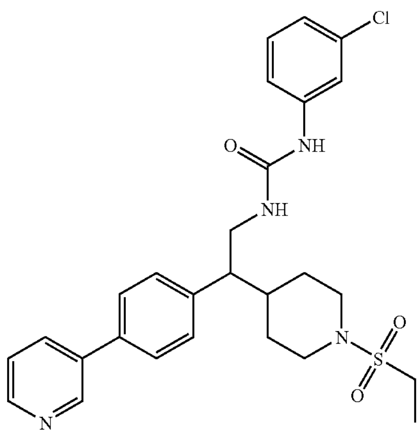 | 527.1876 | 8.58 (m, 1H), 7.85–7.95 (m, 1H), 7.35–7.65 (m, 4H), 7.30 (s, 1H), 7.19 (d, J= 8.4 Hz, 2H), 7.05– 7.15 (m, 2H), 6.85–6.95 (m, 1H), 5.26 (s, 1H), 3.80–4.00 (m, 2H), 3.69 (br d, 1H), 3.30– 3.45 (m, 1H), 2.89 (q, J=7.5 Hz, 2H), 2.55–2.85 (m, 3H), 1.95– 2.10 (m, 1H), 1.60– 1.75 (m, 1H), 1.05–1.50 (m, 6H) | 4.31; 527.1 |
| 63l | 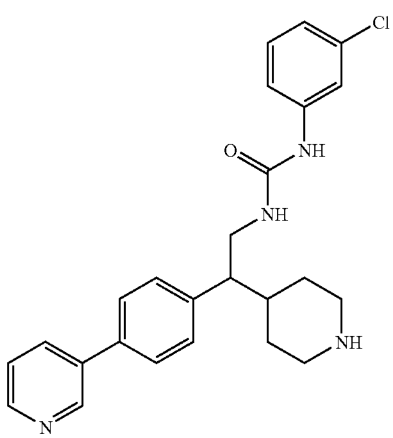 | 435.1941 | | 3.81; 435.1 |
| 63m | 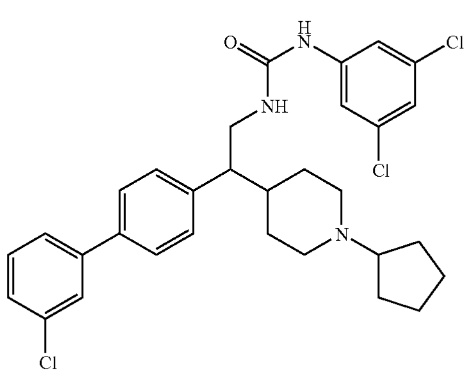 | 570.1851 | | 5.56; 570.1 |

TABLE 4-continued
| Compound | Structure | HRMS (M + H⁺) | ¹H-NMR (free base, 300 MHz, CDCl₃) | LCMS (retention time; MS) |
|---|---|---|---|---|
| 63n | 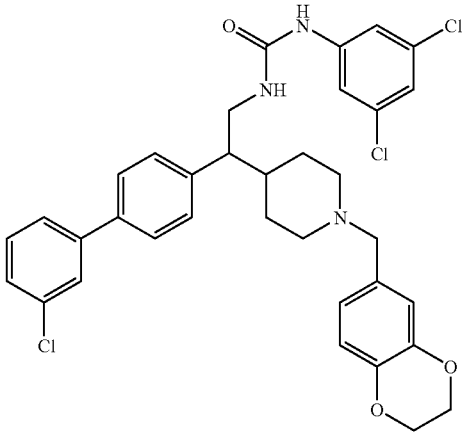 | 650.1735 | 7.49 (s, 1H), 7.45 (d, J=8.1 Hz, 1H), 7.25–7.40 (m, 4H), 7.05–7.20 (m, 4H), 7.04 (br s, 1H), 6.65–6.95 (m, 4H), 4.92 (br s, 1H), 4.22 (s, 4H), 3.70–3.85 (m, 1H), 3.36 (s, 2H), 3.20–3.35 (m, 1H), 2.90 (br d, 1H), 2.78 (br d, 1H), 2.50–2.60 (m, 1H), 1.70–2.00 (m, 3H), 1.10–1.60 (m, 4H) | 5.81; 650.2 |
| 63o | 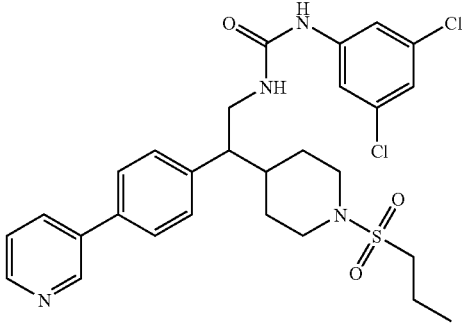 | 575.1656 | | 4.91; 575.1 |
| 63p | 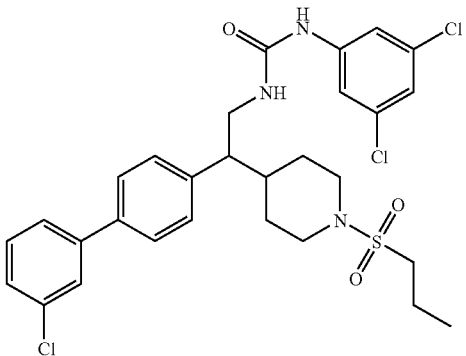 | 608.1304 | | 5.91; 608.1 |

TABLE 4-continued

| Compound | Structure | HRMS (M + H+) | ¹H-NMR (free base, 300 MHz, CDCl₃) | LCMS (retention time; MS) |
|---|---|---|---|---|
| 63q | 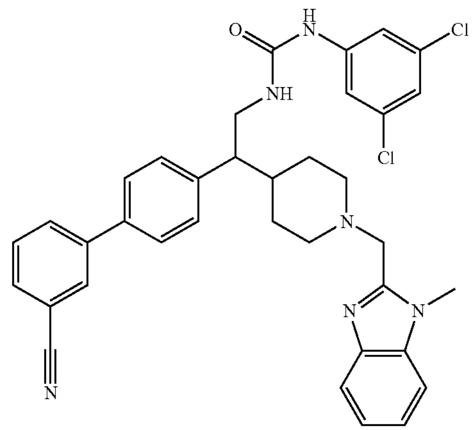 | 637.2248 | | 5.46; 637.2 |
| 63r | 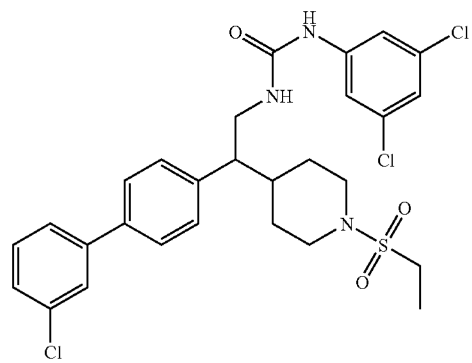 | 594.1127 | | 5.88; 594.1 |
| 63s | 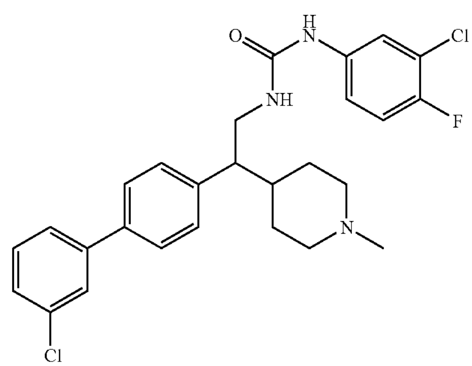 | 500.1672 | | 5.01; 500.1 |
| 63t | 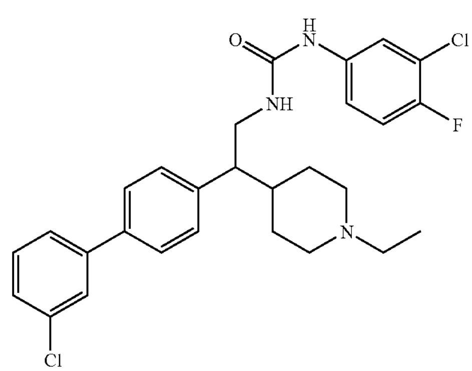 | 514.1823 | | 4.91; 514.1 |

TABLE 4-continued

| Compound | Structure | HRMS (M + H⁺) | ¹H-NMR (free base, 300 MHz, CDCl₃) | LCMS (retention time; MS) |
|---|---|---|---|---|
| 63u | 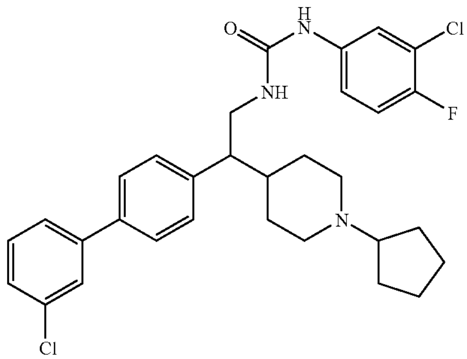 | 554.2151 | 7.25–7.55 (m, 7H), 7.13 (d, J=8.4 Hz, 2H), 7.00–7.10 (m, 1H), 6.93 (t, J=8.7 Hz, 1H), 5.34 (br s, 1H), 3.65–3.80 (m, 1H), 3.30–3.45 (m, 1H), 3.20 (br d, 1H), 3.10 (br d, 1H), 2.55–2.75 (m, 2H), 1.80–2.20 (m, 4H), 1.40–1.80 (m, 11H) | 5.06; 554.1 |
| 63v | 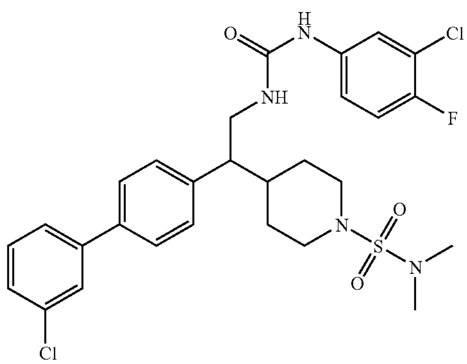 | 593.1548 | 7.25–7.55 (m, 7H), 7.15 (d, J=8.0 Hz, 2H), 6.85–7.05 (m, 3H), 4.87 (br s, 1H), 3.75–3.85 (m, 1H), 3.67 (br d, 1H), 3.54 (br d, 1H), 3.20–3.30 (m, 1H), 2.75 (s, 6H), 2.55–2.80 (m, 3H), 1.85–2.00 (m, 1H), 1.55–1.65 (m, 1H), 1.05–1.35 (m, 2H) | 5.46; 593.1 |
| 63w | 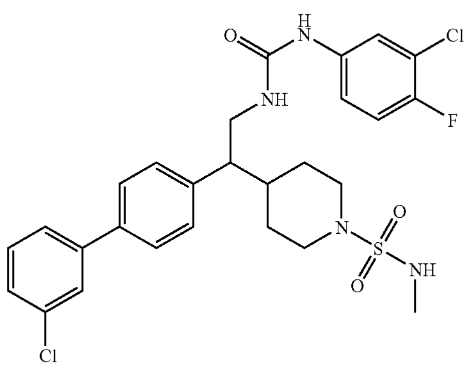 | 579.1394 | | |
| 63x | 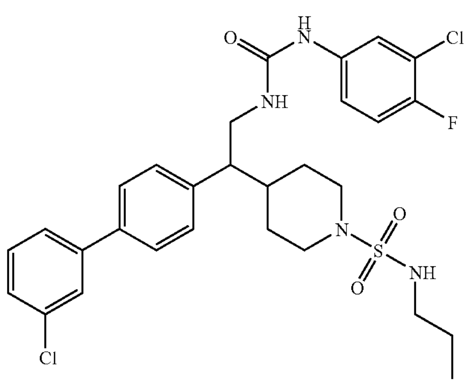 | 607.1707 | | 5.31; 607.1 |

TABLE 4-continued
| Compound | Structure | HRMS (M + H⁺) | ¹H-NMR (free base, 300 MHz, CDCl₃) | LCMS (retention time; MS) |
|---|---|---|---|---|
| 63y | 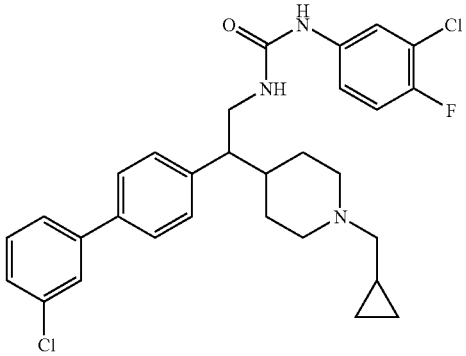 | 540.1992 | | 5.41; 540.1 |
| 63z | 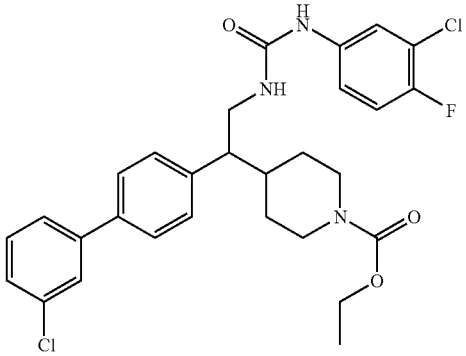 | 558.1733 | | 5.82; 558.1 |
| 63aa | 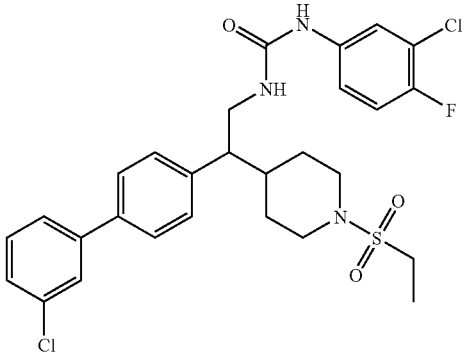 | 578.1446 | | 5.52; 578.1 |
| 63ab | 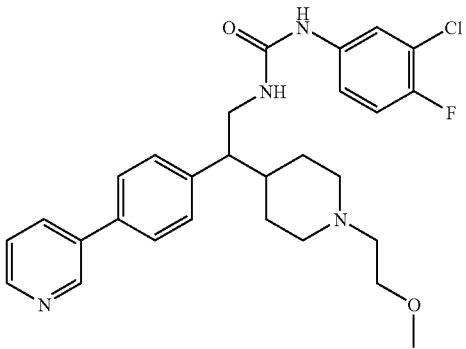 | 511.2283 | | 3.76; 511.1 |

TABLE 4-continued

| Compound | Structure | HRMS (M + H⁺) | ¹H-NMR (free base, 300 MHz, CDCl₃) | LCMS (retention time; MS) |
|---|---|---|---|---|
| 63ac | 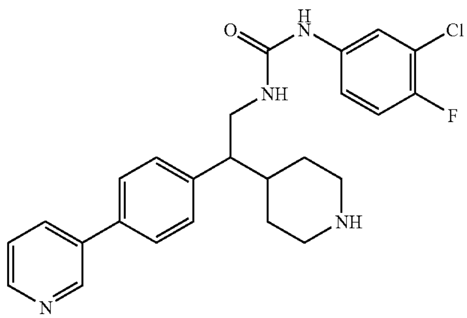 | 453.1853 | | 3.66; 453.1 |
| 63ad | 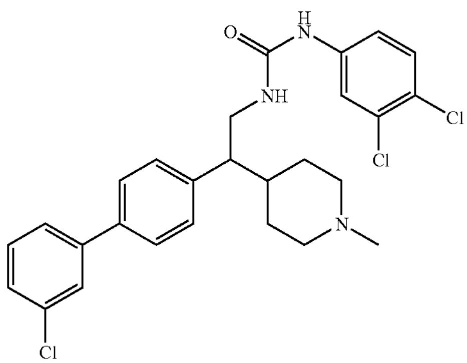 | 516.1382 | | 5.36; 516.1 |
| 63ae | 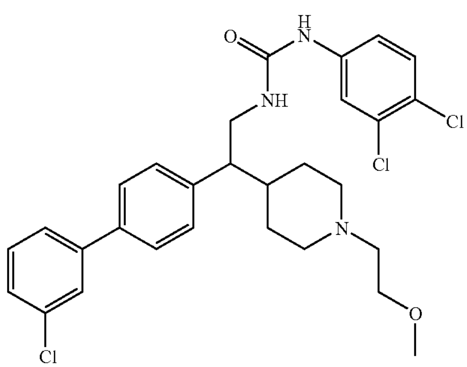 | 560.1645 | | 5.51; 560.1 |
| 63af | 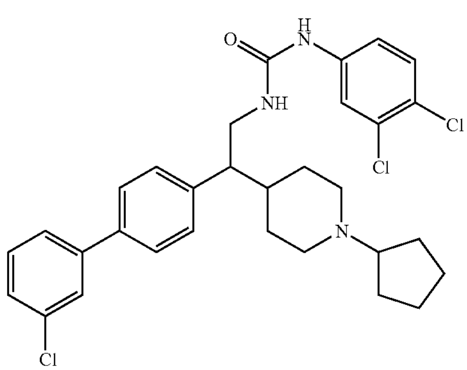 | 570.1851 | | 5.51; 570.1 |

TABLE 4-continued
| Compound | Structure | HRMS (M + H⁺) | ¹H-NMR (free base, 300 MHz, CDCl₃) | LCMS (retention time; MS) |
|---|---|---|---|---|
| 63ag | 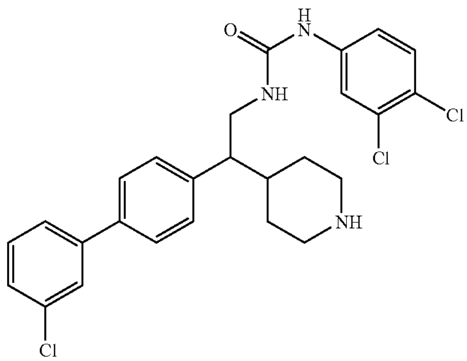 | 502.1224 | | 5.36; 502.1 |
| 63ah | 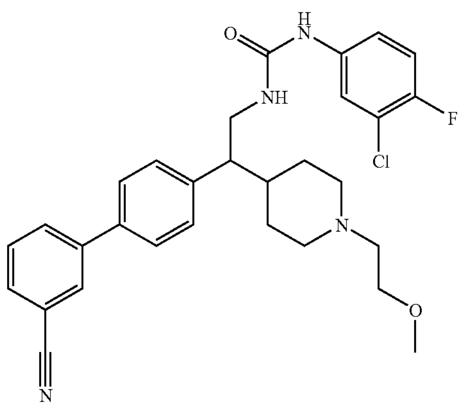 | 535.2277 | | 4.61; 535.1 |
Example 4
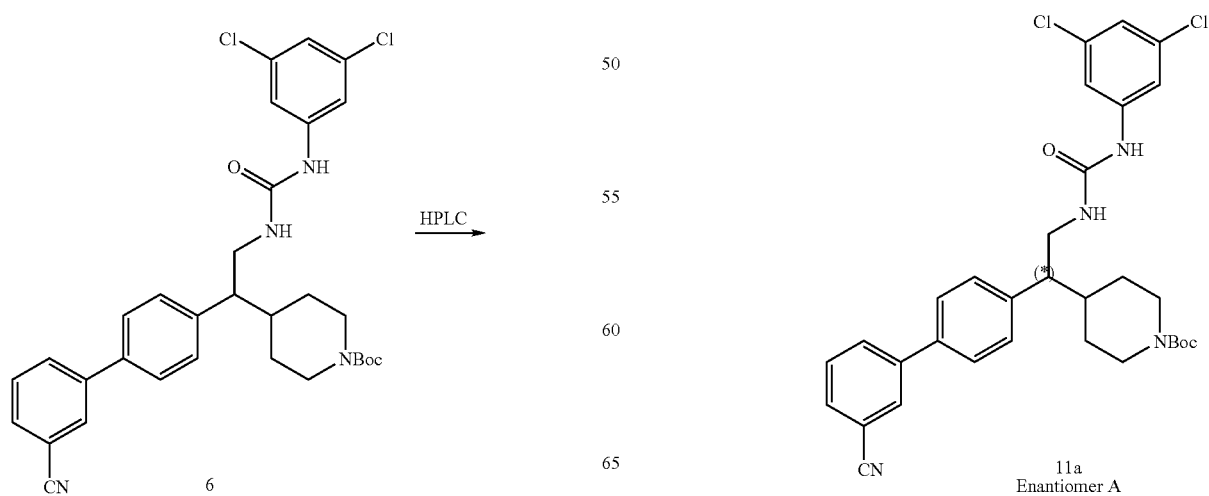

-continued

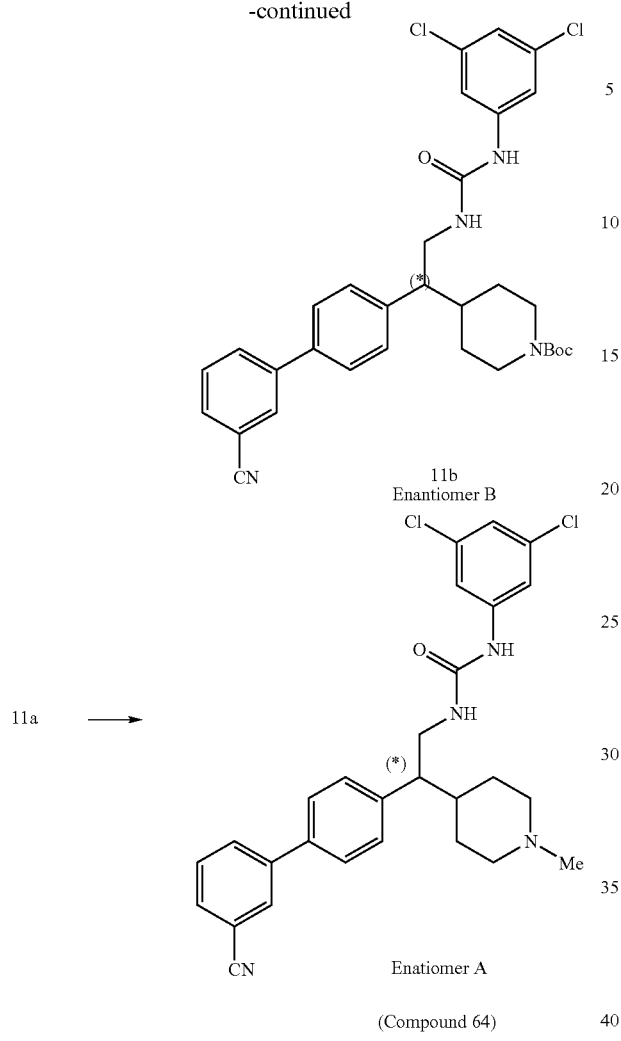

11b
Enantiomer B

11a →

Enatiomer A (Compound 64)

Example 4-A

Application of the sequence of steps from example 3-A to 3-C on amine 5 with the appropriate reagents afforded intermediate 6. Purification of this intermediate (525 mg) by chiral HPLC was performed on Chiracel OD column (eluting Hexanes/isopropanol 8:2) to afford in order of elution: (i) enantiomer A 11a (250 mg); (ii) enantiomer B 11 b (250 mg).

Example 4-B

Application of the sequence of steps from example 1-E to 1-F on enantiomer 11a with the appropriate reagents afforded the final compound: $^1$H-NMR (free base, 300 MHz, CDCl$_3$) δ 7.79 (s, 1H), 7.76 (d, J=6.0 Hz, 1H), 7.61 (d, J=6.0 Hz, 1H), 7.45-7.55 (m, 4H), 7.30 (s, 1 H), 7.22 (d, J=6.4 Hz, 2H), 6.93 (s, 1H), 5.19 (br s, 1H), 3.82 (m, 1H), 3.30 (m, 1H), 2.88 (br d, 1H), 2.77 (br s, 1H), 2.58 (m, 1H), 2.23 (s, 3H), 1.70-2.05 (m, 3H), 1.10-1.65 (m, 4H); HRMS (M+H$^+$) 507.1714.

Using similar procedures, compounds of the following structures were prepared

TABLE 5

| Compound | Structure | Enantiomer | HRMS(M + H$^+$) |
|---|---|---|---|
| 65 | 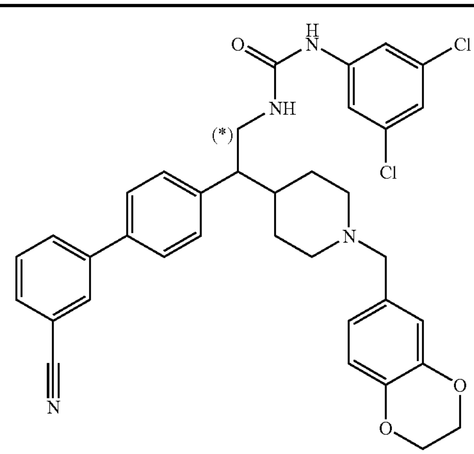 | A | 641.2084 |

TABLE 5-continued
| Compound | Structure | Enantiomer | HRMS(M + H+) |
|---|---|---|---|
| 66 | 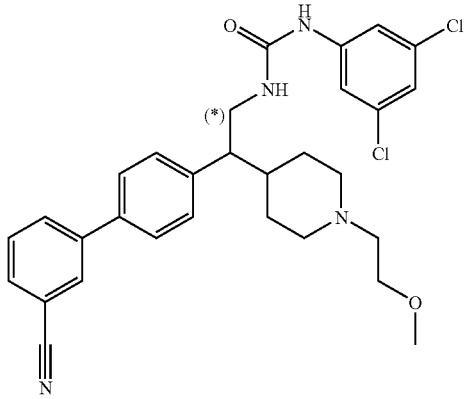 | A | 551.1987 |
| 67 | 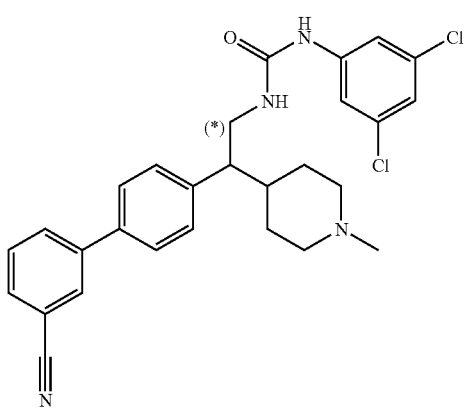 | B | 507.1719 |
| 68 | 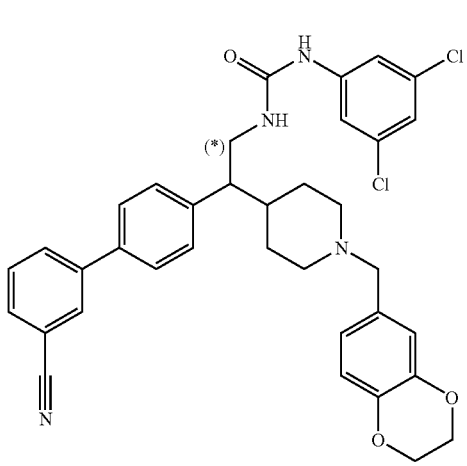 | B | 641.2078 |

TABLE 5-continued

| Compound | Structure | Enantiomer | HRMS(M + H⁺) |
|---|---|---|---|
| 69 | 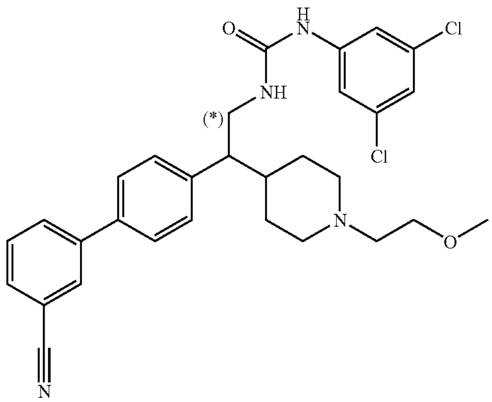 | B | 551.1993 |

Example 5

Compound 70

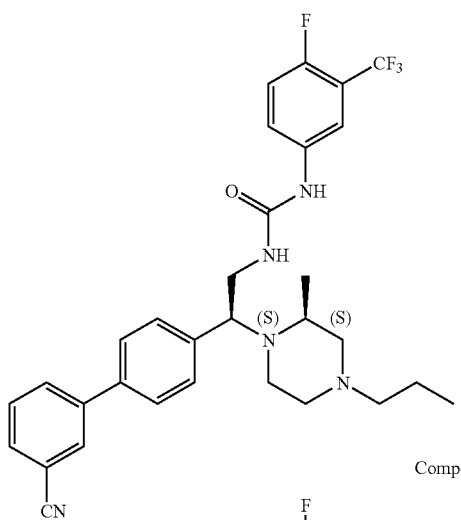

Compound 71

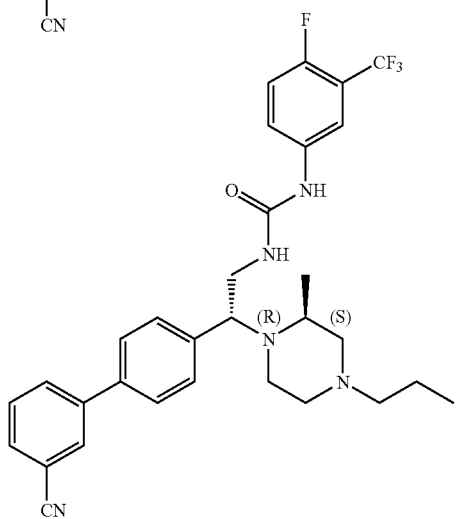

These compounds were prepared according to Scheme 3.

Example 5-A

A solution of 4-bromobenzaldehyde (14.8 g; 80 mmol), N4-Boc protected (S)-2-methyl piperazine (16.1 g; 80 mmol—prepared from the reaction of commercial (S)-2-methylpiperazine with N-(tert-butoxycarbonyl)phthalimide) and titanium(IV)isopropoxide (25.6 ml; 86 mmol) in DCE (150 ml) was stirred overnight at room temperature. The mixture was carefully treated with diethylaluminum cyanide 1N in toluene (142 ml) and stirred 4 h at 75° C. The cooled solution was diluted with $CH_2Cl_2$/AcOEt 1:1, and Celite was added followed by water (30 ml), dropwise. The resulting slurry was filtered over Celite, concentrated and purified by flash-chromatography over silica gel (eluting Hexanes/AcOEt 1:1) to give 23.3 g (74%) of mixture of diastereoisomers 8a-b as an oil.

Example 5-B

Removal of the Boc-protecting group in 8a-b (12.17 g; 310 mmol) proceeded as in Example 1-E to afford 9.5 g (100%) of free amine as a mixture of diastereoisomers.

Example 5-C

Piperazine N-functionalization of free amine (4.0 g; 13.6 mmol) with propionaldehyde followed a procedure similar to the one described in example 1-F to give, after flash-chromatography over silica gel (eluting Hexanes/AcOEt 1:1 to AcOEt), 4.3 g (93%) of diastereoisomeric mixture of bromo cyano intermediates.

Example 5-D

To the bromo cyano intermediates (4.3 g; 12.8 mmol) in THF (40 ml) at 0° C. was slowly lithium aluminum hydride 1N in THF (38.4 ml) followed by boron trifluoride etherate (1.73 ml; 14.1 mmol) and the mixture was stirred overnight at room temperature. The final solution was slowly poured into ice-cooled 2N $H_2SO_4$, stirred 1 h, then neutralized with 3N NaOH and extracted with $CH_2Cl_2$. After concentration, the crude was passed through a plug of silica gel (eluting $CH_2Cl_2$/MeOH 9:1 to 7:3) to provide 2.0 g (50%) of mixture of diastereoisomers 9a-b as an oil.

Example 5-E

Suzuki coupling of 9a-b (2.0 g; 5.9 mmol) and 3-cyanophenylboronic acid proceeded as in example 1-C to give, after flash-chromatography over silica gel (eluting CH$_2$Cl$_2$/MeOH 9:1), 1.54 g (74%) of biaryl amine as a mixture of diastereoisomers.

Example 5-F

Reaction of biaryl amine diastereoisomeric mixture (150 mg; 0.41 mmol) with 4-fluoro-3-trifluoromethylphenyl isocyanate proceeded as in Example 3-B. Purification by preparative chromatography over silica gel (eluting CH$_2$Cl$_2$/AcOEt 7:3) gave, in order of elution: first Ic-a (tentatively assigned the (S,S) configuration), 22.3 mg as hydrochloride salt—$^1$H-NMR (free base, 300 MHz, CDCl$_3$) δ 7.91 (s, 1H), 7.78 (d, J=7.6 Hz, 1H), 7.40-7.70 (m, 6H), 7.25 (d, J=7.9 Hz, 2H), 7.11 (t, J=9.8 Hz, 1H), 5.71 (br s, 1H), 4.25 (m, 1H), 3.50-3.80 (m, 2H), 2.70-2.90 (m, 2H), 2.59 (m, 1H), 2.05-2.45 (m, 4H), 1.89 (m, 1H), 1.45 (m, 2H), 1.19 (d, J=6 Hz, 3H), 0.85 (t, J=7.4 Hz, 3H)—HRMS (M+H$^+$) 568.2700; second Ic-b (tentatively assigned the (R,S) configuration), 124.5 mg as hydrochloride salt—$^1$H-NMR (free base, 300 MHz, CDCl$_3$) δ 7.65-7.80 (m, 3H), 7.40-7.60 (m, 7H), 6.98 (t, J=10 Hz, 1H), 5.51 (br s, 1H), 4.07 (br s, 1H), 3.70-3.80 (m, 1H), 3.40-3.70 (m, 2H), 3.20 (br s, 1H), 2.15-2.60 (m, 6H), 1.46 (m, 2H), 1.18 (d, J=6.3 Hz, 3H), 0.86 (t, J=7.4 Hz, 3H). HRMS (M+H$^+$) 568.2700. Using similar procedures, compounds of the following structures were prepared (Note: tentative chirality assignments were based on the comparison of NMR data as well as TLC properties)

TABLE 6

| Compound | Structure | HRMS(M + H$^+$) | $^1$H-NMR (free base, 300 MHz, CDCl$_3$) |
|---|---|---|---|
| 72 | 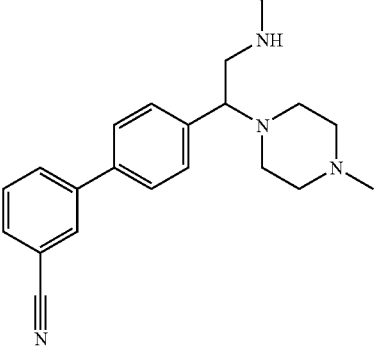 | 508.1674 | 7.81 (s, 1H), 7.79 (d, J=8.2 Hz, 1H), 7.64 (m, 1H), 7.50–7.60 (m, 2H), 7.25–7.35 (m, 5H), 6.98 (s, 1H), 5.77 (br s, 1H), 3.55–3.80 (m, 4H), 2.60–2.80 (m, 6H), 2.43 (s, 3H) |
| 73 | 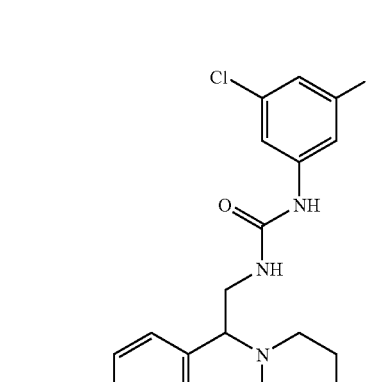 | 495.1349 | 7.75 (s, 1H), 7.73 (d, J=8.0 Hz, 1H), 7.45–7.65 (m, 5H), 7.31 (d, J=6.3 Hz, 2H), 7.26 (s, 1H), 6.93 (s, 1H), 5.63 (br s, 1H), 3.89 (m, 1H), 3.60–3.75 (m, 4H), 3.45–3.60 (m, 2H), 2.46 (m, 4H) |

TABLE 6-continued

| Compound | Structure | HRMS(M + H⁺) | ¹H-NMR (free base, 300 MHz, CDCl₃) |
|---|---|---|---|
| 74 | 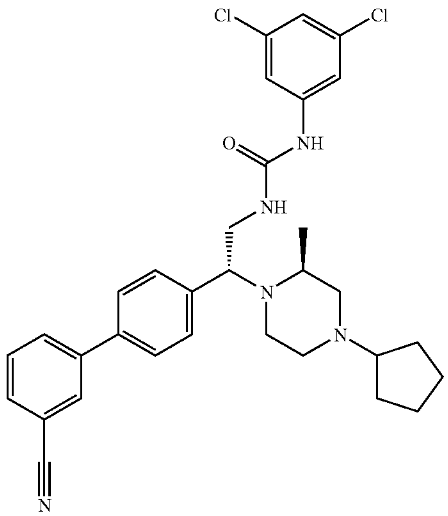 | 576.2290 | |
| 75 | 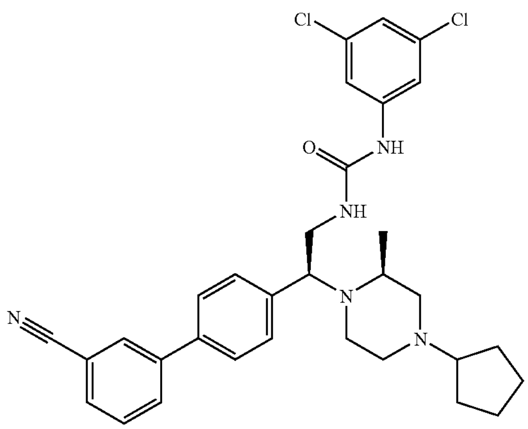 | 576.2302 | |
| 76 | 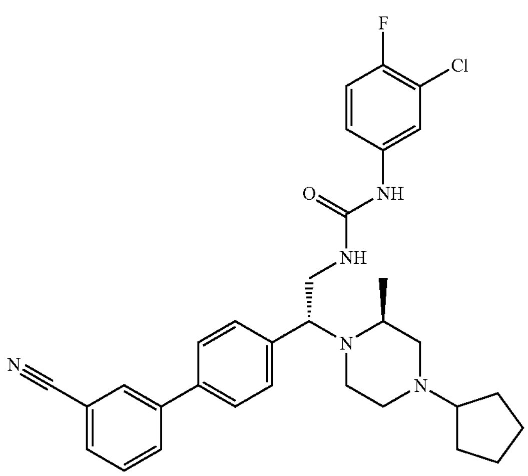 | 560.2599 | |

TABLE 6-continued

| Compound | Structure | HRMS(M + H+) | 1H-NMR (free base, 300 MHz, CDCl3) |
|---|---|---|---|
| 77 | 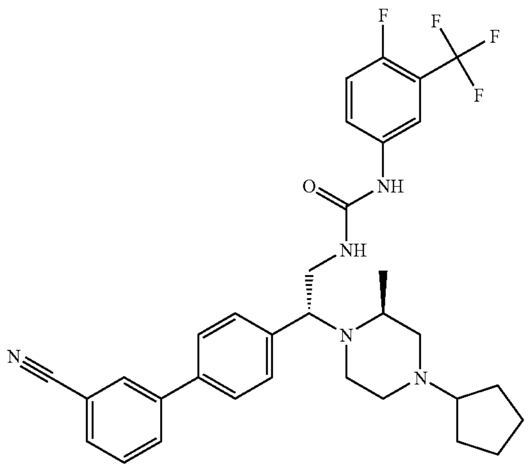 | 594.2846 | |
| 78 | 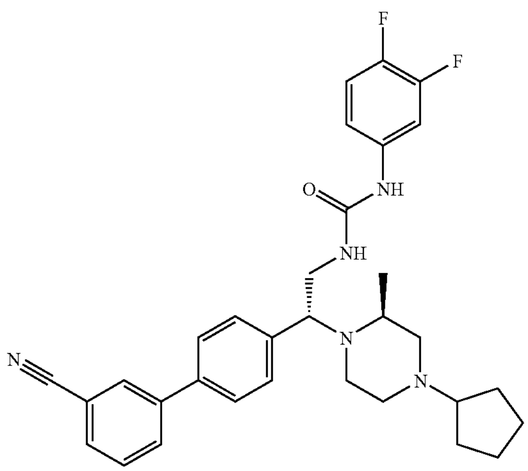 | 544.2872 | |
| 79 | 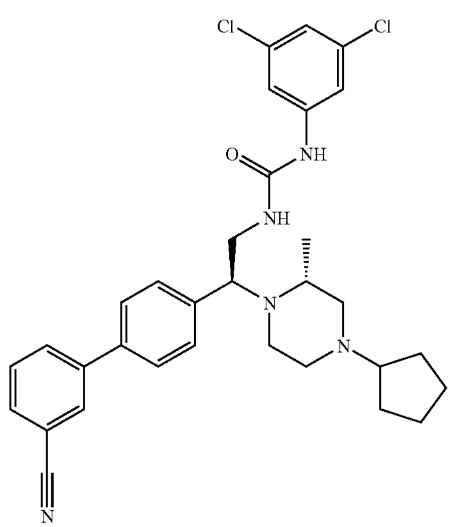 | 576.2291 | |

TABLE 6-continued
| Compound | Structure | HRMS(M + H+) | 1H-NMR (free base, 300 MHz, CDCl3) |
|---|---|---|---|
| 80 | 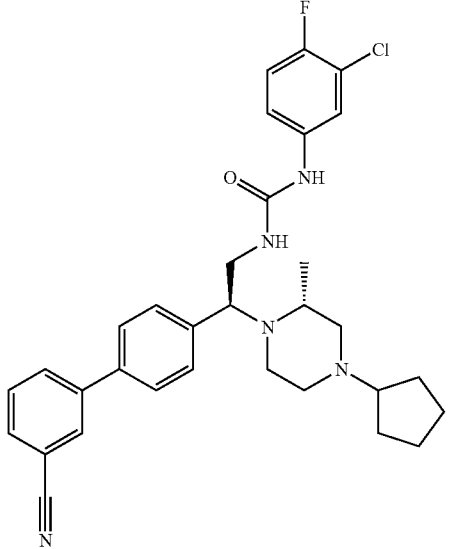 | 560.2599 | |
| 81 | 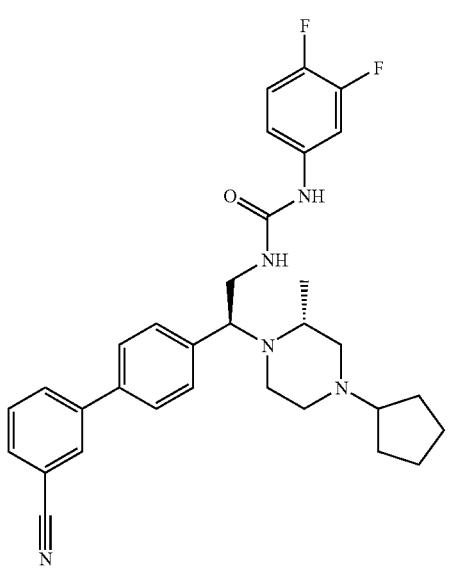 | 544.2895 | |

TABLE 6-continued

| Compound | Structure | HRMS(M + H+) | 1H-NMR (free base, 300 MHz, CDCl3) |
|---|---|---|---|
| 82 | 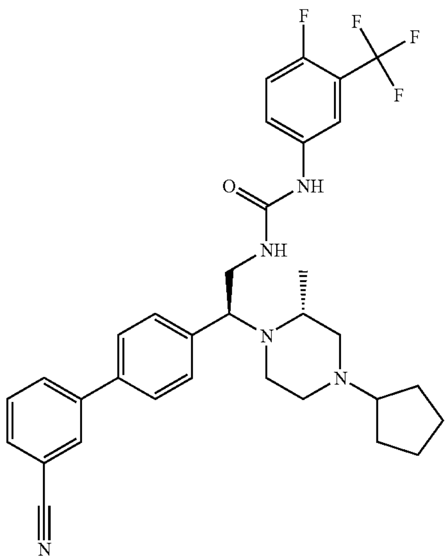 | 594.2852 | |
| 83 | 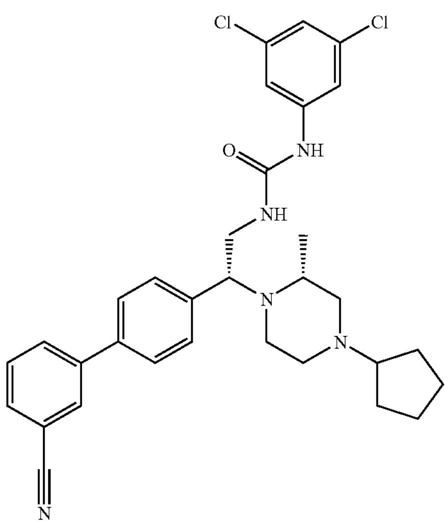 | 576.2285 | |
| 84 | 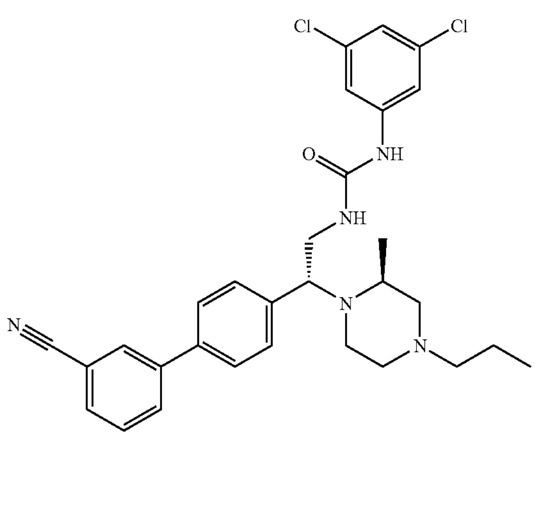 | 550.2148 | |

TABLE 6-continued

| Compound | Structure | HRMS(M + H+) | 1H-NMR (free base, 300 MHz, CDCl3) |
|---|---|---|---|
| 85 | 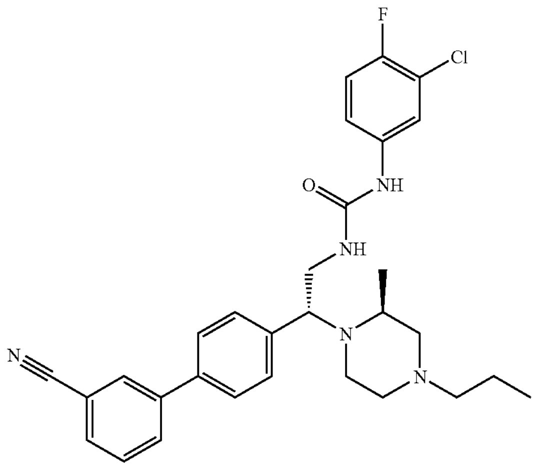 | 534.2439 | |
| 86 | 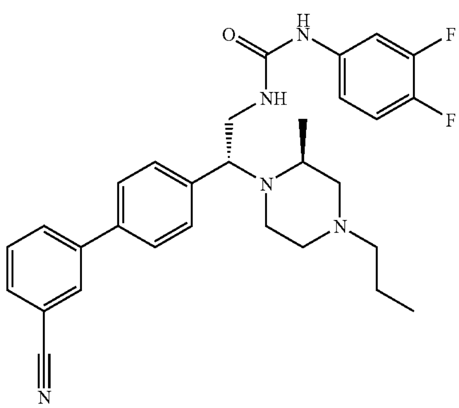 | 518.2721 | |
| 87 | 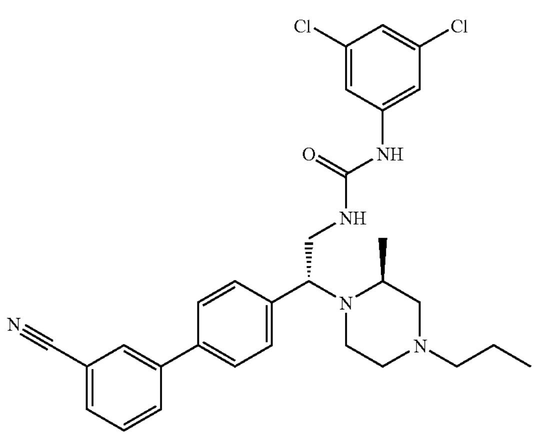 | 550.2148 | |

TABLE 6-continued

| Compound | Structure | HRMS(M + H⁺) | ¹H-NMR (free base, 300 MHz, CDCl₃) |
|---|---|---|---|
| 88 | 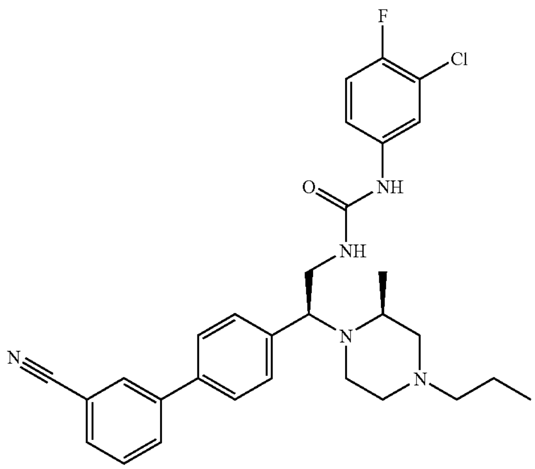 | 534.2444 | 7.81 (s, 1H), 7.80 (d, J=8.1 Hz, 1H), 7.63 (m, 1H), 7.40–7.55 (m, 6H), 7.10 (m, 1H), 6.99 (t, J=8.7 Hz, 1H), 5.21 (br s, 1H), 4.05 (br s, 1H), 3.75 (m, 1H), 3.62 (m, 1H), 3.29 (m, 1H), 2.82 (br s, 1H), 2.25–2.60 (m, 7H), 1.51 (m, 2H), 1.21 (d, J=6.3 Hz, 3H), 0.89 (t, J= 7.4 Hz, 3H) |
| 89 | 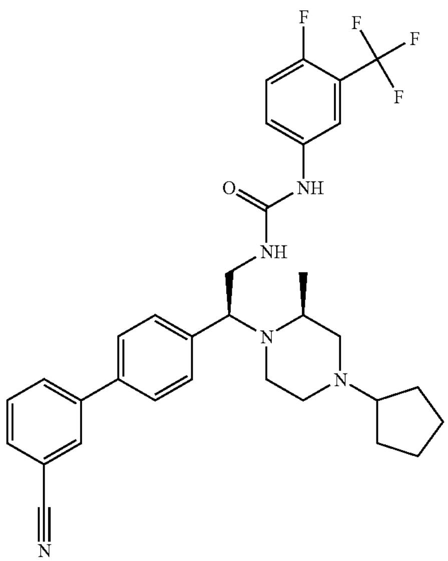 | 594.2852 | |
| 90 | 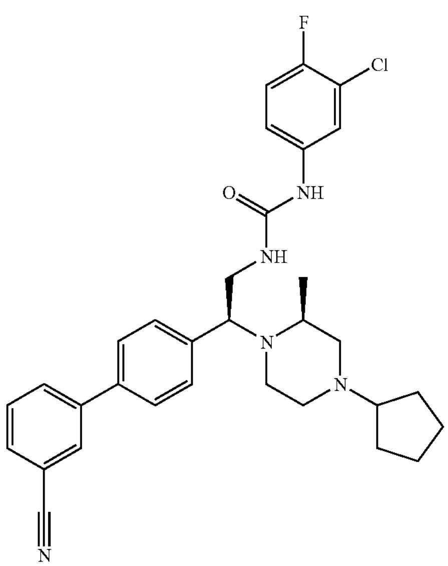 | 560.2593 | |

TABLE 6-continued

| Compound | Structure | HRMS(M + H⁺) | ¹H-NMR (free base, 300 MHz, CDCl₃) |
|---|---|---|---|
| 91 | 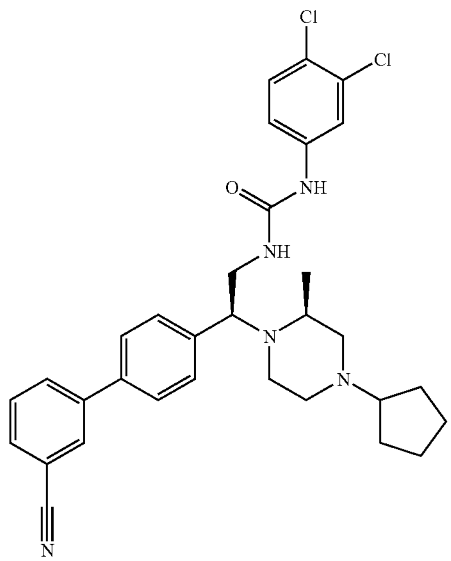 | 576.2302 | |
| 92 | 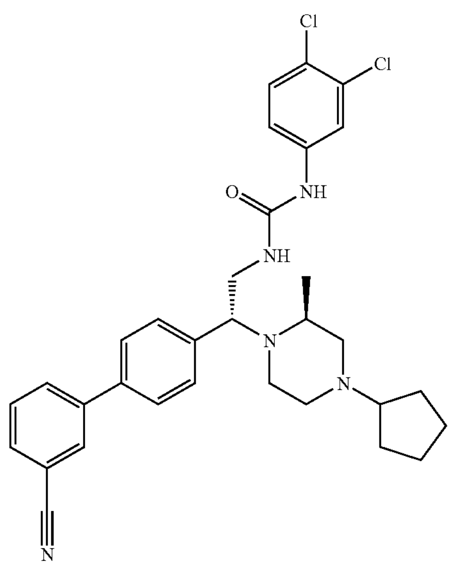 | 576.2302 | |
| 93 | 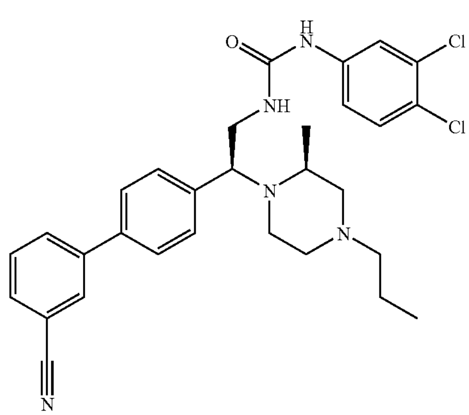 | 550.2143 | |

TABLE 6-continued

| Compound | Structure | HRMS(M + H⁺) | ¹H-NMR (free base, 300 MHz, CDCl₃) |
|---|---|---|---|
| 94 | 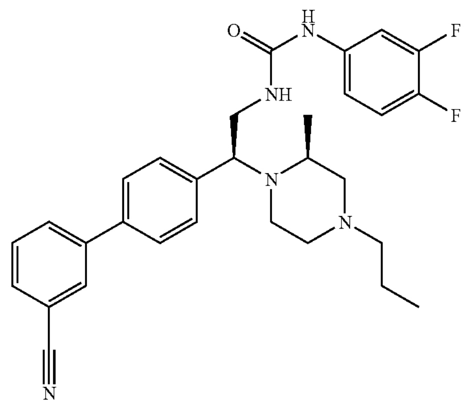 | 518.2733 | |
| 95 | 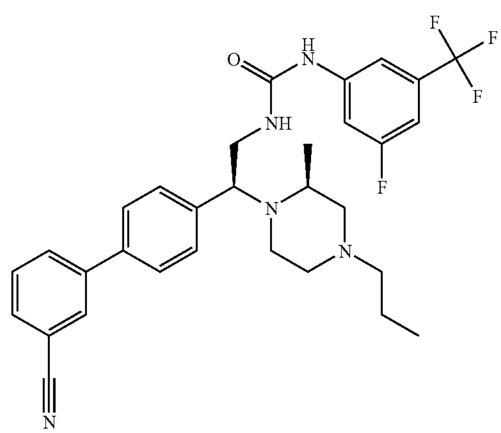 | 568.2700 | |
| 96 | 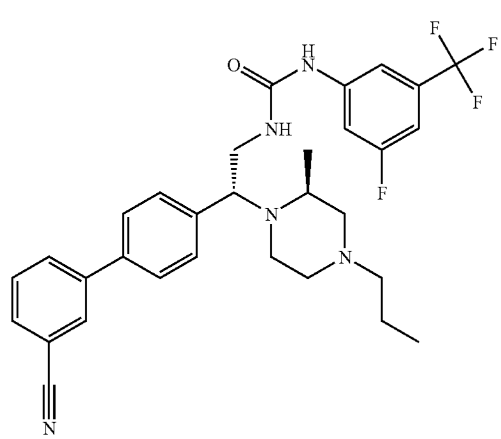 | 568.2700 | |

TABLE 6-continued

| Compound | Structure | HRMS(M + H+) | 1H-NMR (free base, 300 MHz, CDCl3) |
|---|---|---|---|
| 97 | 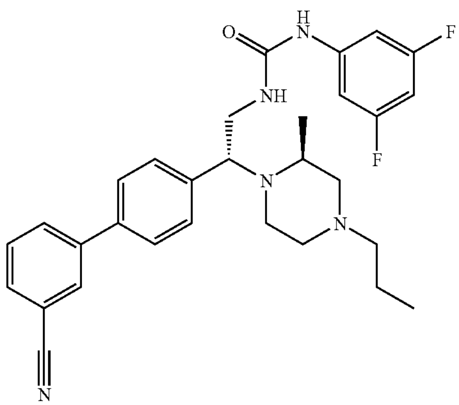 | 518.2733 | |
| 98 | 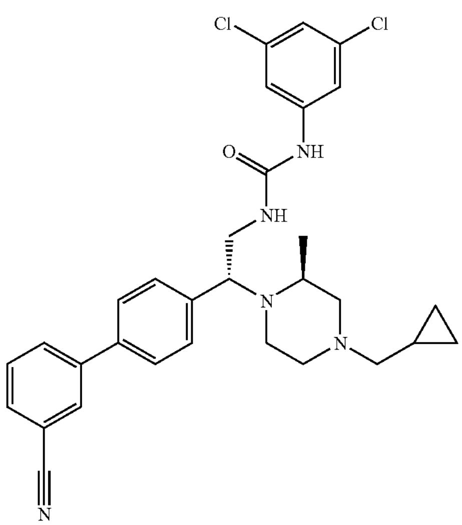 | 562.2144 | |
| 99 | 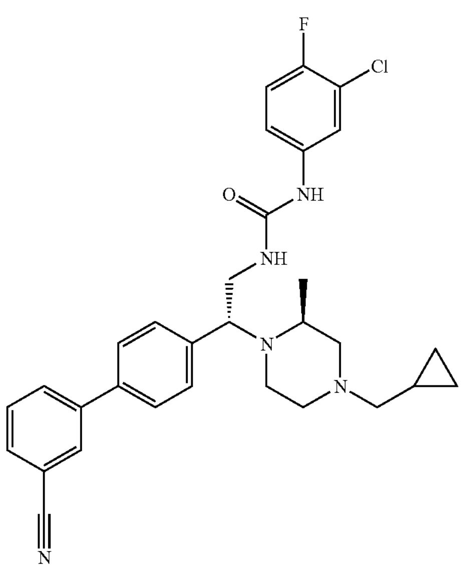 | 546.2432 | 7.70–7.80 (m, 2H), 7.58 (m, 2H), 7.35–7.55 (m, 5H), 7.07 (m, 1H), 6.95 (t, J= 8.5 Hz, 1H), 5.56 (br s, 1H), 4.15 (br s, 1H), 3.60–3.75 (m, 2H), 3.21 (m, 1H), 3.03 (s, 2H), 2.67 (br s, 1H), 2.45–2.60 (m, 3H), 2.10–2.35 (m, 3H), 1.19 (d, J= 6.3 Hz, 3H), 0.82 (m, 1H), 0.49 (d, J= 7.5 Hz, 2H), 0.07 (d, J=4.6 Hz, 2H) |

TABLE 6-continued

| Compound | Structure | HRMS(M + H+) | 1H-NMR (free base, 300 MHz, CDCl3) |
|---|---|---|---|
| 100 | 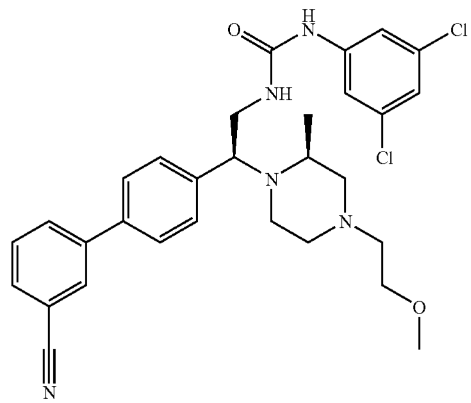 | 566.2097 | |
| 101 | 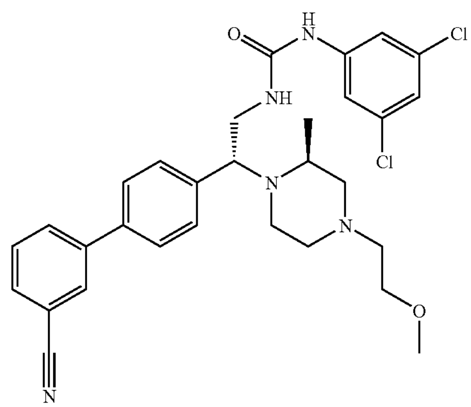 | 566.2097 | |
| 102 | 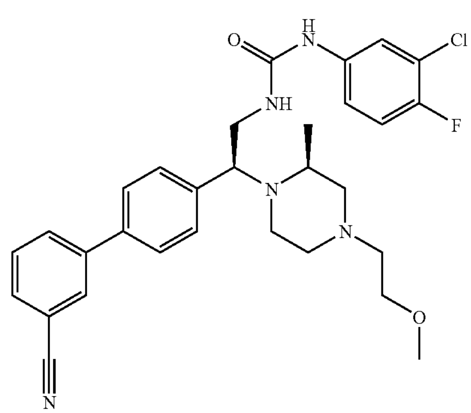 | 550.2394 | |

TABLE 6-continued

| Compound | Structure | HRMS(M + H⁺) | ¹H-NMR (free base, 300 MHz, CDCl₃) |
|---|---|---|---|
| 103 | 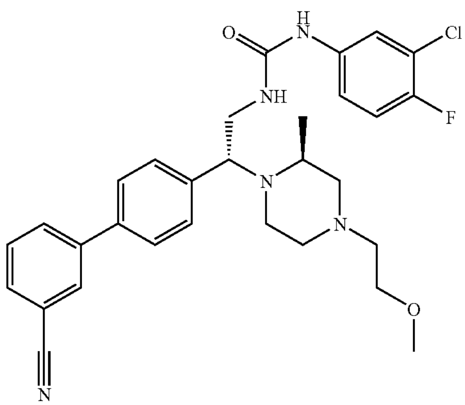 | 550.2389 | |
| 104 | 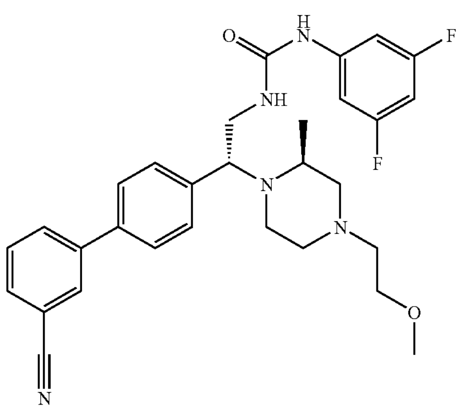 | 534.2687 | 7.83 (s, 1H), 7.70–7.80 (m, 2H), 7.59 (m, 2H), 7.40–7.55 (m, 3H), 6.94 (d, J= 9 Hz, 2H), 6.38 (t, J=9 Hz, 1H), 5.46 (br s, 1H), 4.11 (m, 1H), 3.68 (m, 2H), 3.50 (m, 2H), 3.32 (s, 3H), 3.21 (m, 2H), 2.40–2.70 (m, 5H), 2.20–2.35 (m, 2H), 1.17 (d, J=6.0 Hz, 3H) |
| 105 | 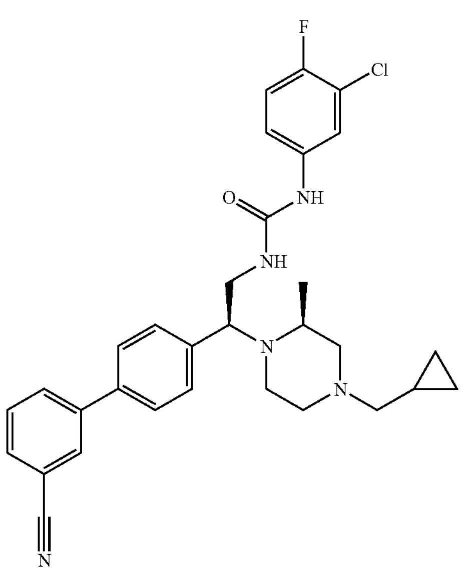 | 546.2438 | |

TABLE 6-continued
| Compound | Structure | HRMS(M + H+) | 1H-NMR (free base, 300 MHz, CDCl3) |
|---|---|---|---|
| 106 | 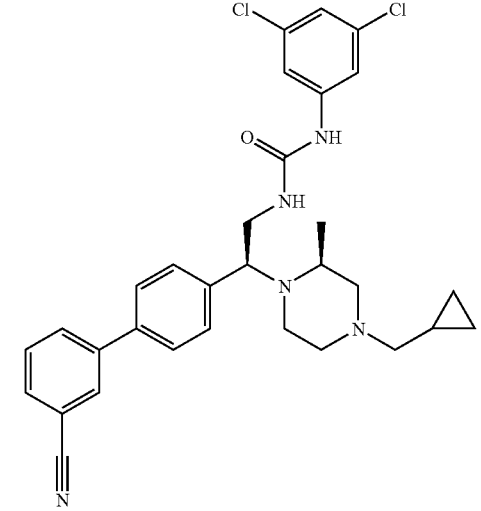 | 562.2142 | |
| 107 | 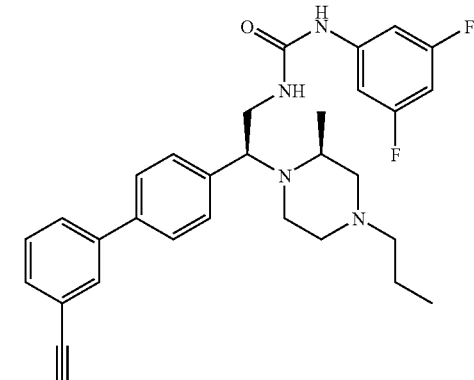 | 518.2730 | |
| 108 | 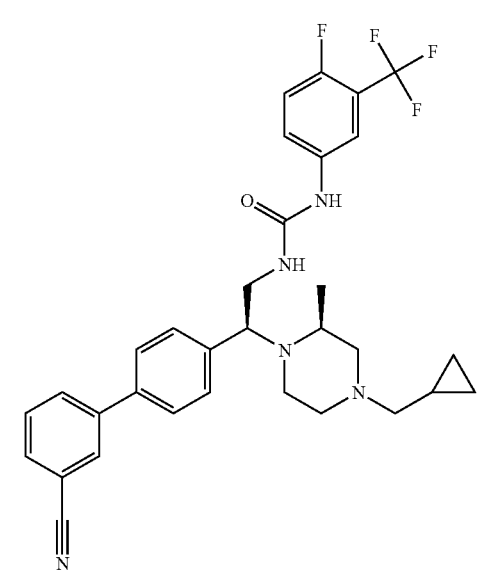 | 580.2690 | |

TABLE 6-continued

| Compound | Structure | HRMS(M + H⁺) | ¹H-NMR (free base, 300 MHz, CDCl₃) |
|---|---|---|---|
| 109 | 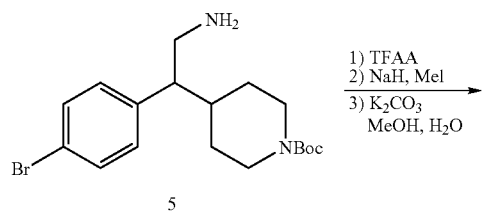 | 530.2732 | |

Example 6

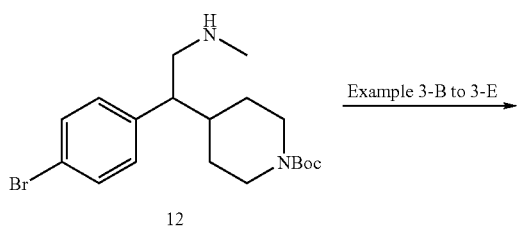

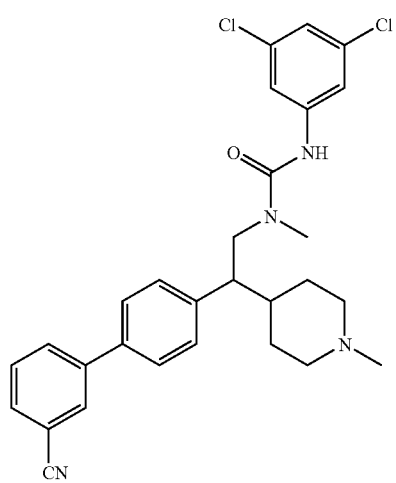

Compound 110

Example 6-A

To a solution of amine 5 (325 mg; 0.85 mmol) in CH₂Cl₂ (3 mL) at 0° C. was added pyridine (102 µL; 1.3 mmol) followed by trifluoroacetic anhydride (131 µL; 0.93 mmol) and the solution was stirred overnight at room temperature. The crude mixture was directly purified by flash chromatography over silica gel (eluting CH₂Cl₂/MeOH 95:5 to 9:1) to yield 300 mg (75%) of trifluoroacetamide.

Example 6-B

Trifluoroacetamide (300 mg; 0.63 mmol) in THF (2 mL) at 0° C. was treated with NaH 60% dispersion in mineral oil (50 mg; 0.63 mmol) followed by MeI. (60 µL; 0.94 mmol) and the reaction was stirred at room temperature overnight. THF was evaporated, the residue was diluted with water and extracted with CH₂Cl₂. Combined organic layers were washed with saturated brine, dried over Na₂SO₄, concentrated and the crude was purified by flash chromatography over silica gel (eluting Hexanes/AcOEt 4:1 to 1:1) to give 200 mg (65%) of N-methyltrifluoroacetamide.

Example 6-C

A solution of N-methyltrifluoroacetamide (200 mg: 0.41 mmol) and potassium carbonate (282 mg; 2.0 mmol) in MeOH (4 mL) and water (1 mL) was stirred at room temperature overnight. After concentration of MeOH, the mixture was diluted with water and extracted with CH₂Cl₂ then AcOEt. Organic layers were washed with saturated brine, dried over Na₂SO₄ and concentrated to yield 190 mg (100%) of N-methyl amine 12.

Example 6-D

Application of the sequence of steps from example 3-B to 3-E on N-methylamine 12 with the appropriate reagents afforded the final compound: ¹H-NMR (free base, 300 MHz, CDCl₃) δ 7.82 (s, 1H), 7.78 (d, J=7.8 Hz, 1H), 7.50-7.65 (m, 4H), 7.31 (d, J=8.1 Hz, 2H), 7.10 (s, 2H), 6.92 (s, 1H), 6.01 (s, 1H), 3.82 (dd, J=14 Hz and 5 Hz, 1H), 3.67 (dd, J=14 Hz and 10 Hz, 1H), 3.04 (br d, 1H), 2.75-2.95 (m, 2H), 2.79 (s, 3H), 2.33 (s, 3H), 1.90-2.15 (m, 3H), 1.20-1.75 (m, 4H); HR (M+H⁺) 521.1884.

Example 7

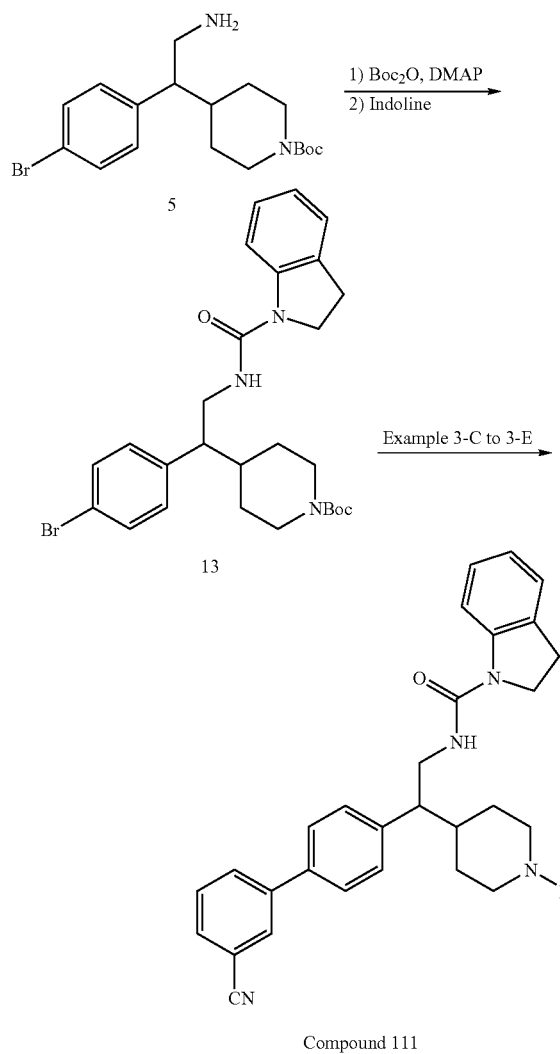

Example 7-A

To a solution of Boc$_2$O (240 mg; 1.10 mmol) in anhydrous CH$_2$Cl$_2$ (3 mL). was added DMAP (100 mg; 0.82 mmol) followed by amine 5 (300 mg; 0.78 mmol) in CH$_2$Cl$_2$ and the reaction mixture was stirred 1 h at room temperature. Indoline (205 mg; 1.7 mmol) in CH$_2$Cl$_2$ was added and the reaction was stirred overnight. The crude mixture was poured into 0.2 N NaOH, extracted with CH$_2$Cl$_2$ then AcOEt. Combined organic layers were dried over Na$_2$SO$_4$, concentrated, and the crude was purified by preparative silica gel chromatography (eluting Hexanes/AcOEt 7:3) to yield 227 mg (55%) of indoline urea 13.

Example 7-B

Application of the sequence of steps from example 3-C to 3-E on indoline urea 13 with the appropriate reagents afforded the final compound: $^1$H-NMR (free base, 300 MHz, CDCl$_3$) δ 7.86 (s, 1H), 7.83 (d, J=7.2 Hz, 1H), 7.50-7.70 (m, 5H), 7.29 (d, J=8.4 Hz, 2H), 7.00-7.15 (m, 2H), 6.86 (t, J=7.1 Hz, 1H), 4.60 (br s, 1H), 4.35 (m, 1H), 4.03 (m, 1H), 3.61 (t, J=8.7 Hz, 2H), 3.39 (m, 1H), 3.05 (t, J=8.7 Hz, 2H), 2.88 (br d, 1H), 2.77 (m, 1H), 2.31 (s, 3H), 1.90-2.15 (m, 3H), 1.25-1.75 (m, 4H); HR (M+H$^+$) 465.2650.

Using similar procedures, the compound of the following structure was prepared

TABLE 7

| Compound | Structure | HRMS(M + H$^+$) | LCMS (retention time; MS) |
|---|---|---|---|
| 112 | 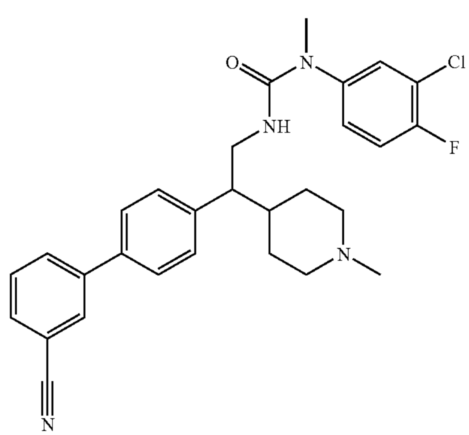 | 505.2174 | |

TABLE 7-continued

| Compound | Structure | HRMS(M + H+) | LCMS (retention time; MS) |
|---|---|---|---|
| 113 | 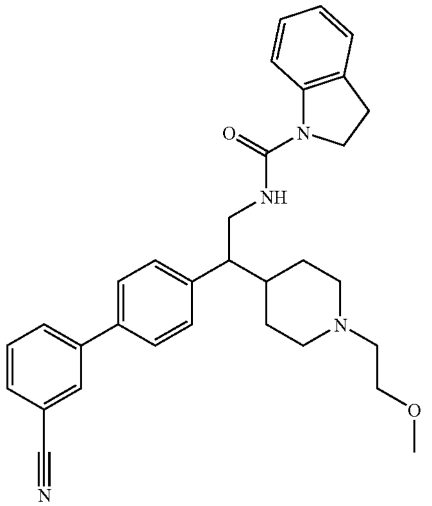 | 509.2907 | 4.66; 509.1 |

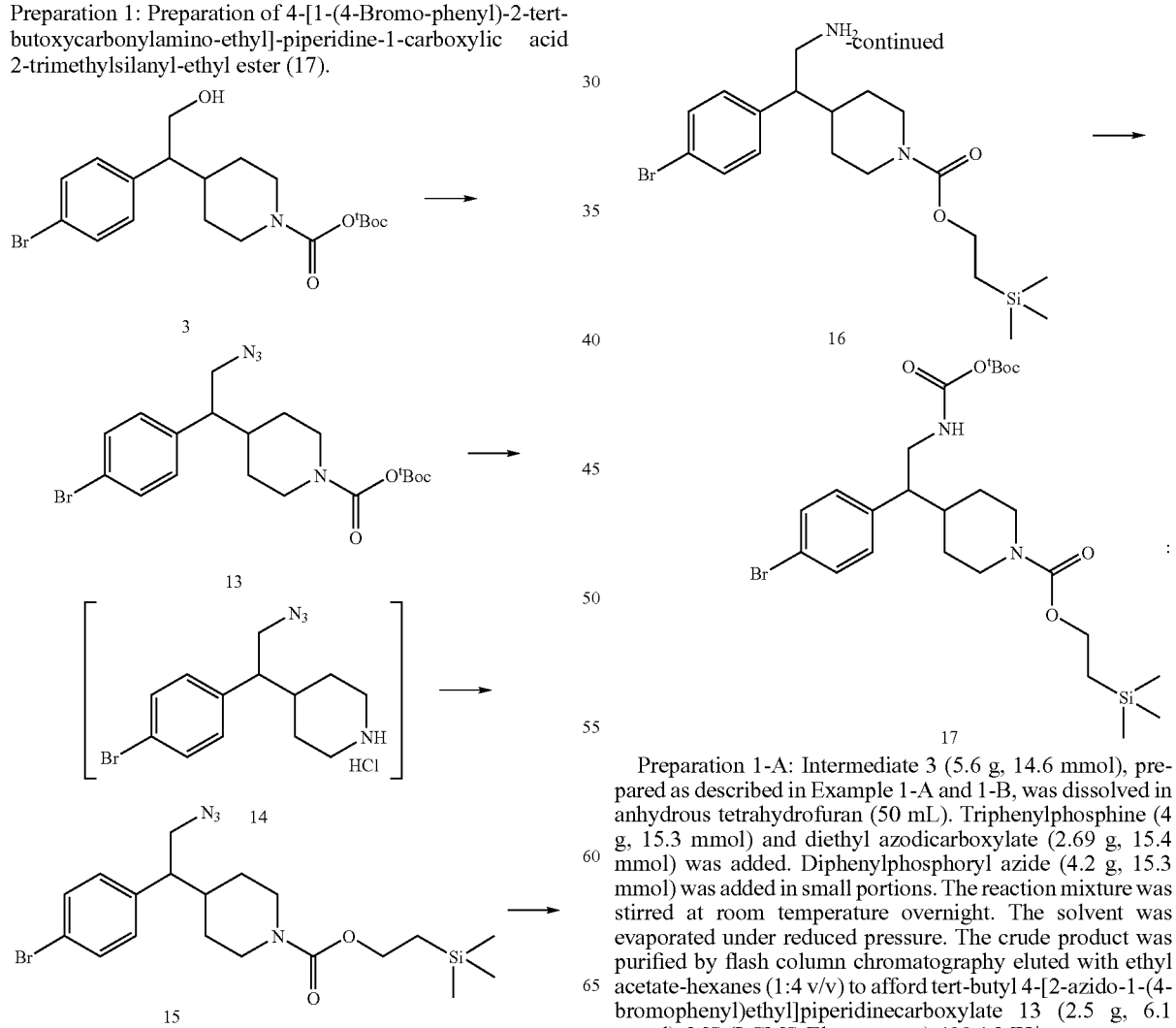

Preparation 1: Preparation of 4-[1-(4-Bromo-phenyl)-2-tert-butoxycarbonylamino-ethyl]-piperidine-1-carboxylic acid 2-trimethylsilanyl-ethyl ester (17).

Preparation 1-A: Intermediate 3 (5.6 g, 14.6 mmol), prepared as described in Example 1-A and 1-B, was dissolved in anhydrous tetrahydrofuran (50 mL). Triphenylphosphine (4 g, 15.3 mmol) and diethyl azodicarboxylate (2.69 g, 15.4 mmol) was added. Diphenylphosphoryl azide (4.2 g, 15.3 mmol) was added in small portions. The reaction mixture was stirred at room temperature overnight. The solvent was evaporated under reduced pressure. The crude product was purified by flash column chromatography eluted with ethyl acetate-hexanes (1:4 v/v) to afford tert-butyl 4-[2-azido-1-(4-bromophenyl)ethyl]piperidinecarboxylate 13 (2.5 g, 6.1 mmol). MS (LCMS-Electrospray) 409.1 MH+.

Preparation 1-B: A solution of hydrogen chloride in 1,4-dioxane (4 M, 60 mL, 240 mmol) was added to tert-butyl 4-[2-azido-1-(4-bromophenyl)ethyl]piperidinecarboxylate 13 (2.5 g, 6.1 mmol). The reaction mixture was stirred at room temperature for 1 h. The solvent was evaporated under reduced pressure. The residue containing 4-[2-azido-1-(4-bromophenyl)ethyl]piperidine hydrochloride 14 was dissolved in a 50% v/v aqueous tetrahydrofuran solution (68 mL). Potassium carbonate (2.12 g, 15.3 mmol) and 2-(trimethylsilyl)ethyl p-nitrophenyl carbonate (1.74 g, 61.4 mmol) were added. The reaction mixture was stirred at room temperature for 3 h. Organic solvent was evaporated under reduced pressure. Ethyl acetate was added. The organic layer was washed with aqueous sodium bicarbonate solution, water and brine. The organic layer was dried over sodium sulfate. The solvent was evaporated under reduced pressure. The crude product was purified by flash column chromatography eluted with ethyl acetate-hexanes (1:5 v/v) to afford 2-(trimethylsilyl)ethyl 4-[2-azido-1-(4-bromophenyl)ethyl]piperidinecarboxylate 15 (2.1 g, 4.6 mmol). MS (LCMS-Electrospray) 454.1 MH$^+$.

Preparation 1-C To a solution of 2-(trimethylsilyl)ethyl 4-[2-azido-1-(4-bromophenyl)ethyl]piperidinecarboxylate 15 (4.3 g, 9.5 mmol) in tetrahydrofuran-water (10:1 v/v) at room temperature was added triphenylphoshine (4.97 g, 19 mmol). The reaction mixture was stirred under a nitrogen atmosphere and heated under reflux overnight. Organic solvent was evaporated under reduced pressure. Dichloromethane was added. The organic layer was washed with aqueous sodium bicarbonate solution. The organic layer was dried over sodium sulfate. The solvent was evaporated under reduced pressure. The residue containing 2-(trimethylsilyl)ethyl 4-[2-amino-1-(4-bromophenyl)ethyl]piperidinecarboxylate 16 was dissolved in 1,4-dioxane (40 mL). Di-tert-butyl dicarbonate (2.1 g, 9.6 mmol) was added. The reaction mixture was stirred at room temperature for 3 h. The solvent was evaporated under reduced pressure. The crude product was purified by flash column chromatography eluted with ethyl acetate-hexanes (1:6 v/v) to afford 2-(trimethylsilyl)ethyl 4-{2-[(tert-butoxy)carbonylamino]-1-(4-bromophenyl)ethyl}piperidinecarboxylate 17 (4.3 g, 8.2 mmol). MS (LCMS-Electrospray) 528.1 MH$^+$.

Example 8

Preparation of Libraries of Compounds of Type 27

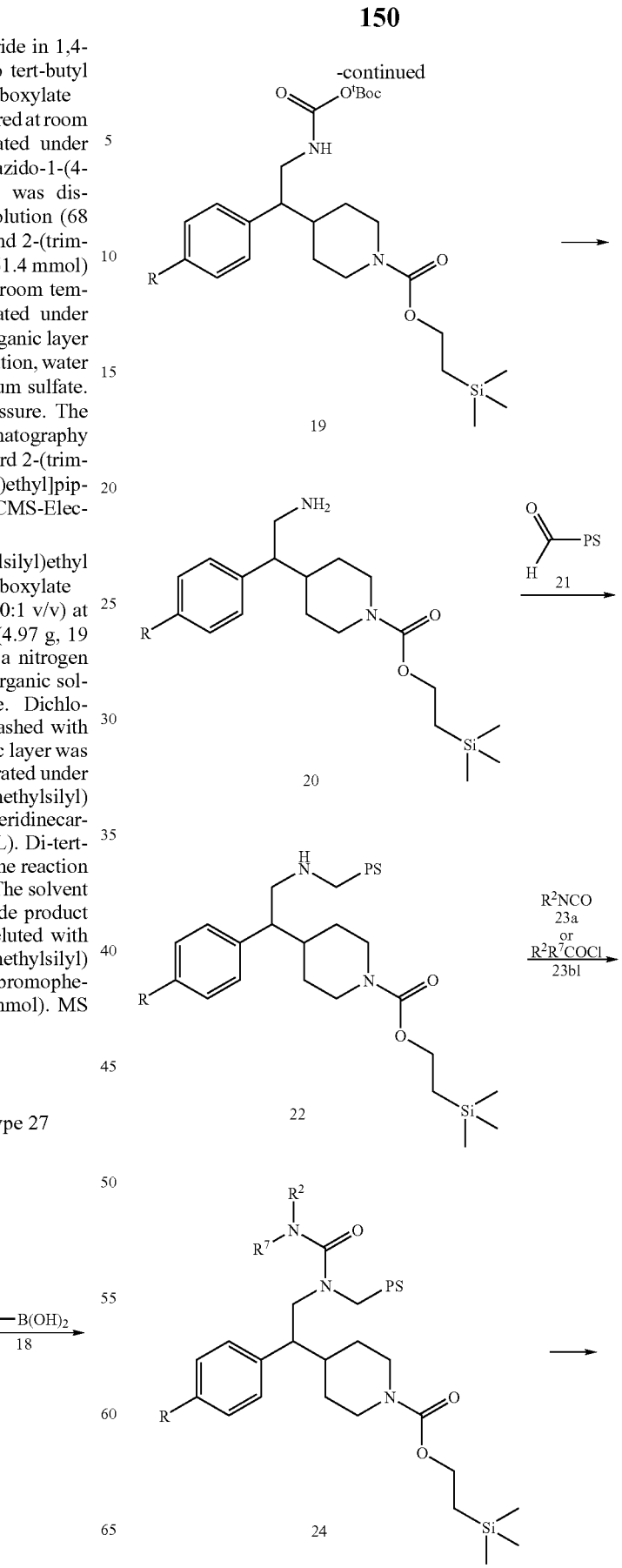
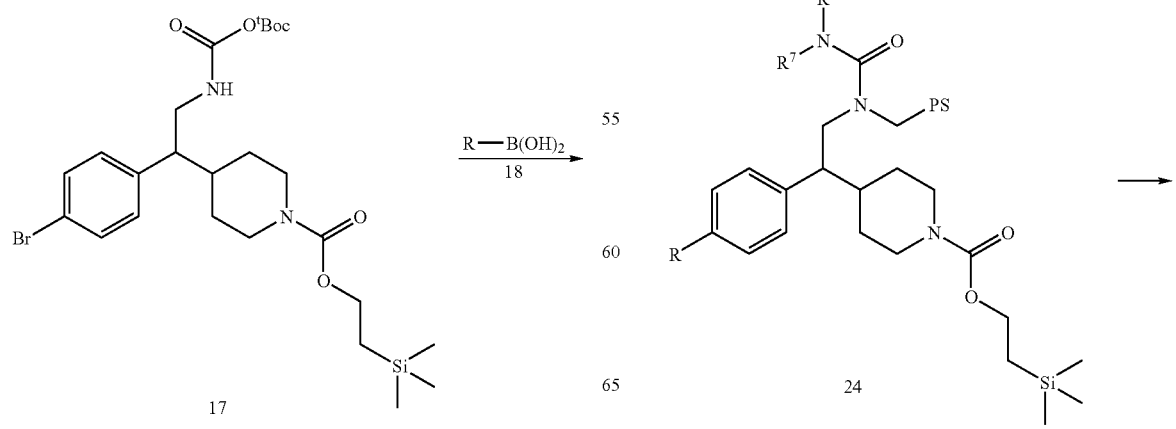

-continued

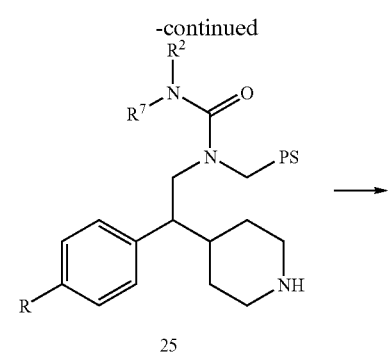

25

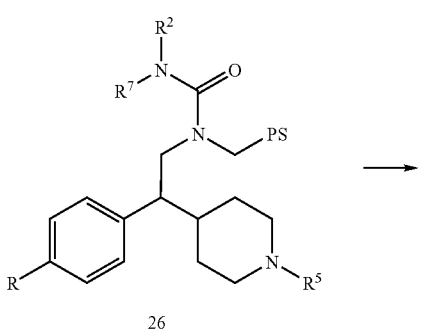

26

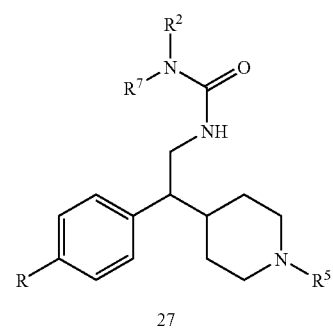

27

Example 8-A

To a solution of 2-(trimethylsilyl)ethyl 4-{2-[(tert-butoxy)carbonylamino]-1-(4-bromophenyl)ethyl}piperidinecarboxylate 17 from preparation 1 (2.6 g, 4.9 mmol) in dimethoxyethane (28 mL) was added saturated aqueous sodium carbonate solution (14 mL), boronic acid 18 (7.3 mmol) and [1,1'-bis(diphenylphosphino)ferrocene]-dichloropalladium (II) (0.6 g, 0.82 mmol). The reaction mixture was heated under reflux for 4 h. Organic solvent was evaporated under reduced pressure. Ethyl acetate was added. The organic layer was washed with water and brine. The organic layer was dried over sodium sulfate. The solvent was evaporated under reduced pressure. The crude product was purified by flash column chromatography to afford compound 19.

Example 8-B

To a solution of compound 19 (4.6 mmol) in ethanol (15 mL) at room temperature was added p-toluenesulfonic acid (1.3 g, 6.8 mmol). The reaction mixture was heated under reflux overnight. The solvent was evaporated under reduced pressure. Dichloromethane was added. The organic layer was washed with aqueous sodium bicarbonate solution. The organic layer was dried over sodium sulfate. The solvent was evaporated under reduced pressure. The residue containing compound 20 was used in the next reaction without further purification.

Example 8-C

The solid phase synthesis was conducted in a reaction vessel (IRORI Minikan®)which was constructed from a porous polypropylene capsule. An aldehyde resin 21 (Novabiochem 2-(4-formyl-3-methoxyphenoxy)ethyl polystyrene) (0.018 mmol) was treated with a solution of compound 20 (0.036 mmol) and sodium triacetoxyborohydride (0.09 mmol) in acetic acid-tetrahydrofuran (1:19 v/v) at room temperature overnight. The resin was washed with methanol-N.N-dimethylformamide (1:5 v/v) (4 times) and N,N-dimethylformamide (4 times) to afford the resin-bound compound 22.

Example 8-D

The resin-bound compound 22 was treated with a solution of substituted isocyanate 23a (0.18 mmol) in N,N-dimethylformamide at room temperature overnight. The resin was washed with N,N-dimethylformamide (4 times) and tetrahydrofuran (4 times) to afford the resin-bound compound 24. Alternatively, the resin-bound compound 22 was treated with a solution of substituted carbamyl chloride 23b (0.18 mmol) and di-iso-propylethylamine (0.36 mmol) in N,N-dimethylformamide at room temperature overnight. The resin was washed with N,N-dimethylformamide (4 times) and tetrahydrofuran (4 times) to afford the resin-bound compound 24.

Example 8-E

The resin-bound compound 24 was treated with a 1 N solution of tetrabutylammonium fluoride in tetrahydrofuran at room temperature for 2 h. The resin was washed with tetrahydrofuran (4 times) to afford the resin-bound compound 25.

Example 8-F

The resin-bound compound 25 was treated with a solution of aldehyde or ketone (0.18 mmol) and sodium triacetoxyborohydride (0.18 mmol) in acetic acid-tetrahydrofuran (1:19 v/v) at room temperature overnight. The resin was washed with methanol-tetrahydrofuran (1:5 v/v) (4 times), tetrahydrofuran (4 times) and dichloromethane (4 times) to afford the resin-bound compound 26.

Example 8-G

The resin-bound compound 801D was treated with 3 mL of a trifluoroacetic acid-water-dichloromethane (38:2:60 v/v) solution at room temperature for 20 min. The filtrate was added to 1 mL of acetic acid and the solution was concentrated by vacuum centrifugation to afford compound 27.

Using the above procedure, libraries of the following compounds were prepared:

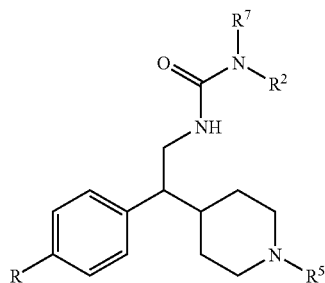

| R | R² | R⁷ | R⁵ | obs M + 1 m/z |
|---|---|---|---|---|
| Phenyl | 3-chlorophenyl | H | H | 434.1 |
| Phenyl | 3-chlorophenyl | H | methyl | 448.1 |
| Phenyl | 3-chlorophenyl | H | cyclopropylmethyl | 488.1 |
| Phenyl | 3-chlorophenyl | H | cyclopentyl | 502.1 |
| Phenyl | 3-chlorophenyl | H | 3,4-methylenedioxybenzyl | 568.1 |
| Phenyl | 3,5-dichlorophenyl | H | H | 468.1 |
| Phenyl | 3,5-dichlorophenyl | H | methyl | 482.1 |
| Phenyl | 3,5-dichlorophenyl | H | cyclopropylmethyl | 522.1 |
| Phenyl | 3,5-dichlorophenyl | H | cyclopentyl | 536.1 |
| Phenyl | 3,5-dichlorophenyl | H | 3,4-methylenedioxybenzyl | 602.1 |
| Phenyl | 3-fluorophenyl | H | H | 418.1 |
| Phenyl | 3-fluorophenyl | H | methyl | 432.1 |
| Phenyl | 3-fluorophenyl | H | cyclopropylmethyl | 472.1 |
| Phenyl | 3-fluorophenyl | H | cyclopentyl | 486.1 |
| Phenyl | 3-fluorophenyl | H | 3,4-methylenedioxybenzyl | 552.1 |
| Phenyl | 3,4-difluorophenyl | H | H | 436.1 |
| Phenyl | 3,4-difluorophenyl | H | methyl | 450.1 |
| Phenyl | 3,4-difluorophenyl | H | cyclopropylmethyl | 490.1 |
| Phenyl | 3,4-difluorophenyl | H | cyclopentyl | 504.1 |
| Phenyl | 3,4-difluorophenyl | H | 3,4-methylenedioxybenzyl | 570.1 |
| 3-cyanophenyl | 2-fluorophenyl | H | cyclopropylmethyl | 497.1 |
| 3-cyanophenyl | 3-fluorophenyl | H | cyclopropylmethyl | 497.1 |
| 3-cyanophenyl | 4-fluorophenyl | H | cyclopropylmethyl | 497.1 |
| 3-cyanophenyl | 2-methoxyphenyl | H | cyclopropylmethyl | 509.1 |
| 3-cyanophenyl | 3-methoxyphenyl | H | cyclopropylmethyl | 509.1 |
| 3-cyanophenyl | 4-methoxyphenyl | H | cyclopropylmethyl | 509.1 |
| 3-cyanophenyl | 3,5-dimethoxyphenyl | H | cyclopropylmethyl | 539.1 |
| 3-cyanophenyl | 3-cyanophenyl | H | cyclopropylmethyl | 504.1 |
| 3-cyanophenyl | 4-cyanophenyl | H | cyclopropylmethyl | 504.1 |
| 3-cyanophenyl | 2-fluorophenyl | H | cyclopentyl | 511.1 |
| 3-cyanophenyl | 3-fluorophenyl | H | cyclopentyl | 511.1 |
| 3-cyanophenyl | 4-fluorophenyl | H | cyclopentyl | 511.1 |
| 3-cyanophenyl | 2-methoxyphenyl | H | cyclopentyl | 523.1 |
| 3-cyanophenyl | 4-methoxyphenyl | H | cyclopentyl | 523.1 |
| 3-cyanophenyl | 3,5-dimethoxyphenyl | H | cyclopentyl | 553.1 |
| 3-cyanophenyl | 3-cyanophenyl | H | cyclopentyl | 518.1 |
| 3-cyanophenyl | 4-cyanophenyl | H | cyclopentyl | 518.1 |
| 3-fluorophenyl | Phenyl | H | methyl | 432.1 |
| 3-fluorophenyl | 2-chlorophenyl | H | methyl | 466.11 |
| 3-fluorophenyl | 3-chlorophenyl | H | methyl | 466.11 |
| 3-fluorophenyl | 4-chlorophenyl | H | methyl | 466.11 |
| 3-fluorophenyl | 2-methoxyphenyl | H | methyl | 462.11 |
| 3-fluorophenyl | 3-methoxyphenyl | H | methyl | 462.11 |
| 3-fluorophenyl | 4-methoxyphenyl | H | methyl | 462.11 |
| 3-fluorophenyl | 3,4-methylenedioxyphenyl | H | methyl | 476.11 |
| 3-fluorophenyl | 2,5-dimethoxyphenyl | H | methyl | 492.12 |
| 3-fluorophenyl | 2,4-dimethoxyphenyl | H | methyl | 492.12 |
| 3-fluorophenyl | 3,5-dimethoxyphenyl | H | methyl | 492.12 |
| 3-fluorophenyl | 2-fluorophenyl | H | methyl | 450.11 |
| 3-fluorophenyl | 3-fluorophenyl | H | methyl | 450.11 |
| 3-fluorophenyl | 4-fluorophenyl | H | methyl | 450.11 |
| 3-fluorophenyl | 3-chloro,4-fluorophenyl | H | methyl | 484.12 |
| 3-fluorophenyl | 3,4-difluorophenyl | H | methyl | 468.11 |
| 3-fluorophenyl | 2,4-difluorophenyl | H | methyl | 468.11 |
| 3-fluorophenyl | 2,6-difluorophenyl | H | methyl | 468.11 |
| 3-fluorophenyl | 2-5-difluorophenyl | H | methyl | 468.11 |
| 3-fluorophenyl | 3-cyanophenyl | H | methyl | 457.11 |
| 3-fluorophenyl | 4-cyanophenyl | H | methyl | 457.11 |

-continued

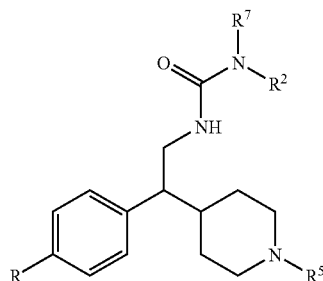

| R | R² | R⁷ | R⁵ | obs M + 1 m/z |
|---|---|---|---|---|
| 3-fluorophenyl | N, R2, R7 = pyrrolidine | N, R2, R7 = pyrrolidine | methyl | 410.1 |
| 3-fluorophenyl | N, R2, R7 = morpholine | N, R2, R7 = morpholine | methyl | 426.1 |
| 3-fluorophenyl | Phenyl | Methyl | methyl | 446.11 |
| 3-fluorophenyl | isopropyl | isopropyl | methyl | 440.11 |
| 3-fluorophenyl | Methyl | Methyl | methyl | 384.09 |
| 3-fluorophenyl | ethyl | ethyl | methyl | 412.1 |
| 3-fluorophenyl | Phenyl | H | cyclopropylmethyl | 472.11 |
| 3-fluorophenyl | 3,5-dichlorophenyl | H | cyclopropylmethyl | 540.13 |
| 3-fluorophenyl | 2-chlorophenyl | H | cyclopropylmethyl | 506.12 |
| 3-fluorophenyl | 3-chlorophenyl | H | cyclopropylmethyl | 506.12 |
| 3-fluorophenyl | 4-chlorophenyl | H | cyclopropylmethyl | 506.12 |
| 3-fluorophenyl | 2-methoxyphenyl | H | cyclopropylmethyl | 502.12 |
| 3-fluorophenyl | 3-methoxyphenyl | H | cyclopropylmethyl | 502.12 |
| 3-fluorophenyl | 4-methoxyphenyl | H | cyclopropylmethyl | 502.12 |
| 3-fluorophenyl | 3,4-methylenedioxyphenyl | H | cyclopropylmethyl | 516.12 |
| 3-fluorophenyl | 2,5-dimethoxyphenyl | H | cyclopropylmethyl | 532.13 |
| 3-fluorophenyl | 2,4-dimethoxyphenyl | H | cyclopropylmethyl | 532.13 |
| 3-fluorophenyl | 3,5-dimethoxyphenyl | H | cyclopropylmethyl | 532.13 |
| 3-fluorophenyl | 2-fluorophenyl | H | cyclopropylmethyl | 490.12 |
| 3-fluorophenyl | 3-fluorophenyl | H | cyclopropylmethyl | 490.12 |
| 3-fluorophenyl | 4-fluorophenyl | H | cyclopropylmethyl | 490.12 |
| 3-fluorophenyl | 3-chloro,4-fluorophenyl | H | cyclopropylmethyl | 524.12 |
| 3-fluorophenyl | 3,4-difluorophenyl | H | cyclopropylmethyl | 508.12 |
| 3-fluorophenyl | 2,4-difluorophenyl | H | cyclopropylmethyl | 508.12 |
| 3-fluorophenyl | 2,6-difluorophenyl | H | cyclopropylmethyl | 508.12 |
| 3-fluorophenyl | 2-5-difluorophenyl | H | cyclopropylmethyl | 508.12 |
| 3-fluorophenyl | 3-cyanophenyl | H | cyclopropylmethyl | 497.12 |
| 3-fluorophenyl | 4-cyanophenyl | H | cyclopropylmethyl | 497.12 |
| 3-fluorophenyl | N, R2, R7 = pyrrolidine | N, R2, R7 = pyrrolidine | cyclopropylmethyl | 450.11 |
| 3-fluorophenyl | N, R2, R7 = morpholine | N, R2, R7 = morpholine | cyclopropylmethyl | 466.11 |
| 3-fluorophenyl | Phenyl | Methyl | cyclopropylmethyl | 486.12 |
| 3-fluorophenyl | isopropyl | isopropyl | cyclopropylmethyl | 480.12 |
| 3-fluorophenyl | Methyl | Methyl | cyclopropylmethyl | 424.1 |
| 3-fluorophenyl | ethyl | ethyl | cyclopropylmethyl | 452.11 |
| 3-fluorophenyl | Phenyl | H | cyclopentyl | 486.12 |
| 3-fluorophenyl | 3,5-dichlorophenyl | H | cyclopentyl | 554.13 |
| 3-fluorophenyl | 2-chlorophenyl | H | cyclopentyl | 520.12 |
| 3-fluorophenyl | 3-chlorophenyl | H | cyclopentyl | 520.12 |
| 3-fluorophenyl | 4-chlorophenyl | H | cyclopentyl | 520.12 |
| 3-fluorophenyl | 2-methoxyphenyl | H | cyclopentyl | 516.12 |
| 3-fluorophenyl | 3-methoxyphenyl | H | cyclopentyl | 516.12 |
| 3-fluorophenyl | 4-methoxyphenyl | H | cyclopentyl | 516.12 |
| 3-fluorophenyl | 3,4-methylenedioxyphenyl | H | cyclopentyl | 530.13 |
| 3-fluorophenyl | 2,5-dimethoxyphenyl | H | cyclopentyl | 546.13 |
| 3-fluorophenyl | 2,4-dimethoxyphenyl | H | cyclopentyl | 546.13 |
| 3-fluorophenyl | 3,5-dimethoxyphenyl | H | cyclopentyl | 546.13 |
| 3-fluorophenyl | 2-fluorophenyl | H | cyclopentyl | 504.12 |
| 3-fluorophenyl | 3-fluorophenyl | H | cyclopentyl | 504.12 |
| 3-fluorophenyl | 4-fluorophenyl | H | cyclopentyl | 504.12 |
| 3-fluorophenyl | 3-chloro,4-fluorophenyl | H | cyclopentyl | 538.13 |
| 3-fluorophenyl | 3,4-difluorophenyl | H | cyclopentyl | 522.12 |
| 3-fluorophenyl | 2,4-difluorophenyl | H | cyclopentyl | 523.12 |

-continued

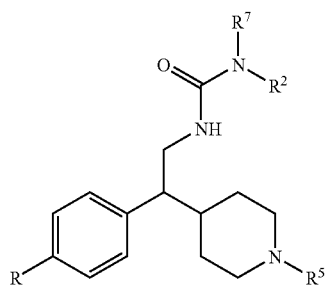

| R | R² | R⁷ | R⁵ | obs M + 1 m/z |
|---|---|---|---|---|
| 3-fluorophenyl | 2,6-difluorophenyl | H | cyclopentyl | 523.12 |
| 3-fluorophenyl | 2-5-difluorophenyl | H | cyclopentyl | 523.12 |
| 3-fluorophenyl | 3-cyanophenyl | H | cyclopentyl | 511.12 |
| 3-fluorophenyl | 4-cyanophenyl | H | cyclopentyl | 511.12 |
| 3-fluorophenyl | N, R2, R7 = pyrrolidine | N, R2, R7 = pyrrolidine | cyclopentyl | 464.11 |
| 3-fluorophenyl | N, R2, R7 = morpholine | N, R2, R7 = morpholine | cyclopentyl | 480.12 |
| 3-fluorophenyl | Phenyl | Methyl | cyclopentyl | 500.12 |
| 3-fluorophenyl | isopropyl | isopropyl | cyclopentyl | 494.12 |
| 3-fluorophenyl | Methyl | Methyl | cyclopentyl | 438.11 |
| 3-fluorophenyl | ethyl | ethyl | cyclopentyl | 466.11 |
| 3-fluorophenyl | Phenyl | H | 3,4-ethylenedioxybenzyl | 566.13 |
| 3-fluorophenyl | 3,5-dichlorophenyl | H | 3,4-ethylenedioxybenzyl | 634.15 |
| 3-fluorophenyl | 2-chlorophenyl | H | 3,4-ethylenedioxybenzyl | 600.14 |
| 3-fluorophenyl | 3-chlorophenyl | H | 3,4-ethylenedioxybenzyl | 600.14 |
| 3-fluorophenyl | 4-chlorophenyl | H | 3,4-ethylenedioxybenzyl | 600.14 |
| 3-fluorophenyl | 2-methoxyphenyl | H | 3,4-ethylenedioxybenzyl | 596.14 |
| 3-fluorophenyl | 3-methoxyphenyl | H | 3,4-ethylenedioxybenzyl | 596.14 |
| 3-fluorophenyl | 4-methoxyphenyl | H | 3,4-ethylenedioxybenzyl | 596.14 |
| 3-fluorophenyl | 3,4-methylenedioxyphenyl | H | 3,4-ethylenedioxybenzyl | 610.14 |
| 3-fluorophenyl | 2,5-dimethoxyphenyl | H | 3,4-ethylenedioxybenzyl | 626.15 |
| 3-fluorophenyl | 2,4-dimethoxyphenyl | H | 3,4-ethylenedioxybenzyl | 626.15 |
| 3-fluorophenyl | 3,5-dimethoxyphenyl | H | 3,4-ethylenedioxybenzyl | 626.15 |
| 3-fluorophenyl | 2-fluorophenyl | H | 3,4-ethylenedioxybenzyl | 584.14 |
| 3-fluorophenyl | 3-fluorophenyl | H | 3,4-ethylenedioxybenzyl | 584.14 |
| 3-fluorophenyl | 4-fluorophenyl | H | 3,4-ethylenedioxybenzyl | 584.14 |
| 3-fluorophenyl | 3-chloro,4-fluorophenyl | H | 3,4-ethylenedioxybenzyl | 618.14 |
| 3-fluorophenyl | 3,4-difluorophenyl | H | 3,4-ethylenedioxybenzyl | 602.14 |
| 3-fluorophenyl | 2,4-difluorophenyl | H | 3,4-ethylenedioxybenzyl | 602.14 |
| 3-fluorophenyl | 2,6-difluorophenyl | H | 3,4-ethylenedioxybenzyl | 602.14 |
| 3-fluorophenyl | 2-5-difluorophenyl | H | 3,4-ethylenedioxybenzyl | 602.14 |
| 3-fluorophenyl | 3-cyanophenyl | H | 3,4-ethylenedioxybenzyl | 591.14 |
| 3-fluorophenyl | 4-cyanophenyl | H | 3,4-ethylenedioxybenzyl | 591.14 |
| 3-fluorophenyl | N, R2, R7 = pyrrolidine | N, R2, R7 = pyrrolidine | 3,4-ethylenedioxybenzyl | 544.13 |
| 3-fluorophenyl | N, R2, R7 = morpholine | N, R2, R7 = morpholine | 3,4-ethylenedioxybenzyl | 560.13 |
| 3-fluorophenyl | Phenyl | Methyl | 3,4-ethylenedioxybenzyl | 580.14 |
| 3-fluorophenyl | isopropyl | isopropyl | 3,4-ethylenedioxybenzyl | 574.13 |
| 3-fluorophenyl | Methyl | Methyl | 3,4-ethylenedioxybenzyl | 518.12 |
| 3-fluorophenyl | ethyl | ethyl | 3,4-ethylenedioxybenzyl | 546.13 |
| 3-cyanophenyl | Phenyl | H | methyl | 439.11 |
| 3-cyanophenyl | 2-chlorophenyl | H | methyl | 473.11 |
| 3-cyanophenyl | 3-chlorophenyl | H | methyl | 473.11 |
| 3-cyanophenyl | 4-chlorophenyl | H | methyl | 473.11 |
| 3-cyanophenyl | 2-methoxyphenyl | H | methyl | 469.11 |
| 3-cyanophenyl | 3-methoxyphenyl | H | methyl | 469.11 |
| 3-cyanophenyl | 4-methoxyphenyl | H | methyl | 469.11 |
| 3-cyanophenyl | 3,4-methylenedioxyphenyl | H | methyl | 483.12 |
| 3-cyanophenyl | 2,5-dimethoxyphenyl | H | methyl | 499.12 |
| 3-cyanophenyl | 2,4-dimethoxyphenyl | H | methyl | 499.12 |
| 3-cyanophenyl | 3,5-dimethoxyphenyl | H | methyl | 499.12 |
| 3-cyanophenyl | 2-fluorophenyl | H | methyl | 457.11 |
| 3-cyanophenyl | 3-fluorophenyl | H | methyl | 457.11 |
| 3-cyanophenyl | 4-fluorophenyl | H | methyl | 457.11 |
| 3-cyanophenyl | 3,4-difluorophenyl | H | methyl | 475.11 |

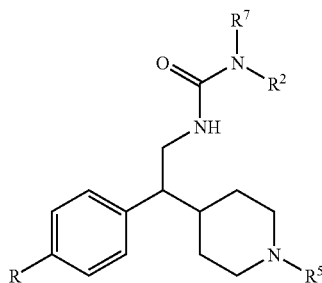

| R | R² | R⁷ | R⁵ | obs M + 1 m/z |
|---|---|---|---|---|
| 3-cyanophenyl | 2,4-difluorophenyl | H | methyl | 475.11 |
| 3-cyanophenyl | 2,6-difluorophenyl | H | methyl | 475.11 |
| 3-cyanophenyl | 2-5-difluorophenyl | H | methyl | 475.11 |
| 3-cyanophenyl | 3-cyanophenyl | H | methyl | 464.11 |
| 3-cyanophenyl | 4-cyanophenyl | H | methyl | 464.11 |
| 3-cyanophenyl | N, R2, R7 = pyrrolidine | N, R2, R7 = pyrrolidine | methyl | 417.1 |
| 3-cyanophenyl | N, R2, R7 = morpholine | N, R2, R7 = morpholine | methyl | 433.11 |
| 3-cyanophenyl | Phenyl | Methyl | methyl | 453.11 |
| 3-cyanophenyl | isopropyl | isopropyl | methyl | 447.11 |
| 3-cyanophenyl | Methyl | Methyl | methyl | 391.1 |
| 3-cyanophenyl | ethyl | ethyl | methyl | 419.1 |
| 3-cyanophenyl | Phenyl | H | cyclopropylmethyl | 479.11 |
| 3-cyanophenyl | 2-chlorophenyl | H | cyclopropylmethyl | 513.12 |
| 3-cyanophenyl | 3-chlorophenyl | H | cyclopropylmethyl | 513.12 |
| 3-cyanophenyl | 4-chlorophenyl | H | cyclopropylmethyl | 513.12 |
| 3-cyanophenyl | 3,4-methylenedioxyphenyl | H | cyclopropylmethyl | 523.12 |
| 3-cyanophenyl | 2,5-dimethoxyphenyl | H | cyclopropylmethyl | 539.13 |
| 3-cyanophenyl | 2,4-dimethoxyphenyl | H | cyclopropylmethyl | 539.13 |
| 3-cyanbphenyl | 3-chloro,4-fluorophenyl | H | cyclopropylmethyl | 531.13 |
| 3-cyanophenyl | 3,4-difluorophenyl | H | cyclopropylmethyl | 515.12 |
| 3-cyanophenyl | 2,4-difluorophenyl | H | cyclopropylmethyl | 515.12 |
| 3-cyanophenyl | 2,6-difluorophenyl | H | cyclopropylmethyl | 515.12 |
| 3-cyanophenyl | 2-5-difluorophenyl | H | cyclopropylmethyl | 515.12 |
| 3-cyanophenyl | N, R2, R7 = pyrrolidine | N, R2, R7 = pyrrolidine | cyclopropylmethyl | 457.11 |
| 3-cyanophenyl | N, R2, R7 = morpholine | N, R2, R7 = morpholine | cyclopropylmethyl | 473.11 |
| 3-cyanophenyl | Phenyl | Methyl | cyclopropylmethyl | 493.12 |
| 3-cyanophenyl | isopropyl | isopropyl | cyclopropylmethyl | 487.12 |
| 3-cyanophenyl | Methyl | Methyl | cyclopropylmethyl | 431.1 |
| 3-cyanophenyl | ethyl | ethyl | cyclopropylmethyl | 459.11 |
| 3-cyanophenyl | Phenyl | H | cyclopentyl | 493.12 |
| 3-cyanophenyl | 2-chlorophenyl | H | cyclopentyl | 527.12 |
| 3-cyanophenyl | 4-chlorophenyl | H | cyclopentyl | 527.12 |
| 3-cyanophenyl | 3,4-methylenedioxyphenyl | H | cyclopentyl | 537.13 |
| 3-cyanophenyl | 2,5-dimethoxyphenyl | H | cyclopentyl | 553.13 |
| 3-cyanophenyl | 2,4-dimethoxyphenyl | H | cyclopentyl | 553.13 |
| 3-cyanophenyl | 3-chloro,4-fluorophenyl | H | cyclopentyl | 545.13 |
| 3-cyanophenyl | 3,4-difluorophenyl | H | cyclopentyl | 529.13 |
| 3-cyanophenyl | 2,4-difluorophenyl | H | cyclopentyl | 529.13 |
| 3-cyanophenyl | 2,6-difluorophenyl | H | cyclopentyl | 529.13 |
| 3-cyanophenyl | 2-5-difluorophenyl | H | cyclopentyl | 529.13 |
| 3-cyanophenyl | N, R2, R7 = pyrrolidine | N, R2, R7 = pyrrolidine | cyclopentyl | 471.11 |
| 3-cyanophenyl | N, R2, R7 = morpholine | N, R2, R7 = morpholine | cyclopentyl | 487.12 |
| 3-cyanophenyl | Phenyl | Methyl | cyclopentyl | 507.12 |
| 3-cyanophenyl | isopropyl | isopropyl | cyclopentyl | 501.12 |
| 3-cyanophenyl | Methyl | Methyl | cyclopentyl | 445.11 |
| 3-cyanophenyl | ethyl | ethyl | cyclopentyl | 473.11 |
| 3-cyanophenyl | Phenyl | H | 3,4-ethylenedioxybenzyl | 573.13 |
| 3-cyanophenyl | 2-chlorophenyl | H | 3,4-ethylenedioxybenzyl | 607.1 |
| 3-cyanophenyl | 3-chlorophenyl | H | 3,4-ethylenedioxybenzyl | 607.14 |
| 3-cyanophenyl | 4-chlorophenyl | H | 3,4-ethylenedioxybenzyl | 607.14 |

-continued

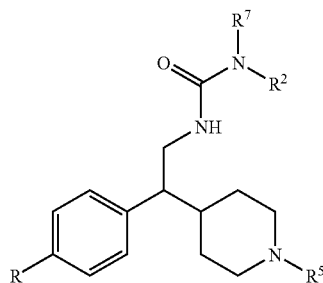

| R | R² | R⁷ | R⁵ | obs M + 1 m/z |
|---|---|---|---|---|
| 3-cyanophenyl | 2-methoxyphenyl | H | 3,4-ethylenedioxybenzyl | 603.1 |
| 3-cyanophenyl | 3-methoxyphenyl | H | 3,4-ethylenedioxybenzyl | 603.14 |
| 3-cyanophenyl | 4-methoxyphenyl | H | 3,4-ethylenedioxybenzyl | 603.14 |
| 3-cyanophenyl | 3,4-methylenedioxyphenyl | H | 3,4-ethylenedioxybenzyl | 617.1 |
| 3-cyanophenyl | 2,5-dimethoxyphenyl | H | 3,4-ethylenedioxybenzyl | 633.15 |
| 3-cyanophenyl | 2,4-dimethoxyphenyl | H | 3,4-ethylenedioxybenzyl | 633.15 |
| 3-cyanophenyl | 3,5-dimethoxyphenyl | H | 3,4-ethylenedioxybenzyl | 633.15 |
| 3-cyanophenyl | 2-fluorophenyl | H | 3,4-ethylenedioxybenzyl | 591.14 |
| 3-cyanophenyl | 3-fluorophenyl | H | 3,4-ethylenedioxybenzyl | 591.14 |
| 3-cyanophenyl | 4-fluorophenyl | H | 3,4-ethylenedioxybenzyl | 591.14 |
| 3-cyanophenyl | 3-chloro,4-fluorophenyl | H | 3,4-ethylenedioxybenzyl | 625.15 |
| 3-cyanophenyl | 3,4-difluorophenyl | H | 3,4-ethylenedioxybenzyl | 609.14 |
| 3-cyanophenyl | 2,4-difluorophenyl | H | 3,4-ethylenedioxybenzyl | 609.14 |
| 3-cyanophenyl | 2,6-difluorophenyl | H | 3,4-ethylenedioxybenzyl | 609.14 |
| 3-cyanophenyl | 2-5-difluorophenyl | H | 3,4-ethylenedioxybenzyl | 609.14 |
| 3-cyanophenyl | 3-cyanophenyl | H | 3,4-ethylenedioxybenzyl | 598.14 |
| 3-cyanophenyl | 4-cyanophenyl | H | 3,4-ethylenedioxybenzyl | 598.14 |
| 3-cyanophenyl | N, R2, R7 = pyrrolidine | N, R2, R7 = pyrrolidine | 3,4-ethylenedioxybenzyl | 551.13 |
| 3-cyanophenyl | N, R2, R7 = morpholine | N, R2, R7 = morpholine | 3,4-ethylenedioxybenzyl | 567.13 |
| 3-cyanophenyl | Phenyl | Methyl | 3,4-ethylenedioxybenzyl | 587.14 |
| 3-cyanophenyl | isopropyl | isopropyl | 3,4-ethylenedioxybenzyl | 581.14 |
| 3-cyanophenyl | Methyl | Methyl | 3,4-ethylenedioxybenzyl | 525.1 |
| 3-cyanophenyl | ethyl | ethyl | 3,4-ethylenedioxybenzyl | 553.13 |
| 3,4-methylenedioxyphenyl | Phenyl | H | methyl | 458.11 |
| 3,4-methylenedioxyphenyl | 3,5-dichlorophenyl | H | methyl | 526.12 |
| 3,4-methylenedioxyphenyl | 2-chlorophenyl | H | methyl | 492.12 |
| 3,4-methylenedioxyphenyl | 3-chlorophenyl | H | methyl | 492.12 |
| 3,4-methylenedioxyphenyl | 4-chlorophenyl | H | methyl | 492.12 |
| 3,4-methylenedioxyphenyl | 2-methoxyphenyl | H | methyl | 488.12 |
| 3,4-methylenedioxyphenyl | 3-methoxyphenyl | H | methyl | 488.12 |
| 3,4-methylenedioxyphenyl | 4-methoxyphenyl | H | methyl | 488.12 |
| 3,4-methylenedioxyphenyl | 3,4-methylenedioxyphenyl | H | methyl | 502.12 |
| 3,4-methylenedioxyphenyl | 2,5-dimethoxyphenyl | H | methyl | 518.12 |
| 3,4-methylenedioxyphenyl | 2,4-dimethoxyphenyl | H | methyl | 518.12 |
| 3,4-methylenedioxyphenyl | 3,5-dimethoxyphenyl | H | methyl | 518.12 |
| 3,4-methylenedioxyphenyl | 2-fluorophenyl | H | methyl | 476.11 |
| 3,4-methylenedioxyphenyl | 3-fluorophenyl | H | methyl | 476.11 |
| 3,4-methylenedioxyphenyl | 4-fluorophenyl | H | methyl | 476.11 |
| 3,4-methylenedioxyphenyl | 3-chloro,4-fluorophenyl | H | methyl | 510.12 |

-continued

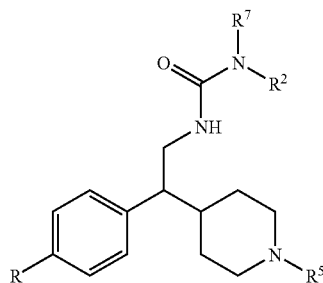

| R | R² | R⁷ | R⁵ | obs M + 1 m/z |
|---|---|---|---|---|
| 3,4-methylenedioxyphenyl | 3,4-difluorophenyl | H | methyl | 494.12 |
| 3,4-methylenedioxyphenyl | 2,4-difluorophenyl | H | methyl | 494.12 |
| 3,4-methylenedioxyphenyl | 2,6-difluorophenyl | H | methyl | 494.12 |
| 3,4-methylenedioxyphenyl | 2-5-difluorophenyl | H | methyl | 494.12 |
| 3,4-methylenedioxyphenyl | 3-cyanophenyl | H | methyl | 483.12 |
| 3,4-methylenedioxyphenyl | 4-cyanophenyl | H | methyl | 483.12 |
| 3,4-methylenedioxyphenyl | N, R2, R7 = pyrrolidine | N, R2, R7 = pyrrolidine | methyl | 436.11 |
| 3,4-methylenedioxyphenyl | N, R2, R7 = morpholine | N, R2, R7 = morpholine | methyl | 452.11 |
| 3,4-methylenedioxyphenyl | Phenyl | Methyl | methyl | 472.11 |
| 3,4-methylenedioxyphenyl | isopropyl | isopropyl | methyl | 466.11 |
| 3,4-methylenedioxyphenyl | Methyl | Methyl | methyl | 410.1 |
| 3,4-methylenedioxyphenyl | ethyl | ethyl | methyl | 438.11 |
| 3,4-methylenedioxyphenyl | Phenyl | H | cyclopropylmethyl | 498.12 |
| 3,4-methylenedioxyphenyl | 3,5-dichlorophenyl | H | cyclopropylmethyl | 566.13 |
| 3,4-methylenedioxyphenyl | 2-chlorophenyl | H | cyclopropylmethyl | 532.13 |
| 3,4-methylenedioxyphenyl | 3-chlorophenyl | H | cyclopropylmethyl | 532.13 |
| 3,4-methylenedioxyphenyl | 4-chlorophenyl | H | cyclopropylmethyl | 532.13 |
| 3,4-methylenedioxyphenyl | 2-methoxyphenyl | H | cyclopropylmethyl | 528.13 |
| 3,4-methylenedioxyphenyl | 3-methoxyphenyl | H | cyclopropylmethyl | 528.13 |
| 3,4-methylenedioxyphenyl | 4-methoxyphenyl | H | cyclopropylmethyl | 528.13 |
| 3,4-methylenedioxyphenyl | 3,4-methylenedioxyphenyl | H | cyclopropylmethyl | 542.13 |
| 3,4-methylenedioxyphenyl | 2,5-dimethoxyphenyl | H | cyclopropylmethyl | 558.13 |
| 3,4-methylenedioxyphenyl | 2,4-dimethoxyphenyl | H | cyclopropylmethyl | 558.13 |
| 3,4-methylenedioxyphenyl | 3,5-dimethoxyphenyl | H | cyclopropylmethyl | 558.13 |
| 3,4-methylenedioxyphenyl | 2-fluorophenyl | H | cyclopropylmethyl | 516.12 |
| 3,4-methylenedioxyphenyl | 3-fluorophenyl | H | cyclopropylmethyl | 516.12 |
| 3,4-methylenedioxyphenyl | 4-fluorophenyl | H | cyclopropylmethyl | 516.12 |
| 3,4-methylenedioxyphenyl | 3-chloro,4-fluorophenyl | H | cyclopropylmethyl | 550.13 |
| 3,4-methylenedioxyphenyl | 3,4-difluorophenyl | H | cyclopropylmethyl | 534.13 |
| 3,4-methylenedioxyphenyl | 2,4-difluorophenyl | H | cyclopropylmethyl | 534.13 |

-continued

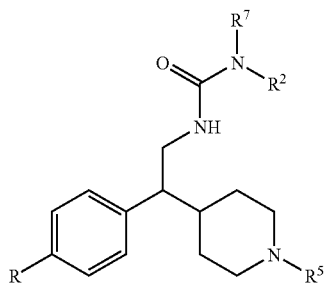

| R | R² | R⁷ | R⁵ | obs M+1 m/z |
|---|---|---|---|---|
| 3,4-methylenedioxyphenyl | 2,6-difluorophenyl | H | cyclopropylmethyl | 534.13 |
| 3,4-methylenedioxyphenyl | 2-5-difluorophenyl | H | cyclopropylmethyl | 534.13 |
| 3,4-methylenedioxyphenyl | 3-cyanophenyl | H | cyclopropylmethyl | 523.12 |
| 3,4-methylenedioxyphenyl | 4-cyanophenyl | H | cyclopropylmethyl | 523.12 |
| 3,4-methylenedioxyphenyl | N, R2, R7 = pyrrolidine | N, R2, R7 = pyrrolidine | cyclopropylmethyl | 476.11 |
| 3,4-methylenedioxyphenyl | N, R2, R7 = morpholine | N, R2, R7 = morpholine | cyclopropylmethyl | 492.12 |
| 3,4-methylenedioxyphenyl | Phenyl | Methyl | cyclopropylmethyl | 512.12 |
| 3,4-methylenedioxyphenyl | isopropyl | isopropyl | cyclopropylmethyl | 506.12 |
| 3,4-methylenedioxyphenyl | Methyl | Methyl | cyclopropylmethyl | 450.11 |
| 3,4-methylenedioxyphenyl | ethyl | ethyl | cyclopropylmethyl | 478.11 |
| 3,4-methylenedioxyphenyl | Phenyl | H | cyclopentyl | 512.12 |
| 3,4-methylenedioxyphenyl | 3,5-dichlorophenyl | H | cyclopentyl | 580.14 |
| 3,4-methylenedioxyphenyl | 2-chlorophenyl | H | cyclopentyl | 546.13 |
| 3,4-methylenedioxyphenyl | 3-chlorophenyl | H | cyclopentyl | 546.13 |
| 3,4-methylenedioxyphenyl | 4-chlorophenyl | H | cyclopentyl | 546.13 |
| 3,4-methylenedioxyphenyl | 2-methoxyphenyl | H | cyclopentyl | 542.13 |
| 3,4-methylenedioxyphenyl | 3-methoxyphenyl | H | cyclopentyl | 542.13 |
| 3,4-methylenedioxyphenyl | 4-methoxyphenyl | H | cyclopentyl | 542.13 |
| 3,4-methylenedioxyphenyl | 3,4-methylenedioxyphenyl | H | cyclopentyl | 556.13 |
| 3,4-methylenedioxyphenyl | 2,5-dimethoxyphenyl | H | cyclopentyl | 572.13 |
| 3,4-methylenedioxyphenyl | 2,4-dimethoxyphenyl | H | cyclopentyl | 572.13 |
| 3,4-methylenedioxyphenyl | 3,5-dimethoxyphenyl | H | cyclopentyl | 572.13 |
| 3,4-methylenedioxyphenyl | 2-fluorophenyl | H | cyclopentyl | 530.13 |
| 3,4-methylenedioxyphenyl | 3-fluorophenyl | H | cyclopentyl | 530.13 |
| 3,4-methylenedioxyphenyl | 4-fluorophenyl | H | cyclopentyl | 530.13 |
| 3,4-methylenedioxyphenyl | 3-chloro,4-fluorophenyl | H | cyclopentyl | 564.13 |
| 3,4-methylenedioxyphenyl | 3,4-difluorophenyl | H | cyclopentyl | 548.13 |
| 3,4-methylenedioxyphenyl | 2,4-difluorophenyl | H | cyclopentyl | 548.13 |
| 3,4-methylenedioxyphenyl | 2,6-difluorophenyl | H | cyclopentyl | 548.13 |
| 3,4-methylenedioxyphenyl | 2-5-difluorophenyl | H | cyclopentyl | 548.13 |

-continued

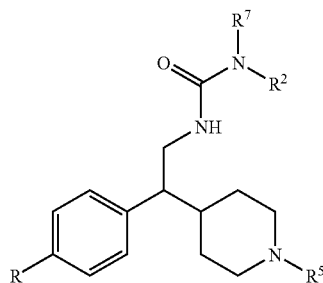

| R | R² | R⁷ | R⁵ | obs M + 1 m/z |
|---|---|---|---|---|
| 3,4-methylenedioxyphenyl | 3-cyanophenyl | H | cyclopentyl | 537.13 |
| 3,4-methylenedioxyphenyl | 4-cyanophenyl | H | cyclopentyl | 537.13 |
| 3,4-methylenedioxyphenyl | N, R2, R7 = pyrrolidine | N, R2, R7 = pyrrolidine | cyclopentyl | 490.12 |
| 3,4-methylenedioxyphenyl | N, R2, R7 = morpholine | N, R2, R7 = morpholine | cyclopentyl | 506.12 |
| 3,4-methylenedioxyphenyl | Phenyl | Methyl | cyclopentyl | 526.12 |
| 3,4-methylenedioxyphenyl | isopropyl | isopropyl | cyclopentyl | 520.12 |
| 3,4-methylenedioxyphenyl | Methyl | Methyl | cyclopentyl | 464.11 |
| 3,4-methylenedioxyphenyl | ethyl | ethyl | cyclopentyl | 492.12 |
| 3,4-methylenedioxyphenyl | Phenyl | H | 3,4-ethylenedioxybenzyl | 592.14 |
| 3,4-methylenedioxyphenyl | 3,5-dichlorophenyl | H | 3,4-ethylenedioxybenzyl | 660.16 |
| 3,4-methylenedioxyphenyl | 2-chlorophenyl | H | 3,4-ethylenedioxybenzyl | 626.15 |
| 3,4-methylenedioxyphenyl | 3-chlorophenyl | H | 3,4-ethylenedioxybenzyl | 626.15 |
| 3,4-methylenedioxyphenyl | 4-chlorophenyl | H | 3,4-ethylenedioxybenzyl | 626.15 |
| 3,4-methylenedioxyphenyl | 2-methoxyphenyl | H | 3,4-ethylenedioxybenzyl | 622.15 |
| 3,4-methylenedioxyphenyl | 3-methoxyphenyl | H | 3,4-ethylenedioxybenzyl | 622.15 |
| 3,4-methylenedioxyphenyl | 4-methoxyphenyl | H | 3,4-ethylenedioxybenzyl | 622.15 |
| 3,4-methylenedioxyphenyl | 3,4-methylenedioxyphenyl | H | 3,4-ethylenedioxybenzyl | 636.15 |
| 3,4-methylenedioxyphenyl | 2,5-dimethoxyphenyl | H | 3,4-ethylenedioxybenzyl | 652.16 |
| 3,4-methylenedioxyphenyl | 2,4-dimethoxyphenyl | H | 3,4-ethylenedioxybenzyl | 652.16 |
| 3,4-methylenedioxyphenyl | 3,5-dimethoxyphenyl | H | 3,4-ethylenedioxybenzyl | 652.16 |
| 3,4-methylenedioxyphenyl | 2-fluorophenyl | H | 3,4-ethylenedioxybenzyl | 610.14 |
| 3,4-methylenedioxyphenyl | 3-fluorophenyl | H | 3,4-ethylenedioxybenzyl | 610.14 |
| 3,4-methylenedioxyphenyl | 4-fluorophenyl | H | 3,4-ethylenedioxybenzyl | 610.14 |
| 3,4-methylenedioxyphenyl | 3-chloro,4-fluorophenyl | H | 3,4-ethylenedioxybenzyl | 644.15 |
| 3,4-methylenedioxyphenyl | 3,4-difluorophenyl | H | 3,4-ethylenedioxybenzyl | 628.15 |
| 3,4-methylenedioxyphenyl | 2,4-difluorophenyl | H | 3,4-ethylenedioxybenzyl | 628.15 |
| 3,4-methylenedioxyphenyl | 2,6-difluorophenyl | H | 3,4-ethylenedioxybenzyl | 628.15 |
| 3,4-methylenedioxyphenyl | 2-5-difluorophenyl | H | 3,4-ethylenedioxybenzyl | 628.15 |
| 3,4-methylenedioxyphenyl | 3-cyanophenyl | H | 3,4-ethylenedioxybenzyl | 617.14 |
| 3,4-methylenedioxyphenyl | 4-cyanophenyl | H | 3,4-ethylenedioxybenzyl | 617.14 |

-continued

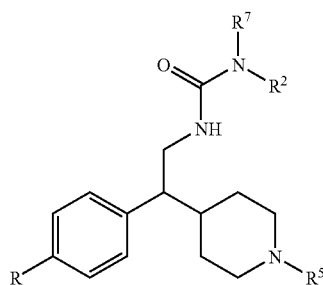

| R | R² | R⁷ | R⁵ | obs M+1 m/z |
|---|---|---|---|---|
| 3,4-methylenedioxyphenyl | N, R2, R7 = pyrrolidine | N, R2, R7 = pyrrolidine | 3,4-ethylenedioxybenzyl | 570.13 |
| 3,4-methylenedioxyphenyl | N, R2, R7 = morpholine | N, R2, R7 = morpholine | 3,4-ethylenedioxybenzyl | 586.14 |
| 3,4-methylenedioxyphenyl | Phenyl | Methyl | 3,4-ethylenedioxybenzyl | 606.14 |
| 3,4-methylenedioxyphenyl | isopropyl | isopropyl | 3,4-ethylenedioxybenzyl | 600.14 |
| 3,4-methylenedioxyphenyl | Methyl | Methyl | 3,4-ethylenedioxybenzyl | 544.13 |
| 3,4-methylenedioxyphenyl | ethyl | ethyl | 3,4-ethylenedioxybenzyl | 572.13 |
| 3-chlorophenyl | 4-chlorophenyl | H | methyl | 482.12 |
| 3-methoxyphenyl | 2-fluorophenyl | H | 3,4-ethylenedioxybenzyl | 596.14 |
| 3-methoxyphenyl | 3-cyanophenyl | H | 3,4-ethylenedioxybenzyl | 603.14 |
| 3-chlorophenyl | Phenyl | H | methyl | 448.11 |
| 3-chlorophenyl | 2-methoxyphenyl | H | methyl | 478.11 |
| 3-methoxyphenyl | 2,4-difluorophenyl | H | 3,4-ethylenedioxybenzyl | 614.14 |
| 3-methoxyphenyl | 2-5-difluorophenyl | H | 3,4-ethylenedioxybenzyl | 614.14 |
| 3-chlorophenyl | 2-chlorophenyl | H | cyclopropylmethyl | 522.12 |
| 3-methoxyphenyl | N, R2, R7 = morpholine | N, R2, R7 = morpholine | cyclopropylmethyl | 478.11 |
| 3-methoxyphenyl | 4-cyanophenyl | H | 3,4-ethylenedioxybenzyl | 603.14 |
| 3-methoxyphenyl | 2-methoxyphenyl | H | 3,4-ethylenedioxybenzyl | 608.14 |
| 3-methoxyphenyl | 4-methoxyphenyl | H | 3,4-ethylenedioxybenzyl | 608.14 |
| 3-methoxyphenyl | N, R2, R7 = pyrrolidine | N, R2, R7 = pyrrolidine | 3,4-ethylenedioxybenzyl | 556.13 |
| 3-chlorophenyl | Phenyl | Methyl | methyl | 462.11 |
| 3-chlorophenyl | 4-chlorophenyl | H | cyclopropylmethyl | 522.12 |
| 3-methoxyphenyl | 4-chlorophenyl | H | cyclopentyl | 532.13 |
| 3-methoxyphenyl | ethyl | ethyl | 3,4-ethylenedioxybenzyl | 558.13 |
| 3-chlorophenyl | 2-fluorophenyl | H | methyl | 466.11 |
| 3-chlorophenyl | 3-fluorophenyl | H | methyl | 466.11 |
| 3-chlorophenyl | 2-chlorophenyl | H | methyl | 482.12 |
| 3-chlorophenyl | 3-chlorophenyl | H | methyl | 482.12 |
| 3-chlorophenyl | 2,6-difluorophenyl | H | methyl | 484.12 |
| 3-methoxyphenyl | 3-fluorophenyl | H | 3,4-ethylenedioxybenzyl | 596.14 |
| 3-chlorophenyl | 4-cyanophenyl | H | methyl | 473.11 |
| 3-methoxyphenyl | Phenyl | Methyl | 3,4-ethylenedioxybenzyl | 592.14 |
| 3-methoxyphenyl | 3,5-dichlorophenyl | H | methyl | 512.12 |
| 3-methoxyphenyl | 4-cyanophenyl | H | cyclopropylmethyl | 509.12 |
| 3-methoxyphenyl | 3-cyanophenyl | H | cyclopentyl | 523.12 |
| 3-methoxyphenyl | 3-chloro,4-fluorophenyl | H | 3,4-ethylenedioxybenzyl | 630.15 |
| 3-chlorophenyl | 2-methoxyphenyl | H | cyclopropylmethyl | 518.12 |
| 3-chlorophenyl | 3,5-dichlorophenyl | H | cyclopropylmethyl | 552.13 |
| 3-methoxyphenyl | Phenyl | H | cyclopentyl | 498.12 |
| 3-methoxyphenyl | 3-chloro,4-fluorophenyl | H | cyclopentyl | 550.13 |
| 3-methoxyphenyl | N, R2, R7 = morpholine | N, R2, R7 = morpholine | cyclopentyl | 492.12 |
| 3-chlorophenyl | 2,5-dimethoxyphenyl | H | methyl | 508.12 |
| 3-methoxyphenyl | 4-chlorophenyl | H | cyclopropylmethyl | 518.12 |
| 3-chlorophenyl | 3,4-difluorophenyl | H | methyl | 484.12 |
| 3-chlorophenyl | Phenyl | H | cyclopropylmethyl | 488.12 |
| 3-methoxyphenyl | 2,6-difluorophenyl | H | cyclopentyl | 534.13 |
| 3-methoxyphenyl | Methyl | Methyl | 3,4-ethylenedioxybenzyl | 530.13 |
| 3-chlorophenyl | 4-methoxyphenyl | H | cyclopropylmethyl | 518.12 |
| 3-methoxyphenyl | 3-chloro,4-fluorophenyl | H | methyl | 496.12 |

-continued

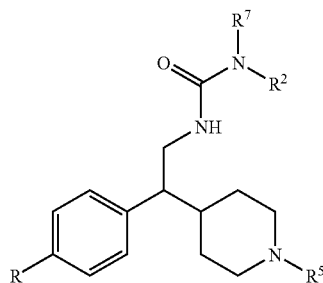

| R | R² | R⁷ | R⁵ | obs M + 1 m/z |
|---|---|---|---|---|
| 3-methoxyphenyl | 3-chlorophenyl | H | cyclopentyl | 532.13 |
| 3-methoxyphenyl | 4-fluorophenyl | H | 3,4-ethylenedioxybenzyl | 596.14 |
| 3-chlorophenyl | 4-fluorophenyl | H | methyl | 466.11 |
| 3-methoxyphenyl | Phenyl | H | methyl | 444.11 |
| 3-methoxyphenyl | 2,4-difluorophenyl | H | cyclopropylmethyl | 520.12 |
| 3-methoxyphenyl | 2-methoxyphenyl | H | methyl | 474.11 |
| 3-methoxyphenyl | 2,6-difluorophenyl | H | cyclopropylmethyl | 520.12 |
| 3-methoxyphenyl | 2-chlorophenyl | H | 3,4-ethylenedioxybenzyl | 612.14 |
| 3-methoxyphenyl | 2,5-dimethoxyphenyl | H | 3,4-ethylenedioxybenzyl | 638.15 |
| 3-chlorophenyl | ethyl | ethyl | methyl | 428.1 |
| 3-methoxyphenyl | 4-chlorophenyl | H | methyl | 478.11 |
| 3-methoxyphenyl | 2,4-difluorophenyl | H | methyl | 480.12 |
| 3-methoxyphenyl | 2-chlorophenyl | H | cyclopentyl | 532.13 |
| 3-methoxyphenyl | 2-chlorophenyl | H | cyclopropylmethyl | 518.12 |
| 3-methoxyphenyl | 4-methoxyphenyl | H | cyclopentyl | 528.13 |
| 3-methoxyphenyl | 4-chlorophenyl | H | 3,4-ethylenedioxybenzyl | 612.14 |
| 3-methoxyphenyl | 2,6-difluorophenyl | H | 3,4-ethylenedioxybenzyl | 614.14 |
| 3-chlorophenyl | 3,4-methylenedioxyphenyl | H | methyl | 492.12 |
| 3-methoxyphenyl | 2,4-dimethoxyphenyl | H | cyclopentyl | 558.13 |
| 3-chlorophenyl | 3-chlorophenyl | H | cyclopropylmethyl | 522.12 |
| 3-methoxyphenyl | 2-fluorophenyl | H | methyl | 462.11 |
| 3-methoxyphenyl | 3-cyanophenyl | H | methyl | 469.11 |
| 3-methoxyphenyl | 3-cyanophenyl | H | cyclopropylmethyl | 509.12 |
| 3-methoxyphenyl | 3,4-difluorophenyl | H | 3,4-ethylenedioxybenzyl | 614.14 |
| 3-methoxyphenyl | 2-chlorophenyl | H | methyl | 478.11 |
| 3-methoxyphenyl | 3,4-difluorophenyl | H | methyl | 480.12 |
| 3-methoxyphenyl | 2,6-difluorophenyl | H | methyl | 480.12 |
| 3-methoxyphenyl | N, R2, R7 = pyrrolidine | N, R2, R7 = pyrrolidine | methyl | 422.1 |
| 3-methoxyphenyl | 4-fluorophenyl | H | cyclopropylmethyl | 502.12 |
| 3-methoxyphenyl | Phenyl | Methyl | cyclopentyl | 512.12 |
| 3-chlorophenyl | 2,4-dimethoxyphenyl | H | methyl | 508.12 |
| 3-methoxyphenyl | 3,4-methylenedioxyphenyl | H | cyclopropylmethyl | 528.13 |
| 3-methoxyphenyl | 3-chloro,4-fluorophenyl | H | cyclopropylmethyl | 536.13 |
| 3-methoxyphenyl | 2-5-difluorophenyl | H | cyclopropylmethyl | 520.12 |
| 3-methoxyphenyl | 3,4-methylenedioxyphenyl | H | cyclopentyl | 542.13 |
| 3-methoxyphenyl | 3,4-difluorophenyl | H | cyclopentyl | 534.13 |
| 3-methoxyphenyl | ethyl | ethyl | cyclopentyl | 478.11 |
| 3-methoxyphenyl | Phenyl | H | 3,4-ethylenedioxybenzyl | 578.14 |
| 3-methoxyphenyl | 3-methoxyphenyl | H | 3,4-ethylenedioxybenzyl | 608.14 |
| 3-methoxyphenyl | 3,5-dimethoxyphenyl | H | 3,4-ethylenedioxybenzyl | 638.15 |
| 3-chlorophenyl | 3-methoxyphenyl | H | methyl | 478.11 |
| 3-chlorophenyl | 3,5-dimethoxyphenyl | H | methyl | 508.12 |
| 3-methoxyphenyl | 2-5-difluorophenyl | H | methyl | 480.12 |
| 3-methoxyphenyl | 2-fluorophenyl | H | cyclopropylmethyl | 502.12 |
| 3-methoxyphenyl | 3,5-dichlorophenyl | H | cyclopentyl | 566.13 |
| 3-chlorophenyl | Methyl | Methyl | methyl | 400.1 |
| 3-methoxyphenyl | 3,4-methylenedioxyphenyl | H | methyl | 488.12 |
| 3-methoxyphenyl | Methyl | Methyl | cyclopropylmethyl | 436.11 |
| 3-chlorophenyl | 3-cyanophenyl | H | methyl | 473.11 |
| 3-chlorophenyl | N, R2, R7 = morpholine | N, R2, R7 = morpholine | methyl | 442.11 |
| 3-methoxyphenyl | 2,5-dimethoxyphenyl | H | methyl | 504.12 |
| 3-methoxyphenyl | N, R2, R7 = morpholine | N, R2, R7 = morpholine | methyl | 438.11 |

-continued

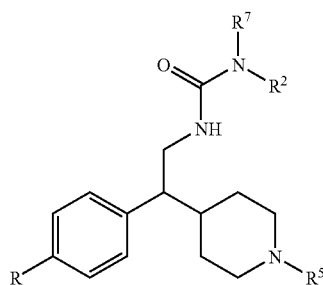

| R | R² | R⁷ | R⁵ | obs M+1 m/z |
|---|---|---|---|---|
| 3-methoxyphenyl | 2-methoxyphenyl | H | cyclopropylmethyl | 514.12 |
| 3-methoxyphenyl | 4-cyanophenyl | H | cyclopentyl | 523.12 |
| 3-methoxyphenyl | N, R2, R7 = pyrrolidine | N, R2, R7 = pyrrolidine | cyclopentyl | 476.11 |
| 3-chlorophenyl | N, R2, R7 = pyrrolidine | N, R2, R7 = pyrrolidine | methyl | 426.1 |
| 3-methoxyphenyl | 4-methoxyphenyl | H | cyclopropylmethyl | 514.12 |
| 3-methoxyphenyl | ethyl | ethyl | cyclopropylmethyl | 464.11 |
| 3-methoxyphenyl | 3,5-dimethoxyphenyl | H | cyclopentyl | 558.13 |
| 3-methoxyphenyl | 2-5-difluorophenyl | H | cyclopentyl | 534.13 |
| 3-methoxyphenyl | Methyl | Methyl | cyclopentyl | 450.11 |
| 3-chlorophenyl | 2,4-difluorophenyl | H | methyl | 484.12 |
| 3-methoxyphenyl | 4-fluorophenyl | H | methyl | 462.11 |
| 3-methoxyphenyl | Phenyl | Methyl | methyl | 458.11 |
| 3-methoxyphenyl | Phenyl | Methyl | cyclopropylmethyl | 498.12 |
| 3-methoxyphenyl | 2,5-dimethoxyphenyl | H | cyclopentyl | 558.13 |
| 3-methoxyphenyl | 4-fluorophenyl | H | cyclopentyl | 516.1 |
| 3-methoxyphenyl | 2,4-difluorophenyl | H | cyclopentyl | 534.13 |
| 3-chlorophenyl | 3-methoxyphenyl | H | cyclopropylmethyl | 518.12 |
| 3-methoxyphenyl | 2-methoxyphenyl | H | cyclopentyl | 528.13 |
| 3-methoxyphenyl | 3,5-dichlorophenyl | H | 3,4-ethylenedioxybenzyl | 646.15 |
| 3-methoxyphenyl | 2,4-dimethoxyphenyl | H | 3,4-ethylenedioxybenzyl | 638.15 |
| 3-methoxyphenyl | 3-fluorophenyl | H | cyclopropylmethyl | 502.12 |
| 3-methoxyphenyl | 2-fluorophenyl | H | cyclopentyl | 516.12 |
| 3-methoxyphenyl | 3-chlorophenyl | H | methyl | 478.11 |
| 3-methoxyphenyl | 2,4-dimethoxyphenyl | H | methyl | 504.12 |
| 3-methoxyphenyl | 3-fluorophenyl | H | methyl | 462.11 |
| 3-methoxyphenyl | 3-methoxyphenyl | H | cyclopropylmethyl | 514.12 |
| 3-methoxyphenyl | 3-fluorophenyl | H | cyclopentyl | 516.12 |
| 3-methoxyphenyl | isopropyl | isopropyl | cyclopentyl | 506.12 |
| 3-methoxyphenyl | N, R2, R7 = morpholine | N, R2, R7 = morpholine | 3,4-ethylenedioxybenzyl | 572.13 |
| 3-methoxyphenyl | 3-chlorophenyl | H | cyclopropylmethyl | 518.12 |
| 3-methoxyphenyl | 3,4-difluorophenyl | H | cyclopropylmethyl | 520.12 |
| 3-methoxyphenyl | Methyl | Methyl | methyl | 396.1 |
| 3-methoxyphenyl | N, R2, R7 = pyrrolidine | N, R2, R7 = pyrrolidine | cyclopropylmethyl | 462.11 |
| 3-chlorophenyl | 2-5-difluorophenyl | H | methyl | 484.12 |
| 3-methoxyphenyl | 2,4-dimethoxyphenyl | H | cyclopropylmethyl | 544.13 |
| 3-methoxyphenyl | 3-chlorophenyl | H | 3,4-ethylenedioxybenzyl | 612.14 |
| 3-methoxyphenyl | ethyl | ethyl | methyl | 424.1 |
| 3-methoxyphenyl | 3,5-dimethoxyphenyl | H | cyclopropylmethyl | 544.13 |
| 3-chlorophenyl | 4-methoxyphenyl | H | methyl | 478.11 |
| 3-methoxyphenyl | 3-methoxyphenyl | H | methyl | 474.11 |
| 3-methoxyphenyl | 3,4-methylenedioxyphenyl | H | 3,4-ethylenedioxybenzyl | 622.15 |
| 3-methoxyphenyl | isopropyl | isopropyl | 3,4-ethylenedioxybenzyl | 586.14 |
| 3-chlorophenyl | isopropyl | isopropyl | methyl | 456.11 |
| 3-methoxyphenyl | Phenyl | H | cyclopropylmethyl | 484.12 |
| 3-methoxyphenyl | 4-cyanophenyl | H | methyl | 469.11 |
| 3-methoxyphenyl | isopropyl | isopropyl | methyl | 452.11 |
| 3-methoxyphenyl | 3-methoxyphenyl | H | cyclopentyl | 528.13 |
| 3-methoxyphenyl | 4-methoxyphenyl | H | methyl | 474.11 |
| 3-methoxyphenyl | 3,5-dimethoxyphenyl | H | methyl | 504.12 |
| 3-methoxyphenyl | 2,5-dimethoxyphenyl | H | cyclopropylmethyl | 544.13 |
| 3-methoxyphenyl | isopropyl | isopropyl | cyclopropylmethyl | 492.12 |
| 3-chlorophenyl | 3,4-methylenedioxyphenyl | H | cyclopropylmethyl | 532.13 |
| 3-chlorophenyl | 2,5-dimethoxyphenyl | H | cyclopropylmethyl | 548.13 |
| 3-chlorophenyl | 2,4-dimethoxyphenyl | H | cyclopropylmethyl | 548.13 |

-continued

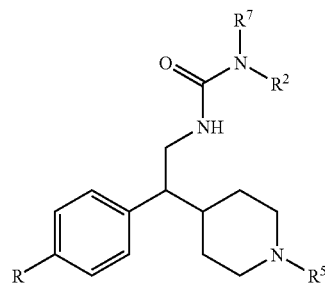

| R | R² | R⁷ | R⁵ | obs M+1 m/z |
|---|---|---|---|---|
| 3-chlorophenyl | 3,5-dimethoxyphenyl | H | cyclopropylmethyl | 548.13 |
| 3-chlorophenyl | 2-fluorophenyl | H | cyclopropylmethyl | 506.12 |
| 3-chlorophenyl | 3-fluorophenyl | H | cyclopropylmethyl | 506.12 |
| 3-chlorophenyl | 4-fluorophenyl | H | cyclopropylmethyl | 506.12 |
| 3-chlorophenyl | 3,4-difluorophenyl | H | cyclopropylmethyl | 524.12 |
| 3-chlorophenyl | 2,4-difluorophenyl | H | cyclopropylmethyl | 524.12 |
| 3-chlorophenyl | 2,6-difluorophenyl | H | cyclopropylmethyl | 524.12 |
| 3-chlorophenyl | 2-5-difluorophenyl | H | cyclopropylmethyl | 524.12 |
| 3-chlorophenyl | 3-cyanophenyl | H | cyclopropylmethyl | 513.12 |
| 3-chlorophenyl | 4-cyanophenyl | H | cyclopropylmethyl | 513.12 |
| 3-chlorophenyl | N, R2, R7 = pyrrolidine | N, R2, R7 = pyrrolidine | cyclopropylmethyl | 466.11 |
| 3-chlorophenyl | N, R2, R7 = morpholine | N, R2, R7 = morpholine | cyclopropylmethyl | 482.12 |
| 3-chlorophenyl | Phenyl | Methyl | cyclopropylmethyl | 502.12 |
| 3-chlorophenyl | isopropyl | isopropyl | cyclopropylmethyl | 496.12 |
| 3-chlorophenyl | Methyl | Methyl | cyclopropylmethyl | 440.11 |
| 3-chlorophenyl | ethyl | ethyl | cyclopropylmethyl | 468.11 |
| 3-chlorophenyl | Phenyl | H | cyclopentyl | 502.12 |
| 3-chlorophenyl | 2-chlorophenyl | H | cyclopentyl | 536.13 |
| 3-chlorophenyl | 3-chlorophenyl | H | cyclopentyl | 536.13 |
| 3-chlorophenyl | 4-chlorophenyl | H | cyclopentyl | 536.13 |
| 3-chlorophenyl | 2-methoxyphenyl | H | cyclopentyl | 532.13 |
| 3-chlorophenyl | 3-methoxyphenyl | H | cyclopentyl | 532.13 |
| 3-chlorophenyl | 4-methoxyphenyl | H | cyclopentyl | 532.13 |
| 3-chlorophenyl | 3,4-methylenedioxyphenyl | H | cyclopentyl | 546.13 |
| 3-chlorophenyl | 2,5-dimethoxyphenyl | H | cyclopentyl | 562.13 |
| 3-chlorophenyl | 2,4-dimethoxyphenyl | H | cyclopentyl | 562.13 |
| 3-chlorophenyl | 3,5-dimethoxyphenyl | H | cyclopentyl | 562.13 |
| 3-chlorophenyl | 2-fluorophenyl | H | cyclopentyl | 520.12 |
| 3-chlorophenyl | 3-fluorophenyl | H | cyclopentyl | 520.12 |
| 3-chlorophenyl | 4-fluorophenyl | H | cyclopentyl | 520.12 |
| 3-chlorophenyl | 3,4-difluorophenyl | H | cyclopentyl | 538.13 |
| 3-chlorophenyl | 2,4-difluorophenyl | H | cyclopentyl | 538.13 |
| 3-chlorophenyl | 2,6-difluorophenyl | H | cyclopentyl | 538.13 |
| 3-chlorophenyl | 2-5-difluorophenyl | H | cyclopentyl | 538.13 |
| 3-chlorophenyl | 3-cyanophenyl | H | cyclopentyl | 527.12 |
| 3-chlorophenyl | 4-cyanophenyl | H | cyclopentyl | 527.12 |
| 3-chlorophenyl | N, R2, R7 = pyrrolidine | N, R2, R7 = pyrrolidine | cyclopentyl | 480.12 |
| 3-chlorophenyl | N, R2, R7 = morpholine | N, R2, R7 = morpholine | cyclopentyl | 496.12 |
| 3-chlorophenyl | Phenyl | Methyl | cyclopentyl | 516.12 |
| 3-chlorophenyl | isopropyl | isopropyl | cyclopentyl | 510.12 |
| 3-chlorophenyl | Methyl | Methyl | cyclopentyl | 454.11 |
| 3-chlorophenyl | ethyl | ethyl | cyclopentyl | 482.12 |
| 3-chlorophenyl | Phenyl | H | 3,4-ethylenedioxybenzyl | 582.14 |
| 3-chlorophenyl | 2-chlorophenyl | H | 3,4-ethylenedioxybenzyl | 616.14 |
| 3-chlorophenyl | 3-chlorophenyl | H | 3,4-ethylenedioxybenzyl | 616.14 |
| 3-chlorophenyl | 4-chlorophenyl | H | 3,4-ethylenedioxybenzyl | 616.14 |
| 3-chlorophenyl | 2-methoxyphenyl | H | 3,4-ethylenedioxybenzyl | 612.14 |
| 3-chlorophenyl | 3-methoxyphenyl | H | 3,4-ethylenedioxybenzyl | 612.14 |
| 3-chlorophenyl | 4-methoxyphenyl | H | 3,4-ethylenedioxybenzyl | 612.14 |
| 3-chlorophenyl | 3,4-methylenedioxyphenyl | H | 3,4-ethylenedioxybenzyl | 626.15 |
| 3-chlorophenyl | 2,5-dimethoxyphenyl | H | 3,4-ethylenedioxybenzyl | 642.15 |
| 3-chlorophenyl | 2,4-dimethoxyphenyl | H | 3,4-ethylenedioxybenzyl | 642.15 |
| 3-chlorophenyl | 3,5-dimethoxyphenyl | H | 3,4-ethylenedioxybenzyl | 642.15 |
| 3-chlorophenyl | 2-fluorophenyl | H | 3,4-ethylenedioxybenzyl | 600.14 |

-continued

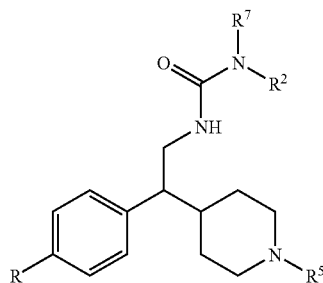

| R | R² | R⁷ | R⁵ | obs M+1 m/z |
|---|---|---|---|---|
| 3-chlorophenyl | 3-fluorophenyl | H | 3,4-ethylenedioxybenzyl | 600.14 |
| 3-chlorophenyl | 4-fluorophenyl | H | 3,4-ethylenedioxybenzyl | 600.14 |
| 3-chlorophenyl | 3-chloro,4-fluorophenyl | H | 3,4-ethylenedioxybenzyl | 634.15 |
| 3-chlorophenyl | 3,4-difluorophenyl | H | 3,4-ethylenedioxybenzyl | 618.14 |
| 3-chlorophenyl | 2,4-difluorophenyl | H | 3,4-ethylenedioxybenzyl | 618.14 |
| 3-chlorophenyl | 2,6-difluorophenyl | H | 3,4-ethylenedioxybenzyl | 618.14 |
| 3-chlorophenyl | 2-5-difluorophenyl | H | 3,4-ethylenedioxybenzyl | 618.14 |
| 3-chlorophenyl | 3-cyanophenyl | H | 3,4-ethylenedioxybenzyl | 607.14 |
| 3-chlorophenyl | N, R2, R7 = pyrrolidine | N, R2, R7 = pyrrolidine | 3,4-ethylenedioxybenzyl | 560.13 |
| 3-chlorophenyl | N, R2, R7 = morpholine | N, R2, R7 = morpholine | 3,4-ethylenedioxybenzyl | 576.14 |
| 3-chlorophenyl | Phenyl | Methyl | 3,4-ethylenedioxybenzyl | 596.14 |
| 3-chlorophenyl | isopropyl | isopropyl | 3,4-ethylenedioxybenzyl | 590.14 |
| 3-chlorophenyl | Methyl | Methyl | 3,4-ethylenedioxybenzyl | 534.13 |
| 3-chlorophenyl | ethyl | ethyl | 3,4-ethylenedioxybenzyl | 562.13 |
| 3-cyanophenyl | 3-fluorophenyl | H | 4-pyranyl | 527.1 |
| 3-cyanophenyl | 3-cyanophenyl | H | 4-pyranyl | 534.1 |
| 4-fluorophenyl | Phenyl | H | methyl | 432.1 |
| 4-fluorophenyl | 2-chlorophenyl | H | methyl | 466.11 |
| 4-fluorophenyl | 3-chlorophenyl | H | methyl | 466.11 |
| 4-fluorophenyl | 4-chlorophenyl | H | methyl | 466.11 |
| 4-fluorophenyl | 2-methoxyphenyl | H | methyl | 462.11 |
| 4-fluorophenyl | 3-methoxyphenyl | H | methyl | 462.11 |
| 4-fluorophenyl | 4-methoxyphenyl | H | methyl | 462.11 |
| 4-fluorophenyl | 3,4-methylenedioxyphenyl | H | methyl | 476.11 |
| 4-fluorophenyl | 2,5-dimethoxyphenyl | H | methyl | 492.12 |
| 4-fluorophenyl | 2,4-dimethoxyphenyl | H | methyl | 492.12 |
| 4-fluorophenyl | 3,5-dimethoxyphenyl | H | methyl | 492.12 |
| 4-fluorophenyl | 2-fluorophenyl | H | methyl | 450.11 |
| 4-fluorophenyl | 3-fluorophenyl | H | methyl | 450.11 |
| 4-fluorophenyl | 4-fluorophenyl | H | methyl | 450.11 |
| 4-fluorophenyl | 3-chloro,4-fluorophenyl | H | methyl | 484.12 |
| 4-fluorophenyl | 3,4-difluorophenyl | H | methyl | 468.11 |
| 4-fluorophenyl | 2,4-difluorophenyl | H | methyl | 468.11 |
| 4-fluorophenyl | 2,6-difluorophenyl | H | methyl | 468.11 |
| 4-fluorophenyl | 2-5-difluorophenyl | H | methyl | 468.11 |
| 4-fluorophenyl | 3-cyanophenyl | H | methyl | 457.11 |
| 4-fluorophenyl | 4-cyanophenyl | H | methyl | 457.11 |
| 4-fluorophenyl | N, R2, R7 = pyrrolidine | N, R2, R7 = pyrrolidine | methyl | 410.1 |
| 4-fluorophenyl | N, R2, R7 = morpholine | N, R2, R7 = morpholine | methyl | 426.1 |
| 4-fluorophenyl | Phenyl | Methyl | methyl | 446.11 |
| 4-fluorophenyl | isopropyl | isopropyl | methyl | 440.11 |
| 4-fluorophenyl | Methyl | Methyl | methyl | 384.09 |
| 4-fluorophenyl | ethyl | ethyl | methyl | 412.1 |
| 4-fluorophenyl | Phenyl | H | cyclopropylmethyl | 472.11 |
| 4-fluorophenyl | 3,5-dichlorophenyl | H | cyclopropylmethyl | 540.13 |
| 4-fluorophenyl | 2-chlorophenyl | H | cyclopropylmethyl | 506.12 |
| 4-fluorophenyl | 3-chlorophenyl | H | cyclopropylmethyl | 506.12 |
| 4-fluorophenyl | 4-chlorophenyl | H | cyclopropylmethyl | 506.12 |
| 4-fluorophenyl | 2-methoxyphenyl | H | cyclopropylmethyl | 502.12 |
| 4-fluorophenyl | 3-methoxyphenyl | H | cyclopropylmethyl | 502.12 |
| 4-fluorophenyl | 4-methoxyphenyl | H | cyclopropylmethyl | 502.12 |
| 4-fluorophenyl | 3,4-methylenedioxyphenyl | H | cyclopropylmethyl | 516.12 |

-continued

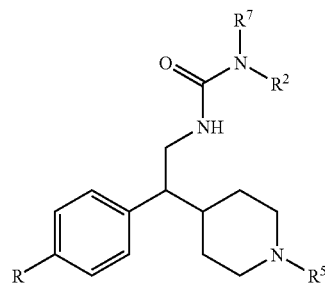

| R | R² | R⁷ | R⁵ | obs M+1 m/z |
|---|---|---|---|---|
| 4-fluorophenyl | 2,5-dimethoxyphenyl | H | cyclopropylmethyl | 532.13 |
| 4-fluorophenyl | 2,4-dimethoxyphenyl | H | cyclopropylmethyl | 532.13 |
| 4-fluorophenyl | 3,5-dimethoxyphenyl | H | cyclopropylmethyl | 532.13 |
| 4-fluorophenyl | 2-fluorophenyl | H | cyclopropylmethyl | 490.12 |
| 4-fluorophenyl | 3-fluorophenyl | H | cyclopropylmethyl | 490.12 |
| 4-fluorophenyl | 4-fluorophenyl | H | cyclopropylmethyl | 490.12 |
| 4-fluorophenyl | 3-chloro,4-fluorophenyl | H | cyclopropylmethyl | 524.12 |
| 4-fluorophenyl | 3,4-difluorophenyl | H | cyclopropylmethyl | 508.12 |
| 4-fluorophenyl | 2,4-difluorophenyl | H | cyclopropylmethyl | 508.12 |
| 4-fluorophenyl | 2,6-difluorophenyl | H | cyclopropylmethyl | 508.12 |
| 4-fluorophenyl | 2-5-difluorophenyl | H | cyclopropylmethyl | 508.12 |
| 4-fluorophenyl | 3-cyanophenyl | H | cyclopropylmethyl | 497.12 |
| 4-fluorophenyl | 4-cyanophenyl | H | cyclopropylmethyl | 497.12 |
| 4-fluorophenyl | N, R2, R7 = pyrrolidine | N, R2, R7 = pyrrolidine | cyclopropylmethyl | 450.11 |
| 4-fluorophenyl | Phenyl | Methyl | cyclopropylmethyl | 486.12 |
| 4-fluorophenyl | isopropyl | isopropyl | cyclopropylmethyl | 480.12 |
| 4-fluorophenyl | Methyl | Methyl | cyclopropylmethyl | 424.1 |
| 4-fluorophenyl | ethyl | ethyl | cyclopropylmethyl | 452.11 |
| 4-fluorophenyl | Phenyl | H | cyclopentyl | 486.12 |
| 4-fluorophenyl | 3,5-dichlorophenyl | H | cyclopentyl | 554.13 |
| 4-fluorophenyl | 2-chlorophenyl | H | cyclopentyl | 520.12 |
| 4-fluorophenyl | 3-chlorophenyl | H | cyclopentyl | 520.12 |
| 4-fluorophenyl | 4-chlorophenyl | H | cyclopentyl | 520.12 |
| 4-fluorophenyl | 2-methoxyphenyl | H | cyclopentyl | 516.12 |
| 4-fluorophenyl | 3-methoxyphenyl | H | cyclopentyl | 516.12 |
| 4-fluorophenyl | 4-methoxyphenyl | H | cyclopentyl | 516.12 |
| 4-fluorophenyl | 3,4-methylenedioxyphenyl | H | cyclopentyl | 530.13 |
| 4-fluorophenyl | 2,5-dimethoxyphenyl | H | cyclopentyl | 546.1 |
| 4-fluorophenyl | 2,4-dimethoxyphenyl | H | cyclopentyl | 546.13 |
| 4-fluorophenyl | 3,5-dimethoxyphenyl | H | cyclopentyl | 546.13 |
| 4-fluorophenyl | 2-fluorophenyl | H | cyclopentyl | 504.12 |
| 4-fluorophenyl | 3-fluorophenyl | H | cyclopentyl | 504.12 |
| 4-fluorophenyl | 4-fluorophenyl | H | cyclopentyl | 504.12 |
| 4-fluorophenyl | 3-chloro,4-fluorophenyl | H | cyclopentyl | 538.13 |
| 4-fluorophenyl | 3,4-difluorophenyl | H | cyclopentyl | 522.12 |
| 4-fluorophenyl | 2,4-difluorophenyl | H | cyclopentyl | 522.12 |
| 4-fluorophenyl | 2,6-difluorophenyl | H | cyclopentyl | 522.12 |
| 4-fluorophenyl | 2-5-difluorophenyl | H | cyclopentyl | 522.12 |
| 4-fluorophenyl | 3-cyanophenyl | H | cyclopentyl | 511.1 |
| 4-fluorophenyl | 4-cyanophenyl | H | cyclopentyl | 511.12 |
| 4-fluorophenyl | N, R2, R7 = pyrrolidine | N, R2, R7 = pyrrolidine | cyclopentyl | 464.11 |
| 4-fluorophenyl | N, R2, R7 = morpholine | N, R2, R7 = morpholine | cyclopentyl | 480.12 |
| 4-fluorophenyl | Phenyl | Methyl | cyclopentyl | 500.12 |
| 4-fluorophenyl | isopropyl | isopropyl | cyclopentyl | 494.12 |
| 4-fluorophenyl | Methyl | Methyl | cyclopentyl | 438.11 |
| 4-fluorophenyl | ethyl | ethyl | cyclopentyl | 466.11 |
| 4-fluorophenyl | Phenyl | H | 3,4-ethylenedioxybenzyl | 566.13 |
| 4-fluorophenyl | 3,5-dichlorophenyl | H | 3,4-ethylenedioxybenzyl | 634.15 |
| 4-fluorophenyl | 2-chlorophenyl | H | 3,4-ethylenedioxybenzyl | 600.14 |
| 4-fluorophenyl | 3-chlorophenyl | H | 3,4-ethylenedioxybenzyl | 600.14 |
| 4-fluorophenyl | 4-chlorophenyl | H | 3,4-ethylenedioxybenzyl | 600.14 |
| 4-fluorophenyl | 2-methoxyphenyl | H | 3,4-ethylenedioxybenzyl | 596.14 |
| 4-fluorophenyl | 3-methoxyphenyl | H | 3,4-ethylenedioxybenzyl | 596.14 |
| 4-fluorophenyl | 4-methoxyphenyl | H | 3,4-ethylenedioxybenzyl | 596.14 |

-continued

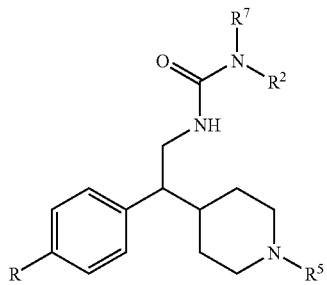

| R | R² | R⁷ | R⁵ | obs M + 1 m/z |
|---|---|---|---|---|
| 4-fluorophenyl | 3,4-methylenedioxyphenyl | H | 3,4-ethylenedioxybenzyl | 610.14 |
| 4-fluorophenyl | 2,5-dimethoxyphenyl | H | 3,4-ethylenedioxybenzyl | 626.15 |
| 4-fluorophenyl | 2,4-dimethoxyphenyl | H | 3,4-ethylenedioxybenzyl | 626.15 |
| 4-fluorophenyl | 3,5-dimethoxyphenyl | H | 3,4-ethylenedioxybenzyl | 626.15 |
| 4-fluorophenyl | 2-fluorophenyl | H | 3,4-ethylenedioxybenzyl | 584.14 |
| 4-fluorophenyl | 3-fluorophenyl | H | 3,4-ethylenedioxybenzyl | 584.14 |
| 4-fluorophenyl | 4-fluorophenyl | H | 3,4-ethylenedioxybenzyl | 584.14 |
| 4-fluorophenyl | 3-chloro,4-fluorophenyl | H | 3,4-ethylenedioxybenzyl | 618.14 |
| 4-fluorophenyl | 3,4-difluorophenyl | H | 3,4-ethylenedioxybenzyl | 602.14 |
| 4-fluorophenyl | 2,4-difluorophenyl | H | 3,4-ethylenedioxybenzyl | 602.14 |
| 4-fluorophenyl | 2,6-difluorophenyl | H | 3,4-ethylenedioxybenzyl | 602.14 |
| 4-fluorophenyl | 2-5-difluorophenyl | H | 3,4-ethylenedioxybenzyl | 602.14 |
| 4-fluorophenyl | 3-cyanophenyl | H | 3,4-ethylenedioxybenzyl | 591.14 |
| 4-fluorophenyl | 4-cyanophenyl | H | 3,4-ethylenedioxybenzyl | 591.1 |
| 4-fluorophenyl | N, R2, R7 = pyrrolidine | N, R2, R7 = pyrrolidine | 3,4-ethylenedioxybenzyl | 544.13 |
| 4-fluorophenyl | N, R2, R7 = morpholine | N, R2, R7 = morpholine | 3,4-ethylenedioxybenzyl | 560.13 |
| 4-fluorophenyl | Phenyl | Methyl | 3,4-ethylenedioxybenzyl | 580.14 |
| 4-fluorophenyl | isopropyl | isopropyl | 3,4-ethylenedioxybenzyl | 574.13 |
| 4-fluorophenyl | Methyl | Methyl | 3,4-ethylenedioxybenzyl | 518.12 |
| 4-methoxyphenyl | Phenyl | H | methyl | 444.11 |
| 4-methoxyphenyl | 3,5-dichlorophenyl | H | methyl | 512.12 |
| 4-methoxyphenyl | 2-chlorophenyl | H | methyl | 478.11 |
| 4-methoxyphenyl | 3-chlorophenyl | H | methyl | 478.11 |
| 4-methoxyphenyl | 4-chlorophenyl | H | methyl | 478.11 |
| 4-methoxyphenyl | 2-methoxyphenyl | H | methyl | 474.11 |
| 4-methoxyphenyl | 3-methoxyphenyl | H | methyl | 474.11 |
| 4-methoxyphenyl | 4-methoxyphenyl | H | methyl | 474.11 |
| 4-methoxyphenyl | 3,4-methylenedioxyphenyl | H | methyl | 488.12 |
| 4-methoxyphenyl | 2,5-dimethoxyphenyl | H | methyl | 504.12 |
| 4-methoxyphenyl | 2,4-dimethoxyphenyl | H | methyl | 504.12 |
| 4-methoxyphenyl | 3,5-dimethoxyphenyl | H | methyl | 504.12 |
| 4-methoxyphenyl | 2-fluorophenyl | H | methyl | 462.11 |
| 4-methoxyphenyl | 3-fluorophenyl | H | methyl | 462.11 |
| 4-methoxyphenyl | 4-fluorophenyl | H | methyl | 462.11 |
| 4-methoxyphenyl | 3-chloro,4-fluorophenyl | H | methyl | 496.12 |
| 4-methoxyphenyl | 3,4-difluorophenyl | H | methyl | 480.12 |
| 4-methoxyphenyl | 2,4-difluorophenyl | H | methyl | 480.12 |
| 4-methoxyphenyl | 2,6-difluorophenyl | H | methyl | 480.12 |
| 4-methoxyphenyl | 2-5-difluorophenyl | H | methyl | 480.12 |
| 4-methoxyphenyl | 3-cyanophenyl | H | methyl | 469.11 |
| 4-methoxyphenyl | 4-cyanophenyl | H | methyl | 469.11 |
| 4-methoxyphenyl | N, R2, R7 = pyrrolidine | N, R2, R7 = pyrrolidine | methyl | 422.1 |
| 4-methoxyphenyl | N, R2, R7 = morpholine | N, R2, R7 = morpholine | methyl | 438.11 |
| 4-methoxyphenyl | Phenyl | Methyl | methyl | 458.11 |
| 4-methoxyphenyl | isopropyl | isopropyl | methyl | 452.11 |
| 4-methoxyphenyl | Methyl | Methyl | methyl | 396.1 |
| 4-methoxyphenyl | ethyl | ethyl | methyl | 424.1 |
| 4-methoxyphenyl | Phenyl | H | cyclopropylmethyl | 484.12 |
| 4-methoxyphenyl | 3,5-dichlorophenyl | H | cyclopropylmethyl | 552.13 |
| 4-methoxyphenyl | 2-chlorophenyl | H | cyclopropylmethyl | 518.12 |
| 4-methoxyphenyl | 3-chlorophenyl | H | cyclopropylmethyl | 518.12 |
| 4-methoxyphenyl | 4-chlorophenyl | H | cyclopropylmethyl | 518.12 |

-continued

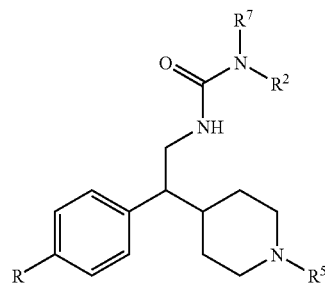

| R | R² | R⁷ | R⁵ | obs M + 1 m/z |
|---|---|---|---|---|
| 4-methoxyphenyl | 2-methoxyphenyl | H | cyclopropylmethyl | 514.12 |
| 4-methoxyphenyl | 3-methoxyphenyl | H | cyclopropylmethyl | 514.12 |
| 4-methoxyphenyl | 4-methoxyphenyl | H | cyclopropylmethyl | 514.12 |
| 4-methoxyphenyl | 3,4-methylenedioxyphenyl | H | cyclopropylmethyl | 528.13 |
| 4-methoxyphenyl | 2,5-dimethoxyphenyl | H | cyclopropylmethyl | 544.13 |
| 4-methoxyphenyl | 2,4-dimethoxyphenyl | H | cyclopropylmethyl | 544.13 |
| 4-methoxyphenyl | 3,5-dimethoxyphenyl | H | cyclopropylmethyl | 544.13 |
| 4-methoxyphenyl | 2-fluorophenyl | H | cyclopropylmethyl | 502.12 |
| 4-methoxyphenyl | 3-fluorophenyl | H | cyclopropylmethyl | 502.12 |
| 4-methoxyphenyl | 4-fluorophenyl | H | cyclopropylmethyl | 502.12 |
| 4-methoxyphenyl | 3-chloro,4-fluorophenyl | H | cyclopropylmethyl | 536.13 |
| 4-methoxyphenyl | 3,4-difluorophenyl | H | cyclopropylmethyl | 520.12 |
| 4-methoxyphenyl | 2,4-difluorophenyl | H | cyclopropylmethyl | 521.12 |
| 4-methoxyphenyl | 2,6-difluorophenyl | H | cyclopropylmethyl | 520.12 |
| 4-methoxyphenyl | 2-5-difluorophenyl | H | cyclopropylmethyl | 520.12 |
| 4-methoxyphenyl | 3-cyanophenyl | H | cyclopropylmethyl | 509.12 |
| 4-methoxyphenyl | 4-cyanophenyl | H | cyclopropylmethyl | 509.12 |
| 4-methoxyphenyl | N, R2, R7 = pyrrolidine | N, R2, R7 = pyrrolidine | cyclopropylmethyl | 462.11 |
| 4-methoxyphenyl | N, R2, R7 = morpholine | N, R2, R7 = morpholine | cyclopropylmethyl | 478.11 |
| 4-methoxyphenyl | Phenyl | Methyl | cyclopropylmethyl | 498.12 |
| 4-methoxyphenyl | isopropyl | isopropyl | cyclopropylmethyl | 492.12 |
| 4-methoxyphenyl | Methyl | Methyl | cyclopropylmethyl | 436.11 |
| 4-methoxyphenyl | ethyl | ethyl | cyclopropylmethyl | 464.11 |
| 4-methoxyphenyl | 3,5-dichlorophenyl | H | cyclopentyl | 566.13 |
| 4-methoxyphenyl | 2-chlorophenyl | H | cyclopentyl | 532.13 |
| 4-methoxyphenyl | 3-chlorophenyl | H | cyclopentyl | 532.1 |
| 4-methoxyphenyl | 4-chlorophenyl | H | cyclopentyl | 532.13 |
| 4-methoxyphenyl | 2-methoxyphenyl | H | cyclopentyl | 528.1 |
| 4-methoxyphenyl | 3-methoxyphenyl | H | cyclopentyl | 528.1 |
| 4-methoxyphenyl | 4-methoxyphenyl | H | cyclopentyl | 528.13 |
| 4-methoxyphenyl | 3,4-methylenedioxyphenyl | H | cyclopentyl | 542.13 |
| 4-methoxyphenyl | 2,5-dimethoxyphenyl | H | cyclopentyl | 558.13 |
| 4-methoxyphenyl | 2,4-dimethoxyphenyl | H | cyclopentyl | 558.13 |
| 4-methoxyphenyl | 3,5-dimethoxyphenyl | H | cyclopentyl | 558.1 |
| 4-methoxyphenyl | 2-fluorophenyl | H | cyclopentyl | 516.1 |
| 4-methoxyphenyl | 3-fluorophenyl | H | cyclopentyl | 516.12 |
| 4-methoxyphenyl | 4-fluorophenyl | H | cyclopentyl | 516.12 |
| 4-methoxyphenyl | 3-chloro,4-fluorophenyl | H | cyclopentyl | 550.13 |
| 4-methoxyphenyl | 3,4-difluorophenyl | H | cyclopentyl | 534.13 |
| 4-methoxyphenyl | 2,4-difluorophenyl | H | cyclopentyl | 535.13 |
| 4-methoxyphenyl | 2,6-difluorophenyl | H | cyclopentyl | 534.1 |
| 4-methoxyphenyl | 2-5-difluorophenyl | H | cyclopentyl | 534.1 |
| 4-methoxyphenyl | 3-cyanophenyl | H | cyclopentyl | 523.12 |
| 4-methoxyphenyl | 4-cyanophenyl | H | cyclopentyl | 523.12 |
| 4-methoxyphenyl | N, R2, R7 = pyrrolidine | N, R2, R7 = pyrrolidine | cyclopentyl | 476.11 |
| 4-methoxyphenyl | N, R2, R7 = morpholine | N, R2, R7 = morpholine | cyclopentyl | 492.12 |
| 4-fluorophenyl | N, R2, R7 = morpholine | N, R2, R7 = morpholine | cyclopropylmethyl | 466.11 |
| 4-methoxyphenyl | Phenyl | Methyl | cyclopentyl | 512.12 |
| 4-methoxyphenyl | isopropyl | isopropyl | cyclopentyl | 506.12 |
| 4-methoxyphenyl | Methyl | Methyl | cyclopentyl | 450.11 |
| 4-methoxyphenyl | ethyl | ethyl | cyclopentyl | 478.11 |
| 4-methoxyphenyl | Phenyl | H | 3,4-ethylenedioxybenzyl | 578.14 |

-continued

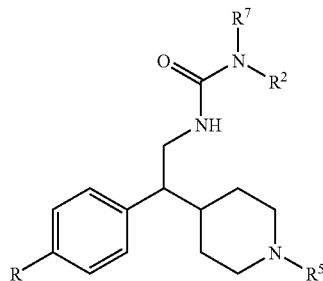

| R | $R^2$ | $R^7$ | $R^5$ | obs M + 1 m/z |
|---|---|---|---|---|
| 4-methoxyphenyl | 3,5-dichlorophenyl | H | 3,4-ethylenedioxybenzyl | 646.15 |
| 4-methoxyphenyl | 2-chlorophenyl | H | 3,4-ethylenedioxybenzyl | 612.14 |
| 4-methoxyphenyl | 3-chlorophenyl | H | 3,4-ethylenedioxybenzyl | 612.14 |
| 4-methoxyphenyl | 4-chlorophenyl | H | 3,4-ethylenedioxybenzyl | 612.14 |
| 4-methoxyphenyl | 2-methoxyphenyl | H | 3,4-ethylenedioxybenzyl | 608.14 |
| 4-methoxyphenyl | 3-methoxyphenyl | H | 3,4-ethylenedioxybenzyl | 608.14 |
| 4-methoxyphenyl | 4-methoxyphenyl | H | 3,4-ethylenedioxybenzyl | 608.14 |
| 4-methoxyphenyl | 3,4-methylenedioxyphenyl | H | 3,4-ethylenedioxybenzyl | 622.15 |
| 4-methoxyphenyl | 2,5-dimethoxyphenyl | H | 3,4-ethylenedioxybenzyl | 638.15 |
| 4-methoxyphenyl | 2,4-dimethoxyphenyl | H | 3,4-ethylenedioxybenzyl | 638.15 |
| 4-methoxyphenyl | 3,5-dimethoxyphenyl | H | 3,4-ethylenedioxybenzyl | 638.15 |
| 4-methoxyphenyl | 2-fluorophenyl | H | 3,4-ethylenedioxybenzyl | 596.14 |
| 4-methoxyphenyl | 3-fluorophenyl | H | 3,4-ethylenedioxybenzyl | 596.14 |
| 4-methoxyphenyl | 4-fluorophenyl | H | 3,4-ethylenedioxybenzyl | 596.14 |
| 4-methoxyphenyl | 3-chloro,4-fluorophenyl | H | 3,4-ethylenedioxybenzyl | 630.15 |
| 4-methoxyphenyl | 3,4-difluorophenyl | H | 3,4-ethylenedioxybenzyl | 614.14 |
| 4-methoxyphenyl | 2,4-difluorophenyl | H | 3,4-ethylenedioxybenzyl | 614.14 |
| 4-methoxyphenyl | 2,6-difluorophenyl | H | 3,4-ethylenedioxybenzyl | 614.14 |
| 4-methoxyphenyl | 2-5-difluorophenyl | H | 3,4-ethylenedioxybenzyl | 614.14 |
| 4-methoxyphenyl | 3-cyanophenyl | H | 3,4-ethylenedioxybenzyl | 603.14 |
| 4-methoxyphenyl | 4-cyanophenyl | H | 3,4-ethylenedioxybenzyl | 603.14 |
| 4-methoxyphenyl | N, R2, R7 = pyrrolidine | N, R2, R7 = pyrrolidine | 3,4-ethylenedioxybenzyl | 556.13 |
| 4-methoxyphenyl | N, R2, R7 = morpholine | N, R2, R7 = morpholine | 3,4-ethylenedioxybenzyl | 572.13 |
| 4-methoxyphenyl | Phenyl | Methyl | 3,4-ethylenedioxybenzyl | 592.14 |
| 4-methoxyphenyl | isopropyl | isopropyl | 3,4-ethylenedioxybenzyl | 586.14 |
| 4-methoxyphenyl | Methyl | Methyl | 3,4-ethylenedioxybenzyl | 530.13 |
| 4-methoxyphenyl | ethyl | ethyl | 3,4-ethylenedioxybenzyl | 558.13 |
| 4-chlorophenyl | Phenyl | H | methyl | 448.11 |
| 4-chlorophenyl | 2-chlorophenyl | H | methyl | 482.12 |
| 4-chlorophenyl | 3-chlorophenyl | H | methyl | 482.12 |
| 4-chlorophenyl | 4-chlorophenyl | H | methyl | 482.12 |
| 4-chlorophenyl | 2-methoxyphenyl | H | methyl | 478.11 |
| 4-chlorophenyl | 3-methoxyphenyl | H | methyl | 478.11 |
| 4-chlorophenyl | 4-methoxyphenyl | H | methyl | 478.11 |
| 4-chlorophenyl | 3,4-methylenedioxyphenyl | H | methyl | 492.12 |
| 4-chlorophenyl | 2,5-dimethoxyphenyl | H | methyl | 508.12 |
| 4-chlorophenyl | 2,4-dimethoxyphenyl | H | methyl | 508.12 |
| 4-chlorophenyl | 3,5-dimethoxyphenyl | H | methyl | 508.12 |
| 4-chlorophenyl | 2-fluorophenyl | H | methyl | 466.11 |
| 4-chlorophenyl | 3-fluorophenyl | H | methyl | 466.11 |
| 4-chlorophenyl | 4-fluorophenyl | H | methyl | 466.11 |
| 4-chlorophenyl | 3-chloro,4-fluorophenyl | H | methyl | 500.12 |
| 4-chlorophenyl | 3,4-difluorophenyl | H | methyl | 484.12 |
| 4-chlorophenyl | 2,4-difluorophenyl | H | methyl | 484.12 |
| 4-chlorophenyl | 2,6-difluorophenyl | H | methyl | 484.12 |
| 4-chlorophenyl | 2-5-difluorophenyl | H | methyl | 484.12 |
| 4-chlorophenyl | 3-cyanophenyl | H | methyl | 473.11 |
| 4-chlorophenyl | 4-cyanophenyl | H | methyl | 473.11 |
| 4-chlorophenyl | N, R2, R7 = pyrrolidine | N, R2, R7 = pyrrolidine | methyl | 426.1 |
| 4-chlorophenyl | N, R2, R7 = morpholine | N, R2, R7 = morpholine | methyl | 442.11 |
| 4-chlorophenyl | Phenyl | Methyl | methyl | 462.11 |
| 4-chlorophenyl | Methyl | Methyl | methyl | 400.1 |
| 4-chlorophenyl | ethyl | ethyl | methyl | 428.1 |
| 4-chlorophenyl | Phenyl | H | cyclopropylmethyl | 488.12 |

-continued

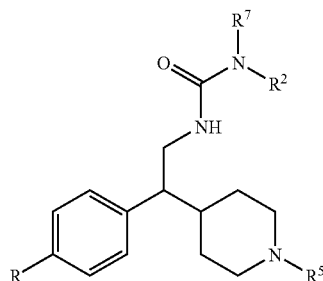

| R | R² | R⁷ | R⁵ | obs M + 1 m/z |
|---|---|---|---|---|
| 4-chlorophenyl | 3,5-dichlorophenyl | H | cyclopropylmethyl | 558.13 |
| 4-chlorophenyl | 2-chlorophenyl | H | cyclopropylmethyl | 522.12 |
| 4-chlorophenyl | 3-chlorophenyl | H | cyclopropylmethyl | 522.12 |
| 4-chlorophenyl | 4-chlorophenyl | H | cyclopropylmethyl | 522.12 |
| 4-chlorophenyl | 2-methoxyphenyl | H | cyclopropylmethyl | 518.12 |
| 4-chlorophenyl | 3-methoxyphenyl | H | cyclopropylmethyl | 518.12 |
| 4-chlorophenyl | 4-methoxyphenyl | H | cyclopropylmethyl | 518.12 |
| 4-chlorophenyl | 3,4-methylenedioxyphenyl | H | cyclopropylmethyl | 532.13 |
| 4-chlorophenyl | 2,5-dimethoxyphenyl | H | cyclopropylmethyl | 548.13 |
| 4-chlorophenyl | 2,4-dimethoxyphenyl | H | cyclopropylmethyl | 548.13 |
| 4-chlorophenyl | 3,5-dimethoxyphenyl | H | cyclopropylmethyl | 548.13 |
| 4-chlorophenyl | 2-fluorophenyl | H | cyclopropylmethyl | 506.12 |
| 4-chlorophenyl | 3-fluorophenyl | H | cyclopropylmethyl | 506.12 |
| 4-chlorophenyl | 4-fluorophenyl | H | cyclopropylmethyl | 506.12 |
| 4-chlorophenyl | 3-chloro,4-fluorophenyl | H | cyclopropylmethyl | 540.13 |
| 4-chlorophenyl | 3,4-difluorophenyl | H | cyclopropylmethyl | 524.12 |
| 4-chlorophenyl | 2,4-difluorophenyl | H | cyclopropylmethyl | 524.12 |
| 4-chlorophenyl | 2,6-difluorophenyl | H | cyclopropylmethyl | 524.12 |
| 4-chlorophenyl | 2-5-difluorophenyl | H | cyclopropylmethyl | 524.12 |
| 4-chlorophenyl | 3-cyanophenyl | H | cyclopropylmethyl | 513.12 |
| 4-chlorophenyl | 4-cyanophenyl | H | cyclopropylmethyl | 513.12 |
| 4-chlorophenyl | N, R2, R7 = pyrrolidine | N, R2, R7 = pyrrolidine | cyclopropylmethyl | 466.11 |
| 4-chlorophenyl | N, R2, R7 = morpholine | N, R2, R7 = morpholine | cyclopropylmethyl | 482.12 |
| 4-chlorophenyl | Phenyl | Methyl | cyclopropylmethyl | 502.12 |
| 4-chlorophenyl | isopropyl | isopropyl | cyclopropylmethyl | 496.12 |
| 4-chlorophenyl | Methyl | Methyl | cyclopropylmethyl | 440.11 |
| 4-chlorophenyl | ethyl | ethyl | cyclopropylmethyl | 468.11 |
| 4-chlorophenyl | Phenyl | H | cyclopentyl | 502.12 |
| 4-chlorophenyl | 3,5-dichlorophenyl | H | cyclopentyl | 572.13 |
| 4-chlorophenyl | 2-chlorophenyl | H | cyclopentyl | 536.13 |
| 4-chlorophenyl | 3-chlorophenyl | H | cyclopentyl | 536.13 |
| 4-chlorophenyl | 4-chlorophenyl | H | cyclopentyl | 536.13 |
| 4-chlorophenyl | 2-methoxyphenyl | H | cyclopentyl | 532.13 |
| 4-chlorophenyl | 3-methoxyphenyl | H | cyclopentyl | 532.13 |
| 4-chlorophenyl | 4-methoxyphenyl | H | cyclopentyl | 532.13 |
| 4-chlorophenyl | 3,4-methylenedioxyphenyl | H | cyclopentyl | 546.13 |
| 4-chlorophenyl | 2,5-dimethoxyphenyl | H | cyclopentyl | 562.13 |
| 4-chlorophenyl | 2,4-dimethoxyphenyl | H | cyclopentyl | 562.13 |
| 4-chlorophenyl | 3,5-dimethoxyphenyl | H | cyclopentyl | 562.13 |
| 4-chlorophenyl | 2-fluorophenyl | H | cyclopentyl | 520.12 |
| 4-chlorophenyl | 3-fluorophenyl | H | cyclopentyl | 520.12 |
| 4-chlorophenyl | 4-fluorophenyl | H | cyclopentyl | 520.12 |
| 4-chlorophenyl | 3-chloro,4-fluorophenyl | H | cyclopentyl | 554.13 |
| 4-chlorophenyl | 3,4-difluorophenyl | H | cyclopentyl | 538.13 |
| 4-chlorophenyl | 2,4-difluorophenyl | H | cyclopentyl | 538.13 |
| 4-chlorophenyl | 2,6-difluorophenyl | H | cyclopentyl | 538.1 |
| 4-chlorophenyl | 2-5-difluorophenyl | H | cyclopentyl | 538.13 |
| 4-chlorophenyl | 3-cyanophenyl | H | cyclopentyl | 527.12 |
| 4-chlorophenyl | 4-cyanophenyl | H | cyclopentyl | 527.12 |
| 4-chlorophenyl | N, R2, R7 = pyrrolidine | N, R2, R7 = pyrrolidine | cyclopentyl | 480.12 |
| 4-chlorophenyl | N, R2, R7 = morpholine | N, R2, R7 = morpholine | cyclopentyl | 496.12 |
| 4-chlorophenyl | Phenyl | Methyl | cyclopentyl | 516.12 |
| 4-chlorophenyl | Methyl | Methyl | cyclopentyl | 454.11 |
| 4-chlorophenyl | ethyl | ethyl | cyclopentyl | 482.12 |

-continued

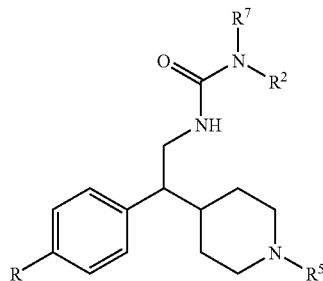

| R | R² | R⁷ | R⁵ | obs M + 1 m/z |
|---|---|---|---|---|
| 4-chlorophenyl | Phenyl | H | 3,4-ethylenedioxybenzyl | 582.14 |
| 4-chlorophenyl | 3,5-dichlorophenyl | H | 3,4-ethylenedioxybenzyl | 652.16 |
| 4-chlorophenyl | 2-chlorophenyl | H | 3,4-ethylenedioxybenzyl | 616.14 |
| 4-chlorophenyl | 3-chlorophenyl | H | 3,4-ethylenedioxybenzyl | 616.14 |
| 4-chlorophenyl | 4-chlorophenyl | H | 3,4-ethylenedioxybenzyl | 616.14 |
| 4-chlorophenyl | 2-methoxyphenyl | H | 3,4-ethylenedioxybenzyl | 612.14 |
| 4-chlorophenyl | 3-methoxyphenyl | H | 3,4-ethylenedioxybenzyl | 612.14 |
| 4-chlorophenyl | 4-methoxyphenyl | H | 3,4-ethylenedioxybenzyl | 612.14 |
| 4-chlorophenyl | 3,4-methylenedioxyphenyl | H | 3,4-ethylenedioxybenzyl | 626.15 |
| 4-chlorophenyl | 2,5-dimethoxyphenyl | H | 3,4-ethylenedioxybenzyl | 642.15 |
| 4-chlorophenyl | 2,4-dimethoxyphenyl | H | 3,4-ethylenedioxybenzyl | 642.15 |
| 4-chlorophenyl | 3,5-dimethoxyphenyl | H | 3,4-ethylenedioxybenzyl | 642.15 |
| 4-chlorophenyl | 2-fluorophenyl | H | 3,4-ethylenedioxybenzyl | 600.14 |
| 4-chlorophenyl | 3-fluorophenyl | H | 3,4-ethylenedioxybenzyl | 600.14 |
| 4-chlorophenyl | 4-fluorophenyl | H | 3,4-ethylenedioxybenzyl | 600.14 |
| 4-chlorophenyl | 3-chloro,4-fluorophenyl | H | 3,4-ethylenedioxybenzyl | 634.15 |
| 4-chlorophenyl | 3,4-difluorophenyl | H | 3,4-ethylenedioxybenzyl | 618.14 |
| 4-chlorophenyl | 2,4-difluorophenyl | H | 3,4-ethylenedioxybenzyl | 618.14 |
| 4-chlorophenyl | 2,6-difluorophenyl | H | 3,4-ethylenedioxybenzyl | 618.14 |
| 4-chlorophenyl | 2-5-difluorophenyl | H | 3,4-ethylenedioxybenzyl | 618.14 |
| 4-chlorophenyl | 3-cyanophenyl | H | 3,4-ethylenedioxybenzyl | 607.14 |
| 4-chlorophenyl | 4-cyanophenyl | H | 3,4-ethylenedioxybenzyl | 607.14 |
| 4-chlorophenyl | N, R2, R7 = pyrrolidine | N, R2, R7 = pyrrolidine | 3,4-ethylenedioxybenzyl | 560.13 |
| 4-chlorophenyl | N, R2, R7 = morpholine | N, R2, R7 = morpholine | 3,4-ethylenedioxybenzyl | 576.14 |
| 4-chlorophenyl | Phenyl | Methyl | 3,4-ethylenedioxybenzyl | 596.14 |
| 4-chlorophenyl | Methyl | Methyl | 3,4-ethylenedioxybenzyl | 534.13 |
| 4-chlorophenyl | ethyl | ethyl | 3,4-ethylenedioxybenzyl | 562.13 |
| 4-fluorophenyl | 3,5-difluorophenyl | N—R⁷ absent | cyclopropylmethyl | 493.1 |
| 4-fluorophenyl | 3,5-difluorophenyl | N—R⁷ absent | cyclopentyl | 507.1 |
| 4-fluorophenyl | 3-chlorophenyl | N—R⁷ absent | cyclopropylmethyl | 491.1 |
| 4-fluorophenyl | 3-chlorophenyl | N—R⁷ absent | cyclopentyl | 505.1 |
| 4-fluorophenyl | 3-cyanophenyl | N—R⁷ absent | cyclopropylmethyl | 482.1 |
| 4-fluorophenyl | 3-cyanophenyl | N—R⁷ absent | cyclopentyl | 496.1 |
| 4-fluorophenyl | 3-fluorophenyl | N—R⁷ absent | cyclopropylmethyl | 475.1 |
| 4-fluorophenyl | 3-fluorophenyl | N—R⁷ absent | cyclopentyl | 489.1 |
| 4-fluorophenyl | 4-chlorophenyl | N—R⁷ absent | cyclopropylmethyl | 491.1 |
| 4-fluorophenyl | 4-chlorophenyl | N—R⁷ absent | cyclopentyl | 505.1 |
| 4-fluorophenyl | 4-cyanophenyl | N—R⁷ absent | cyclopropylmethyl | 482.1 |
| 4-fluorophenyl | 4-cyanophenyl | N—R⁷ absent | cyclopentyl | 496.1 |
| 4-fluorophenyl | 4-fluorophenyl | N—R⁷ absent | cyclopropylmethyl | 475.1 |
| 4-fluorophenyl | 4-fluorophenyl | N—R⁷ absent | cyclopentyl | 489.1 |
| 4-fluorophenyl | Phenyl | N—R⁷ absent | cyclopropylmethyl | 457.1 |
| 4-fluorophenyl | Phenyl | N—R⁷ absent | cyclopentyl | 471.1 |
| 4-fluorophenyl | 3,5-dichlorophenyl | N—R⁷ absent | cyclopropylmethyl | 525.1 |
| 4-fluorophenyl | 3,5-dichlorophenyl | N—R⁷ absent | cyclopentyl | 539.1 |
| 4-fluorophenyl | 3,5-dimethoxyphenyl | N—R⁷ absent | cyclopropylmethyl | 517.1 |
| 4-fluorophenyl | 3,5-dimethoxyphenyl | N—R⁷ absent | cyclopentyl | 531.1 |
| 4-fluorophenyl | 3-methoxyphenyl | N—R⁷ absent | cyclopropylmethyl | 487.1 |
| 4-fluorophenyl | 3-methoxyphenyl | N—R⁷ absent | cyclopentyl | 501.1 |
| 4-fluorophenyl | 3,5-dimethoxyphenyl | N—R⁷ absent | cyclopropylmethyl | 517.1 |
| 4-fluorophenyl | 3,5-dimethoxyphenyl | N—R⁷ absent | cyclopentyl | 531.1 |
| 4-fluorophenyl | 3,4-methylenedioxyphenyl | N—R⁷ absent | cyclopropylmethyl | 501.1 |
| 4-fluorophenyl | 3,4-methylenedioxyphenyl | N—R⁷ absent | cyclopentyl | 515.1 |

-continued

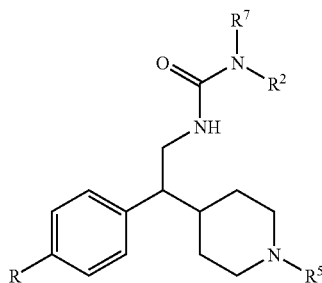

| R | R² | R⁷ | R⁵ | obs M+1 m/z |
|---|---|---|---|---|
| 4-fluorophenyl | 4-methoxyphenyl | N—R⁷ absent | cyclopropylmethyl | 487.1 |
| 4-fluorophenyl | 4-methoxyphenyl | N—R⁷ absent | cyclopentyl | 501.1 |

What is claimed:
1. A compound represented by the structural formula

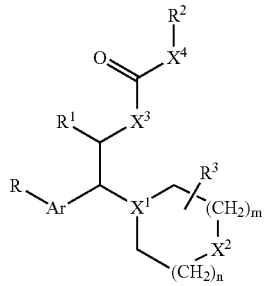

or a pharmaceutically acceptable salt thereof, wherein
m is 1;
n is 1;
$X^1$ is N;
$X^2$ is N—$R^5$;
$X^3$ is O or N—$R^6$;
$X^4$ is NH, N—$R^7$ or N, and when $X^4$ is N, $R^2$ and $X^4$ can join together to form a heterocycloalkyl group wherein said heterocycloalkyl group is piperidine, pyrrolidine, morpholine, piperazine, thiomorpholine,

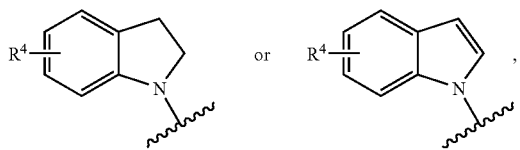

where the N of $X^4$ is the heteroatom of said heterocycloalkyl group, wherein said heterocycloalkyl group can be optionally substituted with one or more alkyl, aryl, aralkyl, or cycloalkylalkyl;
Ar is an arylene group;
R is $R^4$-phenyl, $R^4$-pyridyl, $R^4$-pyridyl-N-oxide, or $R^4$-pyrimidyl;
$R^1$ is hydrogen or (C₁-C₃)alkyl;
$R^2$ is $R^8$-phenyl;

$R^3$ is hydrogen, OH, —O(C₁-C₃)alkyl, or non-substituted or halosubstituted (C₁-C₃)alkyl;
$R^4$ and $R^8$ maybe the same or different, may number 0 to 3, each being independently selected from the group consisting of hydrogen, —(C₁-C₆)alkyl, —(C₃-C₇)cycloalkyl, halo, —CN, (C₁-C₆)alkoxy, —CF₃, —OCF₃, —CONH₂, —CONH(C₁-C₆)alkyl, —CON(C₁-C₆)alkyl (C₁-C₆)alkyl, —NH₂, —NHC(O)(C₁-C₆)alkyl, —NHC(O)NH(C₁-C₆)alkyl, —NHC(O)N((C₁-C₆)alkyl)((C₁-C₆)alkyl), —NHSO₂(C₁-C₆)alkyl, —S(C₁-C₆)alkyl, —SO(C₁-C₆)alkyl, —SO₂(C₁-C₆)alkyl, —SO₂NH(C₁-C₆)alkyl, —O(C₁-C₃)alkyleneO—, and NO₂ or two adjacent $R^4$ or two adjacent $R^8$ groups together may form a methylenedioxy, propylenedioxy or ethylenedioxy group;
$R^5$ is hydrogen, nonsubstituted or halosubstituted —(C₁-C₆)alkyl, or nonsubstituted or halosubstituted (C₃-C₇) cycloalkyl;
$R^6$ and $R^7$ may be the same or different, each being independently selected from hydrogen, nonsubstituted or halosubstituted (C₁-C₃)alkyl; or $R^6$ and $R^7$ can be joined together to form an imidazolone ring.
2. The compound of claim 1 wherein
$X^1$ is N;
$X^2$ is N—$R^5$;
$X^3$ is O or N—$R^6$;
$X^4$ is N—$R^7$;
Ar is 1,4-phenylene;
R is $R^4$-phenyl, or $R^4$-pyridyl when $R^4$ is present once and is located at the meta position of said phenyl or pyridyl;
$R^1$ is hydrogen;
$R^2$ is $R^8$-phenyl, where $R^8$ is 1-3 substituents which may be the same or different, each being independently selected from halogen, CF₃—, or (C₁-C₃)alkoxy-;
$R^3$ is hydrogen or methyl;
$R^4$ is 1 to 3 substituents which may be the same or different, each being independently selected from hydrogen, halogen, or CN;
$R^5$ is hydrogen, or nonsubstituted or halosubstituted (C₁-C₆)alkyl;
$R^6$ and $R^7$ are hydrogen, or are joined together to form an imidazolone ring; and
m and n are the same or different and are equal to 1.
3. The compound of claim 2 wherein $X^3$ is O or NH.
4. The compound of claim 3 wherein $X^4$ is NH.

5. The compound of claim 4 wherein R is $R^4$-phenyl or $R^4$-pyridyl and $R^4$ is present once and is located at the meta position.

6. The compound of claim 5 wherein $R^2$ is $R^8$-phenyl, where $R^8$ is 1 to 3 substituents which may be same or different, each being independently selected from halogen, $CF_3$, or $(C_1-C_3)$alkyl-O—.

7. The compound of claim 1 wherein $R^3$ is hydrogen or methyl.

8. The compound of claim 1 wherein $R^4$ is 1 to 3 substituents which may be the same or different, each being independently selected from hydrogen, halogen or CN.

9. The compound of claim 1 wherein $R^5$ is hydrogen, or nonsubstituted or halosubstituted $(C_1-C_6)$alkyl.

10. The compound of claim 1 wherein $R^6$ and $R^7$ are hydrogen.

11. The compound of claim 1 wherein $R^6$ and $R^7$ are joined together to form an imidazolone ring; m and n are 1.

12. The compound of claim 1 wherein said compound has the formula Ic-a

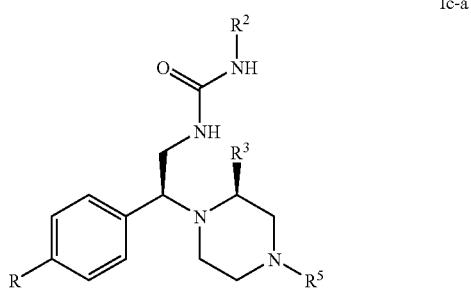

wherein
R is $R^4$-phenyl, $R^4$-pyridyl, $R^4$-pyridyl-N-oxide, or $R^4$-pyrimidyl;
$R^2$ is $R^8$-phenyl;
$R^3$ is hydrogen, OH, —O$(C_1-C_3)$alkyl, or non-substituted or halosubstituted $(C_1-C_3)$alkyl;
$R^4$ and $R^8$ maybe the same or different, may number 0 to 3, each being independently selected from the group consisting of hydrogen, —$(C_1-C_6)$alkyl, —$(C_3-C_7)$cycloalkyl, halo, —CN, $(C_1-C_6)$alkoxy, —$CF_3$, —$OCF_3$, —$CONH_2$, —$CONH(C_1-C_6)$alkyl, —$CON(C_1-C_6)$alkyl $(C_1-C_6)$alkyl, —$NH_2$, —$NHC(O)(C_1-C_6)$alkyl, —$NHC(O)NH(C_1-C_6)$alkyl, —$NHC(O)N((C_1-C_6)$alkyl$)((C_1-C_6)$alkyl$)$, —$NHSO_2(C_1-C_6)$alkyl, —$S(C_1-C_6)$alkyl, —$SO(C_1-C_6)$alkyl, —$SO_2(C_1-C_6)$alkyl, —$SO_2NH(C_1-C_6)$alkyl, —$O(C_1-C_3)$alkyleneO—, and $NO_2$ or two adjacent $R^4$ or two adjacent $R^8$ groups together may form a methylenedioxy, propylenedioxy or ethylenedioxy group;
$R^5$ is hydrogen, nonsubstituted or halosubstituted —$(C_1-C_6)$alkyl, or nonsubstituted or halosubstituted $(C_3-C_7)$ cycloalkyl.

13. The compound of claim 1 wherein said compound has the formula Ic-b

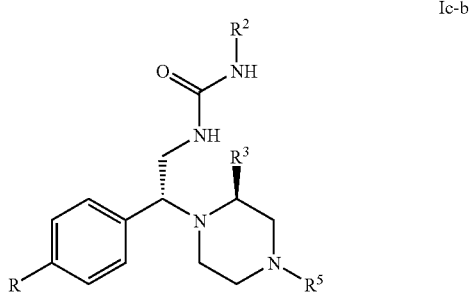

wherein
R is $R^4$-phenyl, $R^4$-pyridyl, $R^4$-pyridyl-N-oxide, or $R^4$-pyrimidyl;
$R^2$ is $R^8$-phenyl;
$R^3$ is hydrogen, OH, —O$(C_1-C_3)$alkyl, or non-substituted or halosubstituted $(C_1-C_3)$alkyl;
$R^4$ and $R^8$ maybe the same or different, may number 0 to 3, each being independently selected from the group consisting of hydrogen, —$(C_1-C_6)$alkyl, —$(C_3-C_7)$cycloalkyl, halo, —CN, $(C_1-C_6)$alkoxy, —$CF_3$, —$OCF_3$, —$CONH_2$, —$CONH(C_1-C_6)$alkyl, —$CON(C_1-C_6)$alkyl $(C_1-C_6)$alkyl, —$NH_2$, —$NHC(O)(C_1-C_6)$alkyl, —$NHC(O)NH(C_1-C_6)$alkyl, —$NHC(O)N((C_1-C_6)$alkyl$)((C_1-C_6)$alkyl$)$, —$NHSO_2(C_1-C_6)$alkyl, —$S(C_1-C_6)$alkyl, —$SO(C_1-C_6)$alkyl, —$SO_2(C_1-C_6)$alkyl, —$SO_2NH(C_1-C_6)$alkyl, —$O(C_1-C_3)$alkyleneO—, and $NO_2$ or two adjacent $R^4$ or two adjacent $R^8$ groups together may form a methylenedioxy, propylenedioxy or ethylenedioxy group;
$R^5$ is hydrogen, nonsubstituted or halosubstituted —$(C_1-C_6)$alkyl, or nonsubstituted or halosubstituted $(C_3-C_7)$ cycloalkyl.

14. The compound of claim 1 selected from the group consisting of:

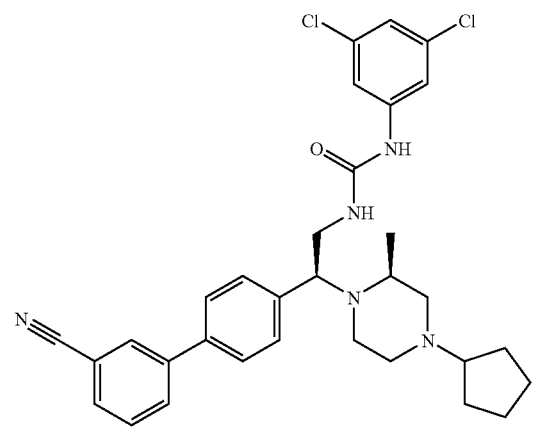

-continued

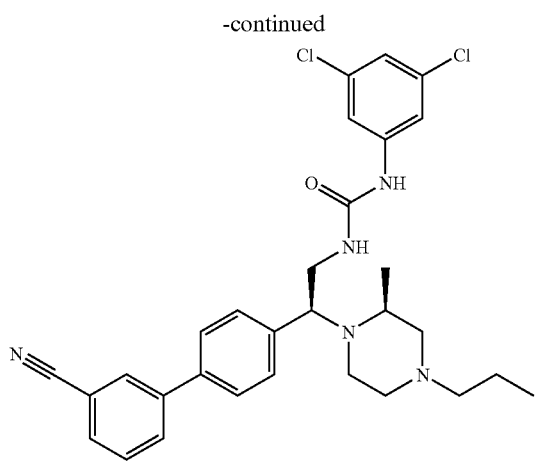

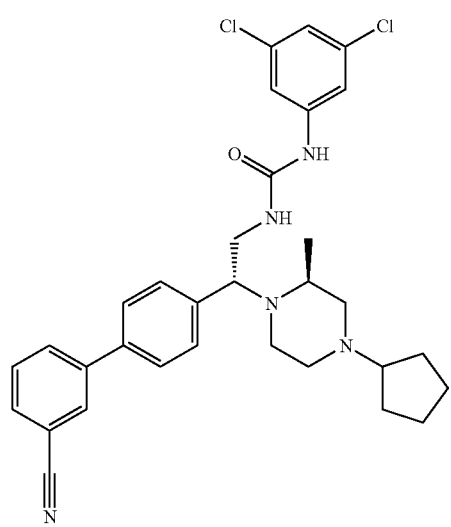

and

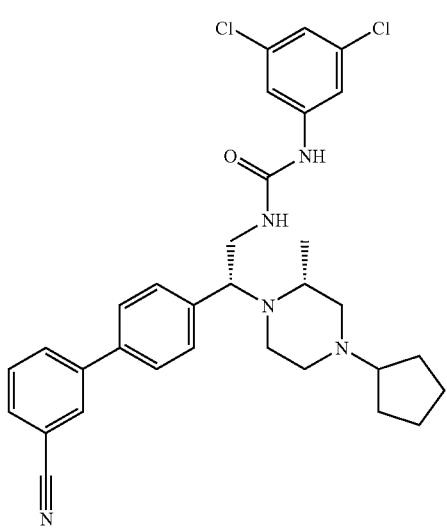

-continued

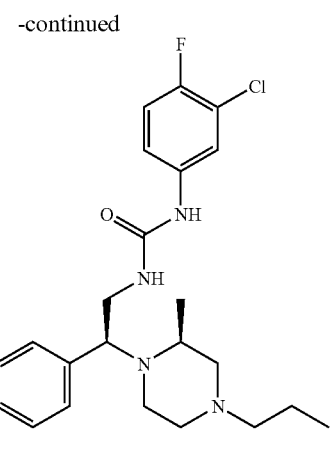

or a pharmaceutically acceptable salt thereof.

15. A pharmaceutical composition comprising a therapeutically effective amount of at least one compound of claim 1, or a pharmaceutically acceptable salt thereof, in combination with at least one pharmaceutically acceptable carrier.

16. A method of treating obesity comprising administering to a mammal in need of such treatment a therapeutically effective amount of at least one compound of claim 1 or a pharmaceutically acceptable salt of said compound.

17. A pharmaceutical composition which comprises a therapeutically effective amount of a composition comprising:
   a first compound, said first compound being a compound of claim 1, or a pharmaceutically acceptable salt of said compound;
   a second compound, said second compound being an anti-obesity agent, a $\beta_3$ agonist, a thryomimetic agent, an anorectic agent or an NPY antagonist; and
   a pharmaceutically acceptable carrier thereof.

18. A pharmaceutical composition which comprises a therapeutically effective amount of a composition comprising:
   a first compound, said first compound being a compound of claim 1, or a pharmaceutically acceptable salt of said compound;
   a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and
   a pharmaceutically acceptable carrier therefor.

19. A pharmaceutical composition made by combining at least one compound of claim 1, or a pharmaceutically acceptable salt thereof, and at least one pharmaceutically acceptable carrier.

20. A process for making a pharmaceutical composition comprising combining at least one compound of claim 1, or a pharmaceutically acceptable salt thereof, and at least one pharmaceutically acceptable carrier.

* * * * *